US012570716B2

(12) United States Patent
Jensen et al.

(10) Patent No.: US 12,570,716 B2
(45) Date of Patent: Mar. 10, 2026

(54) ANTI-DINITROPHENOL CHIMERIC ANTIGEN RECEPTORS

(71) Applicant: Seattle Children's Hospital, Seattle, WA (US)

(72) Inventors: Michael C. Jensen, Seattle, WA (US); James F. Matthaei, Seattle, WA (US); Joseph K. Cheng, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 742 days.

(21) Appl. No.: 17/758,959

(22) PCT Filed: Feb. 2, 2021

(86) PCT No.: PCT/US2021/016177
§ 371 (c)(1),
(2) Date: Jul. 15, 2022

(87) PCT Pub. No.: WO2021/158523
PCT Pub. Date: Aug. 12, 2021

(65) Prior Publication Data

US 2023/0068879 A1 Mar. 2, 2023

Related U.S. Application Data

(60) Provisional application No. 62/969,931, filed on Feb. 4, 2020.

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/40*** | (2025.01) |
| ***A61K 40/41*** | (2025.01) |
| ***A61P 35/00*** | (2006.01) |
| ***C07K 14/705*** | (2006.01) |
| ***C07K 14/71*** | (2006.01) |

(52) U.S. Cl.
CPC .......... *C07K 14/7051* (2013.01); *A61K 40/11* (2025.01); *A61K 40/31* (2025.01); *A61K 40/414* (2025.01); *A61K 2239/31* (2023.05); *A61K 2239/47* (2023.05); *A61K 2239/49* (2023.05)

(58) Field of Classification Search
None
See application file for complete search history.

(56) References Cited

U.S. PATENT DOCUMENTS

| | | | |
|---|---|---|---|
| 5,116,964 | A | 5/1992 | Capon et al. |
| 5,202,238 | A | 4/1993 | Fell, Jr. et al. |
| 5,216,132 | A | 6/1993 | Basi |
| 5,359,046 | A | 10/1994 | Capon et al. |
| 5,482,856 | A | 1/1996 | Fell, Jr. et al. |
| 5,514,582 | A | 5/1996 | Capon et al. |
| 5,525,503 | A | 6/1996 | Rudd et al. |
| 5,538,866 | A | 7/1996 | Israeli et al. |
| 5,670,148 | A | 9/1997 | Sherwin et al. |
| 5,686,281 | A | 11/1997 | Roberts |
| 5,712,149 | A | 1/1998 | Roberts |
| 5,714,147 | A | 2/1998 | Capon et al. |
| 5,741,899 | A | 4/1998 | Capon et al. |
| 5,747,292 | A | 5/1998 | Greenberg et al. |
| 5,830,755 | A | 11/1998 | Nishimura et al. |
| 5,834,256 | A | 11/1998 | Finer et al. |
| 5,837,544 | A | 11/1998 | Capon et al. |
| 5,843,728 | A | 12/1998 | Seed et al. |
| 5,851,828 | A | 12/1998 | Seed et al. |
| 5,858,740 | A | 1/1999 | Finer et al. |
| 5,906,936 | A | 5/1999 | Eshhar et al. |
| 5,912,170 | A | 6/1999 | Seed et al. |
| 5,912,172 | A | 6/1999 | Eshhar et al. |
| 5,914,109 | A | 6/1999 | Zolla-Pazner et al. |
| 5,935,818 | A | 8/1999 | Israeli et al. |
| 5,969,102 | A | 10/1999 | Bram et al. |
| 6,004,781 | A | 12/1999 | Seed |
| 6,004,811 | A | 12/1999 | Seed et al. |
| 6,005,004 | A | 12/1999 | Katz et al. |
| 6,077,947 | A | 6/2000 | Capon et al. |
| 6,083,751 | A | 7/2000 | Feldhaus et al. |
| 6,103,521 | A | 8/2000 | Capon et al. |

(Continued)

FOREIGN PATENT DOCUMENTS

| | | |
|---|---|---|
| CN | 102775500 | 11/2012 |
| EP | 2 177 230 | 4/2010 |

(Continued)

OTHER PUBLICATIONS

Abken, H. et al. Chimeric T-Cell Receptors: Highly Specific Tools To Target Cytotoxic T-Lymphocytes To Tumour Cells, Cancer Treatment Reviews (1997); 23:97-112.

(Continued)

*Primary Examiner* — Manjunath N Rao
*Assistant Examiner* — Jae W Lee
(74) *Attorney, Agent, or Firm* — Knobbe. Martens, Olson & Bear, LLP

(57) ABSTRACT

Embodiments provided herein include methods and compositions comprising anti-dinitrophenol chimeric antigen receptors (CARs). Some embodiments include nucleic acids encoding such CARs, polypeptides encoded by such nucleic acids, cells comprising such nucleic acids or polypeptides, and methods utilizing such cells. Some embodiments also include the use of dinitrophenol (DNP) and derivatives thereof.

20 Claims, 13 Drawing Sheets

Specification includes a Sequence Listing.

(56) References Cited

U.S. PATENT DOCUMENTS 6,117,656 A 9/2000 Seed
6,132,718 A 10/2000 Hansen et al.
6,218,187 B1 4/2001 Finer et al.
6,261,787 B1 7/2001 Davis et al.
6,319,494 B1 11/2001 Capon et al.
6,392,013 B1 5/2002 Seed et al.
6,395,152 B1 5/2002 Wang
6,406,697 B1 6/2002 Capon et al.
6,407,221 B1 6/2002 Capon et al.
6,410,014 B1 6/2002 Seed et al.
6,410,319 B1 6/2002 Raubitschek et al.
6,432,403 B1 8/2002 Philips
6,521,602 B1 2/2003 Patel et al.
6,524,572 B1 2/2003 Li
6,699,972 B1 3/2004 Roffler et al.
6,753,162 B1 6/2004 Seed et al.
6,759,243 B2 7/2004 Kranz et al.
6,770,749 B2 8/2004 Ellenhorn et al.
6,953,668 B1 10/2005 Israeli et al.
7,037,647 B1 5/2006 Israeli et al.
7,049,136 B2 5/2006 Seed et al.
7,052,906 B1 5/2006 Lawson et al.
7,070,995 B2 7/2006 Jensen
7,105,159 B1 9/2006 Israeli et al.
7,217,421 B1 5/2007 McArthur et al.
7,265,209 B2 9/2007 Jensen
7,320,787 B2 1/2008 Seed et al.
7,348,004 B2 3/2008 Peters et al.
7,354,587 B1 4/2008 Hansen
7,354,762 B2 4/2008 Jensen
7,381,408 B2 6/2008 Mezo et al.
7,404,956 B2 7/2008 Peters et al.
7,435,596 B2 10/2008 Campana et al.
7,446,179 B2 11/2008 Jensen et al.
7,446,190 B2 11/2008 Sadelain et al.
7,446,191 B2 11/2008 Jensen
7,482,005 B2 1/2009 Kim
7,514,537 B2 4/2009 Jensen
7,569,663 B2 8/2009 Tykocinski et al.
7,572,891 B2 8/2009 Belldegrun et al.
7,618,817 B2 11/2009 Campbell
7,632,497 B2 12/2009 Stavenhagen
7,655,461 B2 2/2010 Finn et al.
7,666,424 B2 2/2010 Cheung et al.
7,723,111 B2 5/2010 Hwu et al.
7,741,465 B1 6/2010 Eshhar et al.
7,871,817 B2 1/2011 Voss et al.
7,906,620 B2 3/2011 Eisenbach et al.
7,919,079 B2 4/2011 Simmons et al.
7,939,059 B2 5/2011 Yang et al.
7,994,298 B2 8/2011 Zhang et al.
7,998,736 B2 8/2011 Morgan et al.
8,105,830 B2 1/2012 Weidanz et al.
8,148,154 B2 4/2012 Cheung et al.
8,163,887 B2 4/2012 Hansen
8,211,422 B2 7/2012 Eshhar et al.
RE43,586 E 8/2012 Israeli et al.
8,252,914 B2 8/2012 Zhang et al.
8,324,353 B2 12/2012 Jensen
8,389,282 B2 3/2013 Sadelain et al.
8,399,645 B2 3/2013 Campana et al.
8,409,577 B2 4/2013 Thompson et al.
8,450,112 B2 5/2013 Li et al.
8,465,743 B2 6/2013 Rosenberg et al.
8,486,911 B2 7/2013 Okada et al.
8,497,118 B2 7/2013 Jensen
8,741,306 B2 6/2014 Belldegrun et al.
8,802,374 B2 8/2014 Jensen
8,809,050 B2 8/2014 Vera et al.
8,822,196 B2 9/2014 Rosenberg et al.
8,822,647 B2 9/2014 Jensen
8,859,229 B2 10/2014 Rabinovich et al.
8,877,199 B2 11/2014 Rader et al.
8,906,682 B2 12/2014 June et al.
8,932,830 B2 1/2015 Peters et al.
8,946,385 B2 2/2015 Kawai
8,956,860 B2 2/2015 Vera et al.
9,023,621 B2 5/2015 Gurney et al.
9,040,669 B2 5/2015 Cheung et al.
9,062,127 B2 6/2015 Voss et al.
9,074,000 B2 7/2015 Scheinberg et al.
9,089,520 B2 7/2015 Brenner
9,101,609 B2 8/2015 Tan et al.
9,133,436 B2 9/2015 Riley et al.
9,156,915 B2 10/2015 Waldman et al.
9,163,258 B2 10/2015 Riddell et al.
9,175,308 B2 11/2015 Shiku et al.
9,211,321 B2 12/2015 Karlsson-Parra et al.
9,212,229 B2 12/2015 Schönfeld et al.
9,220,728 B2 12/2015 Sadelain et al.
9,226,936 B2 1/2016 Hu et al.
9,242,014 B2 1/2016 Kipps et al.
9,266,960 B2 2/2016 Morgan et al.
9,272,002 B2 3/2016 Powell, Jr. et al.
9,273,283 B2 3/2016 Sentman
9,279,008 B2 3/2016 Scholler et al.
9,334,330 B2 5/2016 Birkle et al.
9,345,748 B2 5/2016 Morgan et al.
9,352,036 B2 5/2016 McBride et al.
9,359,447 B2 6/2016 Feldman et al.
9,365,641 B2 6/2016 June et al.
9,393,268 B2 7/2016 Waldman et al.
9,393,292 B2 7/2016 Brenner
9,394,364 B2 7/2016 Ho et al.
9,394,368 B2 7/2016 Brogdon et al.
9,402,888 B2 8/2016 Hildegund et al.
9,408,904 B2 8/2016 Wright et al.
9,409,992 B2 8/2016 Ho et al.
9,409,994 B2 8/2016 Ho et al.
9,416,190 B2 8/2016 Ho et al.
9,422,351 B2 8/2016 Scholler et al.
9,434,935 B2 9/2016 Spencer et al.
9,446,105 B2 9/2016 Powell et al.
9,447,194 B2 9/2016 Jensen
9,453,075 B2 9/2016 Cheung et al.
9,464,140 B2 10/2016 June et al.
9,469,684 B2 10/2016 Finn et al.
9,476,028 B2 10/2016 Karlsson-Parra et al.
9,481,728 B2 11/2016 June et al.
9,487,800 B2 11/2016 Schonfeld et al.
9,492,499 B2 11/2016 Jaynes et al.
9,492,529 B2 11/2016 Karlsson-Parra et al.
9,493,740 B2 11/2016 Brenner et al.
9,499,629 B2 11/2016 June et al.
9,499,855 B2 11/2016 Hyde et al.
9,511,092 B2 12/2016 Campana et al.
9,518,123 B2 12/2016 June et al.
9,522,955 B2 12/2016 Rosenberg et al.
9,540,445 B2 1/2017 June et al.
9,540,448 B2 1/2017 Scheinberg et al.
9,561,291 B2 2/2017 Kovesdi et al.
9,562,087 B2 2/2017 Ring et al.
9,567,399 B1 2/2017 Campbell et al.
9,572,836 B2 2/2017 June et al.
9,572,837 B2 2/2017 Wu
9,573,988 B2 2/2017 Brogdon et al.
9,574,014 B2 2/2017 Williams et al.
9,587,020 B2 3/2017 Wu et al.
9,587,237 B2 3/2017 Hyde et al.
9,597,357 B2 3/2017 Gregory et al.
9,605,049 B2 3/2017 Campana et al.
9,624,292 B2 4/2017 Voss et al.
9,624,306 B2 4/2017 Morgan et al.
9,629,877 B2 4/2017 Cooper et al.
9,636,388 B2 5/2017 Lawman et al.
9,636,416 B2 5/2017 Peters et al.
9,642,906 B2 5/2017 Ramos et al.
9,650,428 B2 5/2017 Sampath et al.
9,657,105 B2 5/2017 Forman et al.
9,662,405 B2 5/2017 Waldman et al.
9,663,756 B1 5/2017 Lipkens et al.
9,663,763 B2 5/2017 Sentman
9,669,058 B2 6/2017 Li et al.
9,670,281 B2 6/2017 Lim et al.

(56) References Cited

U.S. PATENT DOCUMENTS

| | | | |
|---|---|---|---|
| 9,676,867 | B2 | 6/2017 | Marasco et al. |
| 9,688,740 | B2 | 6/2017 | Choi et al. |
| 9,688,760 | B2 | 6/2017 | Kufer et al. |
| 9,694,033 | B2 | 7/2017 | Yi et al. |
| 9,701,758 | B2 | 7/2017 | Cooper et al. |
| 9,708,384 | B2 | 7/2017 | Scholler et al. |
| 9,714,278 | B2 | 7/2017 | June et al. |
| 9,717,745 | B2 | 8/2017 | He |
| 9,725,519 | B2 | 8/2017 | Masuko et al. |
| 9,733,245 | B2 | 8/2017 | Kawai |
| 9,738,726 | B2 | 8/2017 | Dimitrov et al. |
| 9,745,368 | B2 | 8/2017 | Milone et al. |
| 9,765,142 | B2 | 9/2017 | Dimitrov et al. |
| 9,765,156 | B2 | 9/2017 | June et al. |
| 9,765,330 | B1 | 9/2017 | Niazi et al. |
| 9,765,342 | B2 | 9/2017 | Kochenderfer |
| 9,777,061 | B2 | 10/2017 | Ebersbach et al. |
| 9,777,064 | B2 | 10/2017 | Wang et al. |
| 9,783,591 | B2 | 10/2017 | June et al. |
| 9,789,174 | B2 | 10/2017 | Karlsson-Parra et al. |
| 9,790,267 | B2 | 10/2017 | Kaplan |
| 9,790,278 | B2 | 10/2017 | Sentman et al. |
| 9,790,282 | B2 | 10/2017 | Orentas et al. |
| 9,790,467 | B2 | 10/2017 | Kevlahan et al. |
| 9,796,783 | B2 | 10/2017 | Agerstam et al. |
| 9,802,997 | B2 | 10/2017 | Mahr et al. |
| 9,803,022 | B2 | 10/2017 | Ho et al. |
| 9,808,486 | B2 | 11/2017 | Georgiou et al. |
| 9,809,581 | B2 | 11/2017 | Chen et al. |
| 9,815,901 | B2 | 11/2017 | Brogdon et al. |
| 9,821,011 | B1 | 11/2017 | Sentman |
| 9,821,012 | B2 | 11/2017 | Wu et al. |
| 9,822,340 | B1 | 11/2017 | Sentman |
| 9,828,399 | B2 | 11/2017 | Tremblay et al. |
| 9,828,435 | B2 | 11/2017 | Evans et al. |
| 9,833,476 | B2 | 12/2017 | Zhang et al. |
| 9,833,480 | B2 | 12/2017 | Junghans et al. |
| 9,834,545 | B2 | 12/2017 | Chen et al. |
| 9,834,590 | B2 | 12/2017 | Campana et al. |
| 9,840,548 | B2 | 12/2017 | Mahr et al. |
| 9,845,362 | B2 | 12/2017 | Mukherjee |
| 9,849,092 | B2 | 12/2017 | Peyman |
| 9,855,297 | B2 | 1/2018 | Duchateau et al. |
| 9,855,298 | B2 | 1/2018 | Bot et al. |
| 9,856,322 | B2 | 1/2018 | Campana et al. |
| 9,856,497 | B2 | 1/2018 | Qi et al. |
| 9,856,501 | B2 | 1/2018 | O'Keefe et al. |
| 9,862,756 | B2 | 1/2018 | Mahr et al. |
| 9,862,775 | B2 | 1/2018 | Kwon et al. |
| 9,868,774 | B2 | 1/2018 | Orentas et al. |
| 9,868,951 | B2 | 1/2018 | Hu et al. |
| 9,873,894 | B2 | 1/2018 | Conway et al. |
| 9,879,087 | B2 | 1/2018 | DeSander et al. |
| 9,885,021 | B2 | 2/2018 | Bollard et al. |
| 9,889,160 | B2 | 2/2018 | Jantz et al. |
| 9,889,161 | B2 | 2/2018 | Jantz et al. |
| 9,890,393 | B2 | 2/2018 | Duchateau et al. |
| 10,279,047 | B2 | 5/2019 | Won et al. |
| 10,780,118 | B2 | 9/2020 | Jensen |
| 11,759,480 | B2 | 9/2023 | Low et al. |
| 11,779,602 | B2 | 10/2023 | Low |
| 11,850,262 | B2 | 12/2023 | Low et al. |
| 12,144,850 | B2 | 11/2024 | Low et al. |
| 12,150,981 | B2 | 11/2024 | Low et al. |
| 12,240,870 | B2 | 3/2025 | Messmann et al. |
| 12,269,862 | B2 | 4/2025 | Low et al. |
| 2001/0031252 | A1 | 10/2001 | Low et al. |
| 2002/0004052 | A1 | 1/2002 | Berd et al. |
| 2002/0111474 | A1 | 8/2002 | Capon et al. |
| 2003/0175288 | A1 | 9/2003 | Itoh |
| 2004/0171096 | A1 | 9/2004 | Ferguson |
| 2005/0113564 | A1 | 5/2005 | Campana |
| 2006/0155115 | A1 | 7/2006 | Jakobsen et al. |
| 2008/0051380 | A1 | 2/2008 | Auerbach et al. |
| 2009/0005257 | A1 | 1/2009 | Jespers et al. |
| 2009/0011984 | A1 | 1/2009 | Yla-Herttuala et al. |
| 2009/0202501 | A1 | 8/2009 | Zhang et al. |
| 2010/0135974 | A1 | 6/2010 | Eshhar et al. |
| 2010/0278830 | A1 | 11/2010 | Shoemaker et al. |
| 2011/0172254 | A1 | 7/2011 | Leamon |
| 2011/0178279 | A1 | 7/2011 | Williams et al. |
| 2012/0093842 | A1 | 4/2012 | Eshhar et al. |
| 2012/0302466 | A1 | 11/2012 | Sentman |
| 2013/0143895 | A1 | 6/2013 | McAllister et al. |
| 2013/0156794 | A1 | 6/2013 | Eshhar et al. |
| 2013/0287752 | A1 | 10/2013 | Davila |
| 2013/0309258 | A1 | 11/2013 | June et al. |
| 2013/0309267 | A1 | 11/2013 | Simmons et al. |
| 2013/0323834 | A1 | 12/2013 | Brenner |
| 2013/0344066 | A1 | 12/2013 | Faham et al. |
| 2014/0004132 | A1 | 1/2014 | Brenner et al. |
| 2014/0004137 | A1 | 1/2014 | Ovaa et al. |
| 2014/0017170 | A1 | 1/2014 | Irvine et al. |
| 2014/0120136 | A1 | 5/2014 | Katsikis et al. |
| 2014/0134142 | A1 | 5/2014 | Smith et al. |
| 2014/0134720 | A1 | 5/2014 | Stauss et al. |
| 2014/0227237 | A1 | 8/2014 | June et al. |
| 2014/0255363 | A1 | 9/2014 | Metelitsa et al. |
| 2014/0271582 | A1 | 9/2014 | Forman et al. |
| 2014/0271635 | A1 | 9/2014 | Brogdon et al. |
| 2014/0274909 | A1 | 9/2014 | Orentas et al. |
| 2014/0286973 | A1 | 9/2014 | Powell |
| 2014/0286987 | A1 | 9/2014 | Spencer et al. |
| 2014/0308259 | A1 | 10/2014 | Scholler et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0378389 | A1 | 12/2014 | Robbins et al. |
| 2015/0110760 | A1 | 4/2015 | Zhang et al. |
| 2015/0139943 | A1 | 5/2015 | Campana et al. |
| 2015/0152181 | A1 | 6/2015 | Sentman et al. |
| 2015/0225470 | A1 | 8/2015 | Zhang et al. |
| 2015/0238631 | A1 | 8/2015 | Kim et al. |
| 2015/0283178 | A1 | 10/2015 | June et al. |
| 2015/0306141 | A1 | 10/2015 | Jensen et al. |
| 2015/0307564 | A1 | 10/2015 | Young et al. |
| 2015/0307842 | A1 | 10/2015 | Sentman |
| 2015/0314014 | A1 | 11/2015 | Lauremann |
| 2015/0320799 | A1 | 11/2015 | Low et al. |
| 2015/0328292 | A1 | 11/2015 | Spencer et al. |
| 2015/0368342 | A1 | 12/2015 | Wu et al. |
| 2016/0046700 | A1 | 2/2016 | Foster et al. |
| 2016/0046724 | A1 | 2/2016 | Brogdon et al. |
| 2016/0051651 | A1 | 2/2016 | Brogdon et al. |
| 2016/0058857 | A1 | 3/2016 | Spencer et al. |
| 2016/0068601 | A1 | 3/2016 | Brogdon et al. |
| 2016/0096892 | A1 | 4/2016 | Brogdon et al. |
| 2016/0120907 | A1 | 5/2016 | Sentman |
| 2016/0136190 | A1 | 5/2016 | Weichert et al. |
| 2016/0151465 | A1 | 6/2016 | Slawin et al. |
| 2016/0166613 | A1 | 6/2016 | Spencer et al. |
| 2016/0175359 | A1 | 6/2016 | Spencer et al. |
| 2016/0340649 | A1 | 11/2016 | Brown et al. |
| 2016/0361360 | A1 | 12/2016 | Chang et al. |
| 2017/0166877 | A1 | 6/2017 | Bayle et al. |
| 2017/0290900 | A1 | 10/2017 | Low et al. |
| 2017/0306303 | A1 | 10/2017 | Taunton et al. |
| 2017/0340672 | A1 | 11/2017 | Wu et al. |
| 2017/0356010 | A1 | 12/2017 | Frost et al. |
| 2018/0002435 | A1 | 1/2018 | Sasu et al. |
| 2018/0100026 | A1 | 4/2018 | Kim et al. |
| 2018/0169109 | A1 | 6/2018 | Bradner et al. |
| 2018/0264038 | A1 | 9/2018 | Blazar |
| 2018/0311269 | A1 | 11/2018 | Lobb |
| 2019/0161531 | A1 | 5/2019 | Pule et al. |
| 2019/0169289 | A1 | 6/2019 | Young et al. |
| 2019/0209611 | A1 | 7/2019 | Eckardt et al. |
| 2019/0224237 | A1 | 7/2019 | Jensen et al. |
| 2019/0255109 | A1 | 8/2019 | Low |
| 2019/0292517 | A1 | 9/2019 | Cheung et al. |
| 2019/0316069 | A1 | 10/2019 | Hadrup |
| 2019/0388468 | A1 | 12/2019 | Lock et al. |
| 2020/0023009 | A1 | 1/2020 | Low et al. |
| 2020/0087399 | A1 | 3/2020 | Jensen et al. |

(56) References Cited

U.S. PATENT DOCUMENTS

| | | | |
|---|---|---|---|
| 2020/0354477 | A1 | 11/2020 | Jensen |
| 2020/0405760 | A1 | 12/2020 | Low et al. |
| 2021/0317407 | A1 | 10/2021 | Jensen et al. |
| 2022/0125841 | A1 | 4/2022 | Jensen et al. |
| 2022/0257652 | A1 | 8/2022 | Jensen |
| 2022/0280648 | A1 | 9/2022 | Low |
| 2023/0172981 | A1 | 6/2023 | Jensen |
| 2023/0322925 | A1 | 10/2023 | Jensen |
| 2024/0075069 | A1 | 3/2024 | Low et al. |
| 2024/0165159 | A1 | 5/2024 | Low et al. |
| 2025/0144195 | A1 | 5/2025 | Low et al. |

FOREIGN PATENT DOCUMENTS

| | | | |
|---|---|---|---|
| EP | 2 614 077 | 8/2016 | |
| EP | 3 311 832 | 4/2018 | |
| JP | 2004-113062 | 4/2004 | |
| WO | WO 86/04356 | 7/1986 | |
| WO | WO 92/10591 | 6/1992 | |
| WO | WO 92/15671 | 9/1992 | |
| WO | WO 01/091625 | 12/2001 | |
| WO | WO 02/088334 | 11/2002 | |
| WO | WO-2004101790 A1 * | 11/2004 | ........... C07K 1/1136 |
| WO | WO 05/084716 | 9/2005 | |
| WO | WO 06/029879 | 3/2006 | |
| WO | WO 08/057437 | 5/2008 | |
| WO | WO 09/091826 | 7/2009 | |
| WO | WO 09/117117 | 9/2009 | |
| WO | WO 2009/111729 A1 | 9/2009 | |
| WO | WO 10/025177 | 3/2010 | |
| WO | WO 12/054825 | 4/2012 | |
| WO | WO 12/082841 | 6/2012 | |
| WO | WO 12/138475 | 10/2012 | |
| WO | WO 13/039889 | 3/2013 | |
| WO | WO 2013/088446 | 6/2013 | |
| WO | WO 2013/154760 | 10/2013 | |
| WO | WO 13/177247 | 11/2013 | |
| WO | WO 14/011984 | 1/2014 | |
| WO | WO 14/031687 | 2/2014 | |
| WO | WO 14/043441 | 3/2014 | |
| WO | WO 14/055771 | 4/2014 | |
| WO | WO 14/068388 | 5/2014 | |
| WO | WO 14/100615 | 6/2014 | |
| WO | WO 14/127261 | 8/2014 | |
| WO | WO 15/057834 | 4/2015 | |
| WO | WO 15/057852 | 4/2015 | |
| WO | WO 15/164594 | 10/2015 | |
| WO | WO 16/025322 | 2/2016 | |
| WO | WO 16/098078 | 6/2016 | |
| WO | WO 16/102965 | 6/2016 | |
| WO | WO 16/054520 | 7/2016 | |
| WO | WO 16/149665 | 9/2016 | |
| WO | WO 16/168766 | 10/2016 | |
| WO | WO 16/168769 | 10/2016 | |
| WO | WO 16/201300 | 12/2016 | |
| WO | WO 16/210447 | 12/2016 | |
| WO | WO 17/029511 | 2/2017 | |
| WO | WO 17/029512 | 2/2017 | |
| WO | WO 17/068360 | 4/2017 | |
| WO | WO 17/068361 | 4/2017 | |
| WO | WO 17/137758 | 8/2017 | |
| WO | WO 17/137759 | 8/2017 | |
| WO | WO 17/143094 | 8/2017 | |
| WO | WO 17/143150 | 8/2017 | |
| WO | WO 17/165245 | 9/2017 | |
| WO | WO 17/165571 | 9/2017 | |
| WO | WO 17/177149 | 10/2017 | |
| WO | WO 17/180587 | 10/2017 | |
| WO | WO 17/216561 | 12/2017 | |
| WO | WO 17/216562 | 12/2017 | |
| WO | WO 18/013797 | 1/2018 | |
| WO | WO 18/111763 | 6/2018 | |
| WO | WO 18/111834 | 6/2018 | |
| WO | WO 18/115146 | 6/2018 | |
| WO | WO 18/152451 | 8/2018 | |
| WO | WO 18/160622 | 9/2018 | |
| WO | WO 2019/060425 A1 | 3/2019 | |
| WO | WO 2019/090215 A2 | 5/2019 | |
| WO | WO 2019/144091 | 7/2019 | |
| WO | WO 19/165237 | 8/2019 | |
| WO | WO 2019/156795 A1 | 8/2019 | |
| WO | WO 2020/033129 | 2/2020 | |
| WO | WO 2020/033272 A1 | 2/2020 | |
| WO | WO 2021/158523 | 8/2021 | |
| WO | WO 2021/158534 | 8/2021 | |
| WO | WO 2021/178887 | 9/2021 | |
| WO | WO 2022/026706 | 2/2022 | |
| WO | WO 2024/086563 | 4/2024 | |

OTHER PUBLICATIONS

Abken, H., et al., Tuning tumor-specific T-cell activation: a matter of costimulation? Trends in Immunology vol. 23 No. 5 May 2002: 240-45.

Abstracts for the 26th Annual Scientific Meeting of the Society for Immunotherapy of Cancer (SITC), J Immunother., vol. 34, No. 9, Nov.-Dec. 2011 (62 pp.).

Airenne et al., Recombinant avidin and avidin-fusion proteins , Biomolecular Engineering16 (1999) 87- 92.

Alcover et al., A soluble form of the human CD8 alpha chain expressed in the baculovirus system: Biochemical characterization and binding to MHC Class I , Molecular Immunology, vol. 30, No. 1, pp. 55-67, 1993.

Alexander et al., Indoleamine 2,3-Dioxygenase Expression in Transplanted NOD Islets Prolongs Graft Survival After Adoptive Transfer of Diabetogenic Splenocytes, Diabetes2002, vol. 51 pp. 356-365.

Alonso-Camino et al. CARbodies: Human Antibodies Against Cell Surface Tumor Antigens Selected From Repertoires Displayed on T Cell Chimeric Antigen Receptors. (2013) Mol Ther Nucl Acids 2, e93 (11 pages).

Altenschmidt, U. et al. Adoptive transfer of in vitro-targeted, activated T lymphocytes results in total tumor regression, J. Immunol. (1997); 159:5509-15.

Altenschmidt, U., et al., Specific cytotoxic T lymphocytes in gene therapy, J. Mol. Med. (1997); 75, 259-266.

Altschul et al., “Local Alignment Statistics, [27] Multiple Alignment and Phylogenetic Trees,” Methods in Enzymology (1996) 266:460-480.

Altschul, S. et al., Basic local alignment search tool, J. Mol. Bio., 1990, 215, 403-410.

Altvater, B., et al., 284 (CD244) Signaling by Recombinant Antigen-specific Chimeric Receptors Costimulates Natural Killer Cell Activation to Leukemia and Neuroblastoma Cells , Clin Cancer Res 2009; 15(15) Aug. 1, 2009: 4857-66.

Alvarez-Vallina, L. et al., Antigen-specific targeting of CD28-mediated T cell co-stimulation using chimeric single-chain antibody variable fragment-CD28 receptors, Eur. J. Immunol, 1996, 26, 2304-2309.

Amin et al., The Eighth Edition AJCC Cancer Staging Manual: Continuing to Build a Bridge From a Population-Based to a More Personalized Approach to Cancer Staging, CA Cancer J Clin (2017) vol. 67, No. 2, pp. 93-99.

An et al., IgG2m4, an engineered antibody isotype with reduced Fc function, mAbs 2009, Landes Bioscience, 1:6, 572-579.

Ang et al., Generating a Chimeric Antigen Receptor To Redirect T-Cell Specificity after Infusion , Molecular Therapy vol. 19, Supplement 1, May 2011, S137-S138.

Annesley et al., Nov. 13, 2019, Novel CD19t T-antigen presenting cells expand CD19 Car T cells in vivo, Blood, 134(Suppl 1):223.

Arch, R, et al., 4-1BB and Ox40 Are Members of a Tumor Necrosis Factor (TNF)-Nerve Growth Factor Receptor Subfamily That Bind TNF Receptor-Associated Factors and Activate Nuclear Factor kB, Molecular And Cellular Biology (1998); 558-565.

Aruffo, A, et al., Molecular cloning of a CD28 cDNA by a high-efficiency COS cell expression system, Proc. Nati. Acad. Sci. USA (1987); 84: 8573-8577.

(56) References Cited

OTHER PUBLICATIONS

Baba et al., N-Linked Carbohydrate on Human Leukocyte Antigen-C and Recognition by Natural Killer Cell Inhibitory Receptors , Human Immunology 61, 1202-1218 (2000).
Baiu et al. (Published online Jul. 26, 2017) Targeted Molecular Radiotherapy of Pediatric Solid Tumors Using a Radioiodinated Alkyl-Phospholipid Ether Analog. J Nucl Med 2018; 59: 244-250.
Baniyash et al., Dec. 5, 1988, The T Cell Antigen Receptor Zeta Chain Is Tyrosine Phosphorylated open Activation The Journal of Biological Chemistry, 263(34):18225-18230.
Barber, et al., Chimeric NKG2D Receptor-Expressing T Cells as an Immunotherapy for Multiple Myeloma, Exp Hematol. (Oct. 2008); 36(10):1318-28.
Barocas et al., A population-based study of renal cell carcinoma and prostate cancer in the same patients, BJU International, (2006) 97(1): 33-36.
Barrett et al., Chimeric Antigen Receptor Therapy for Cancer Annual Review of Medicine vol. 65: 333-347 (2014).
Bauer et al., Activation of NK Cells and T Cells by NKG2D, a Receptor for Stress-Inducible MICA, Science 1999, vol. 285 pp. 727-729.
Bauer, A, et al., Differential signal transduction via T-cell receptor CD3'2, CD3C-,v,and CD3'q2 isoforms, Proc. Nati. Acad. Sci. USA (1991); 88: 3842-3846.
Baum et al. Retrovirus vectors: toward the plentivirus? (2006) Molecular Therapy: The Journal of the American Society of Gene Therapy. 13:1050-1063.
Becker, M. L. B., et al., Expression of a hybrid immunoglobulin-T cell receptor protein in transgenic mice, Cell (1989); 58:911-921.
Bedzyk, WD et al., Active site structure and antigen binding properties of idiotypically cross-reactive anti-fluorescein monoclonal antibodies, J Biol Chem., 1990, 265, 133-138.
Bejcek, B, et al., Development and Characterization of Three Recombinant Single Chain Antibody Fragments (scFvs) Directed against the CD19 Antigen1, Cancer Research55, (1995); 2346-2351.
Berg et al., Section 3.2 Primary Structure: Amino Acids Are Linked by Peptide Bonds to Form Polypeptide Chains Biochemistry. 5th Ed. New York. W.H. Freeman; 2002, pp. 1-16.
Berger et al., Feb. 2015, Safety of targeting ROR1 in primates with chimeric antigen receptor modified T cells, Cancer Immunology Research, 3(2):206-216.
Berger, C., et al., Analysis of trans gene-specific immune responses that limit the in vivopersistence of adoptively transferred HSV-TK-modified donor T cells after allogeneic hematopoietic cell transplantation. Blood, 2006. 107(6): p. 2294-302.
Bio-Rad 2016, The T Cell Marker, CD3 Antigen and Antibodies, retrieved on May 4, 2024 from the Internet: <URL: https://www.bio-rad-antibodies.com/static/2016/innate/the-t-cell-marker-cd3-antigen-and-antibodies.pdf>, 5 pp.
Bluemel, C., et al., Epitope distance to the target cell membrane and antigen size determine the potency of T cell-mediated lysis by BiTE antibodies specific for a large melanoma surface antigen. Cancer Immunol Immunother (2010); 59(8): 1197-209.
Boder et al., Directed evolution of antibody fragments with monovalent femtomolar antigen-binding affinity, PNAS (Sep. 26, 2000) vol. 97, No. 20, pp. 10701-10705.
Bolhuis, R. L. et al. Preparation for a phase I/II study using autologous gene modified T lymphocytes for treatment of metastatic renal cancer patients., Adv. Exp. Med. Biol. (1998); 451:547-55.
Boomer et al., Cutting Edge: A Double-Mutant Knockin of the CD28 YMNM and PYAP Motifs Reveals a Critical Role for the YMNM Motif in Regulation of T Cell Proliferation andBcl-x L Expression The Journal of Immunology. 2014; 192, pp. 3465-3469.
Boomer, J, et al.,. An Enigmatic Tail of CD28 Signaling, Washington University School of Medicine (2010); 1-20.
Boursier et al., Evidence for an Extended Structure of the T-cell Co-receptor CD8α as Deduced from the Hydrodynamic Properties of Soluble Forms of the Extracellular Region*, The Journal of Biological Chemistry 1993, vol. 268, No. 3, Issue of Jan. 25, pp. 2013-2020.
Brennan et al., Carbohydrate Recognition by a Natural Killer Cell Receptor, Ly-49C*, The Journal of Biological Chemistry 1995, vol. 270, No. 17, Issue of Apr. 28, pp. 9691-9694.
Brentjens et al., CD19-targeted T cells rapidly induce molecular remissions in adults with chemotherapy-refractory acute lymphoblastic leukemia. Sci Transl Med. 2013 5(177)ra38 (11 pages).
Brentjens, et al., Eradication of systemic B-cell tumors by genetically targeted human T lymphocytes co-stimulated by CD80 and interleukin-15, Nat. Med. (2003); 9: 279-286.
Bruhns et al., Differential Roles of N- and C-Terminal Immunoreceptor Tyrosine-Based Inhibition Motifs During Inhibition of Cell Activation by Killer Cell Inhibitory Receptors, The Journal of Immunology 1999; 162:3168-3175.
Bukczynski et al., Costimulatory ligand 4-1 BBL (CD137L) as an efficient adjuvant of human antiviral cytotoxic T cell responses, Proc. Natl. Acad. Sci. USA, 2004, 101:1291-1296.
Cambier, et al., Antigen and Fc receptor signaling. The awesome power of the immunoreceptor tyrosine-based activation motif (ITAM), J Immunol. (Oct. 1, 1995); 155(7):3281-5.
Camerini, D, et al,. The T cell activation antigen CD27 is a member of the nerve growth factor/tumor necrosis factor receptor gene family, The Journal of Immunology (1991);3165-3169.
Cameron, B.J., et al., Identification of a Titin-Derived HLA-A1-Presented Peptide as a Cross-Reactive Target for Engineered MAGE A3-Directed T Cells, Sci Transl Med (Aug. 7, 2013); 5(197): 197ra103 (11 pages).
Canfield et al., The Binding Affinity of Human IgG for its High Affinity Fc Receptor Is Determined by Multiple Amino Acids in the CH2 Domain and Is Modulated by the Hinge Region, J. Exp. Med. 1991, vol. 173 pp. 1483-1491.
Cannons et al., 4-1BB ligand induces cell division, sustains survival, and enhances effector function of CD4 and CD8 T cells with similar efficacy, J Immunol. Aug. 2001, 167(3): 1313-1324.
Carlens et al. Ex vivo T lymphocyte expansion for retroviral transduction: influence of serum-free media on variations in cell expansion rates and lymphocyte subset distribution. (2000) Exp Hematol 28(10): 1137-46.
Cartellieri, M. et al., Chimeric antigen receptor-engineered T cells for immunotherapy of cancer, J. Biomedicine and Biotechnology, 2010, Article ID 956304, 13 pages.
Caruana et al., 2013, Boosting in vivo CAR-redirected virus-specific CTLs with universal-artificial antigen presenting cells, Blood, 122(21):4204.
Cavalieri et al. Human T lymphocytes transduced by lentiviral vectors in the absence of TCR activation maintain an intact immune competence. (2003) Blood. 102(2): 497-505.
Chalupny et al., T-cell activation molecule 4-1BB binds to extracellular matrix proteins, Proc. Natl. Acad. Sci., USA, 89: 103360-10364 (Nov. 1992).
Chang et al., A Chimeric Receptor with NKG2D Specificity Enhances Natural Killer Cell Activation and Killing of Tumor Cells , Cancer Res 2013;73:1777-1786. Published online Jan. 9, 2013.
Cheadle et al, Chimeric antigen receptors for T-cell based therapy Methods Mol Biol. 2012; 907:645-66.
Chen et al. Fusion protein linkers: property, design and functionality, Adv Drug Deliv Rev.(2013); 65: 1357-1369 (Epub Sep. 29, 2012).
Cheng et al., Mar. 26, 2004, Hapten-directed targeting to single-chain antibody receptors, Cancer Gene Therapy, 11(5):380-388.
Cho C. Rapid identification of cytokine release syndrome after haploidentical PBSC transplantation and successful therapy with tocilizumab. Bone Marrow Transplant. Dec. 2016;51(12):1620-1621, Epub Sep. 26, 2016.
Cho et al., Macromolecular versus small-molecule therapeutics: drug discovery, development and clinical considerations TIBTECH, vol. 14, May 1996, pp. 153-158.
Chothia et al., Dec. 1989, Conformations of immunoglobulin hypervariable regions, Nature, 342:877-883.

(56) References Cited

OTHER PUBLICATIONS

Cohen et al. Recognition of fresh human tumor by human peripheral blood lymphocytes transduced with a bicistronic retroviral vector encoding a murine anti-p53 TCR (2005) J Immunol. 175:5799-5808.
Colcher, D. et al. In vivo tumor targeting of a recombinant single-chain antigen-binding protein., J. Nat. Cancer Inst. (1990); 82:1191-1197.
Cole et al., The molecular determinants of CD8 co-receptor function, 2012, Immunology, 137, 139-148.
Common Terminology Criteria for Adverse Events (CTCAE), National Cancer Institute Common Toxicity Criteria version 4.03 (NCI-CTCAE v4.03 (2010) (196 pages).
Cooper et al. T-cell clones can be rendered specific for CD19: toward the selective augmentation of the graft-versus-B-lineage leukemia effect (2003) Blood. 101(4): 1637-1644.
Cooper et al., Enhanced antilymphoma efficacy of CD19-redirected influenza MP1-specific CTLs by cotransfer of T cells modified to present influenza MP1, Blood 2005, vol. 105 No. 4 pp. 1622-1631.
Cordaro, T. A et al. Tumor size at the time of adoptive transfer determines whether tumor rejection occurs, Eur. J. Immunol. (2000); 30: 1297-1307.
Croft, M., The role of TNF superfamily members in T-cell function and diseases Nature Reviews, Immunology, vol. 9, Apr. 2009, pp. 271-285.
Dall, Peter et al., In vivo cervical cancer growth inhibition by genetically engineered cytotoxic T cells. Cancer Immunol. Immunother. (Jan. 2005); 54(1):51-60.
Darcy, P. K. et al., Expression in cytotoxic T lymphocytes of a single-chain anti-carcinoembryonicantigen antibody. Redirected Fas ligand-mediated lysis of colon carcinoma, Eur. J. Immunol. (1998); 28:1663-72.
Davila M. L. et al: Efficacy and toxicity management of 19-28z CAR T cell therapy in B cell acute lymphoblastic leukemia Sci Transl Med. Feb. 19, 2014;6(224):224-25.
Davila Marco L. et al: CD19-Targeted T Cells for Hematologic Malignancies •Clinical Experience to Date , Cancer Journal, vol. 21, No. 6, Jan. 1, 2015 (Jan. 1, 2015), pp. 470-474.
Debelouchina et al., A molecular engineering toolbox for the structural biologist Quarterly Reviews of Biophysics, 2017, 50, e7, pp. 1-41.
Deming et al., Oct. 6, 2014, Phospholipid ether analogs for the detection of colorectal tumors. PLoS One, 9(10):e109668.
Deng et al., 2019, Antitumor activity of NKG2D CAR-T cells against human colorectal cancer cells in vitro and in vivo, Am J. Cancer Res, 9(5):945-958.
Diefenbach et al., The innate immune response to tumors and its role in the induction of T-cell immunity, Immunological Reviews 2002, vol. 188: 9-21.
Dissanayake et al., Mar. 19, 2014, Peptide-pulsed dendritic cells have superior ability to induce immune-mediated tissue destruction compared to peptide with adjuvant. PLoS One, 9(3):e92380, 10 pp.
Dotti, et al. Design and development of therapies using chimeric antigen receptor-expressing T cells. Immun Rev (Jan. 2014); 257(1): 107-126.
Dubrovska, A., et al., A chemically induced vaccine strategy for prostate cancer, ACS Chem Biol (2011); 6(11): 1223-31.
Duncan et al., Localization of the binding site for the human high-affinity Fc receptor onlg G, Nature 1998, vol. 332 pp. 563-564.
Elsaid et al., Nov. 2018, Enhanced Radiosensitivity in Solid Tumors using a Tumor-selective Alkyl Phospholipid Ether Analog. Mol Cancer Ther., 17(11):2320-2328.
Ertl, H. C. et al., Considerations for the clinical application of chimeric antigen receptor T cells: observations from a recombinant DNA advisory committee symposium held Jun. 15, 2010, Cancer Res., 2011, 71, 3175-3181.
Eshhar, et al, Design of Cytotoxic T Lymphocytes with Antibody-Type Specificity against Tumor Cells Using Chimeric TcR, Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., Functional expression of chimeric receptor genes in human T cells, J. Immunol. Meth. (2001); 248: 67-76.
Fang et al., Jul. 17, 2013, Lipid-insertion enables targeting functionalization of erythrocyte membrane-cloaked nanoparticles, Nanoscale, 5(19):8884-8888.
Fedorov VD, et al., PD-1- and CTLA-4-based inhibitory chimeric antigen receptors (iCARs) divert off-target immunotherapy responses, Sci Transl Med. (Dec. 11, 2013);5(215):215ra172 (12 pages).
Feng et al., Convergence on a Distinctive Assembly Mechanism by Unrelated Families of Activating Immune Receptors , Immunity, vol. 22, 427-438, Apr. 2005.
Feng et al., The Assembly of Diverse Immune Receptors Is Focused on a Polar Membrane-Embedded Interaction Site , 2006. PLOS Biol 4(5):e142.
Ferrone, S., et al., How much longer will tumor cells fool the immune system, Immunol. Today (2000); 21: 70-72.
Figini, M, et al., Conversion of murine antibodies to human antibodies and their optimization for ovarian cancer therapy targeted to the folate receptor, Cancer ImmunolImmunother (Apr. 2009); 58(4):531-46 (Epub Aug. 15, 2008).
Foell et al., CD137-mediated T cell co-stimulation terminates existing autoimmune disease in SLE-prone NZB/NZW F1 mice., Ann N Y Acad Sci. Apr. 2003; 987:230-5.
Frecha et al. Advances in the field of lentivector-based transduction of T and B lymphocytes for gene therapy (2010) Molecular Therapy: The Journal of the American Society of Gene Therapy. 18:1748-1757.
Frost et al., In Vitro Evaluation of Avidin Antibody Pretargeting Using 211At-Labeled andBiotinylated Poly-L-Lysine as Effector Molecule*, Cancer 2010, Cancer Therapy With Antibodies and Immunoconjugates, Supplement to Cancer, pp. 1101-1110.
Fujita, K. et al., Prolonged disease-free period in patients with advanced epithelial ovarian cancer after adoptive transfer of tumor-infiltrating lymphocytes. Clin. Cancer Res., 1995, 1, 501-507.
Gargalionis et al, The molecular rationale of Src inhibition in colorectal carcinomas, Int. J.Cancer, 134:2019-2029 (2013).
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.
Gilboa, E., How tumors escape immune destruction and what we can do about it, Cancer Immunol. Immunother. (1999); 48: 382-385.
Gilham et al., CAR-T cells and solid tumors: tuning T cells to challenge an inveterate foe, Trends in Molecular Medicine (2012); 18(7): 377-384 (Epub May 19, 2012).
Gilham et al., Primary polyclonal human T lymphocytes targeted to carcino-embryonicantigens and neural cell adhesion molecule tumor antigens by CD3zeta-based chimeric immune receptors, J. Immunother, (Mar.-Apr. 2002); 25 (2): 139-151.
Gillies, S.D. et al., Targeting Human Cytotoxic T Lymphocytes to Kill Heterologous Epidermal Growth Factor Receptor-Bearing Tumor Cells, The Journal of Immunology (1991); 146(3): 1067-1071.
Gong, M. C., et al., Prostate-specific membrane antigen (PSMA)-specific monoclonal antibodies in the treatment of prostate and other cancers, Cancer Metastasis Rev. (1999); 18: 483-490.
Goverman, J. et al., Chimeric immunoglobulin-T cell receptor proteins form functional receptors: implications for T cell receptor complex formation and activation, Cell (1990); 60:929-939.
Greenfield, E. A, Nguyen, K. A & Kuchroo, V. K. CD28/B7 co-stimulation: a review. Crit. Rev. Immunol. 18, 389-41 8 (1998).
Griffiths et al., The Nature of DNA Modern Genetic Analysis. New York: W.H. Freeman; 1999, pp. 1-11.
Grosenbach et al., A recombinant vector expressing transgenes for four T-cell costimulatory molecules (OX40L, B7-1, ICAM-1, LFA-3) induces sustained CD4+ and CD8+ T-cell activation, protection from apoptosis, and enhanced cytokine production, Cellular Immunology 222 (2003) 45-57.
Gross et al., Development and study of chimeric immunoglobulin/T cell receptor molecules as functional receptors that endow T cells

(56) References Cited

OTHER PUBLICATIONS with antibody-type specificity, Ph.D. Thesis presented to the Feinberg Graduate School, The Wiezmann Institute of Science, Rehovot, Israel (1990); 1-70.
Gross, G. et al., Endowing T cells with antibody specific using chimeric T cell receptors, Department of Chemical Immunology, FASEB J. (Dec. 1992); 6(15):3370-8.
Gross, G. et al., Expression of immunoglobuling-T-cell receptor chimeric molecules as functional receptors with antibody-type specificity, Proc. Natl. Acad. Sci., 1989, 86, 10024-10028.
Gross, G. et al., Generation of effector T cells expressing chimeric T cell receptor with antibody type-specificity, Transplant. Proc. (1989); 21 (1 Pt 1):127-130.
Grupp et al., Chimeric Antigen Receptor-Modified T Cells for Acute Lymphoid Leukemia, N. Engl. J. Med. (Apr. 18, 2013) 368(16):1509-1518.
Grupp Stephan A.: Advances in T-cell therapy for All, Best Practice & Research Clinical Haematology, vol. 27, No. 3-4, Sep. 1, 2014(Sep. 1, 2014), pp. 222-228.
Gruss et al., Tumor Necrosis Factor Ligand Superfamily: Involvement in the Pathology of Malignant Lymphomas Blood, vol. 85, No. 12, Jun. 15, 1995, pp. 3378-3404.
Guinn et al., 4-1BBL Cooperates with B7-1 and B7-2 in Converting a B Cell Lymphoma Cell Line into a Long-Lasting Antitumor Vaccine, The Journal of Immunology162:5003-5010 (1999).
Habib-Agahi, H., Phan, T.T. and Searle, P.F. Co-stimulation with 4-1BB ligand allows extended T-cell proliferation, synergizes with CD80/CD86 and can reactivate anergic T cells Int. Immunol. 19 (12), 1383-1394 (2007).
Hackett et al. A transposon and transposase system for human application (2010) Molecular Therapy: The Journal of the American Society of Gene Therapy. 18:674-683.
Hanson, H. L. et al. Eradication of established tumors by CD8+ T cell adoptive immunotherapy. Immunity 13, 265-276 (2000).
Harper et al., CTLA-4 and CD28 Activated Lymphocyte Molecules are Closely Related in Both Mouse and Human as to Sequence, Message, Expression, Gene Structure, and Chromosomal Location , The Journal of Immunology, vol. 147, 1037-1044, No. 3, Aug. 1, 1991.
Hatakeyama et al., Transmembrane Signaling of Interleukin 2 Receptor, J. Exp. Med. 1987, vol. 166 pp. 362-375.
Haynes et al., Redirecting Mouse CTL Against Colon Carcinoma: Superior Signaling Efficacy of Single-Chain Variable Domain Chimeras Containing TCR-zeta vs Fcepsilon RI-gamma J Immunol 2001; 166:182-187 (Haynes 2001).
Hege et al., Safety, tumor trafficking and immunogenicity of chimeric antigen receptor (CAR)-T cells specific for TAG-72 in colorectal cancer, Journal for Immunotherapy of Cancer 2017, 5:22.
Hege et al., Systemic T Cell-independent Tumor Immunity after Transplantation of Universal Receptor-modified Bone Marrow into SCID Mice , J. Exp. Med. vol. 184 Dec. 1996 pp. 2261-2269.
Herron, J.N., et al., High resolution structures of the Apr. 4, 2020 Fab-fluorescein complex in two solvent systems: effects of solvent on structure and antigen-binding affinity . Biophys J, 1994. 67(6): p. 2167-83.
Heuser, et al., T-cell activation by recombinant immunoreceptors: impact of the intracellular signalling domain on the stability of receptor expression and antigen-specific activation of grafted T-cells, Gene Therapy (2003); 10: 1408-1419.
Hombach et al., T cell activation by recombinant FcεRI γ-chain immune receptors: an extracellular spacer domain impairs antigen-dependent T cell activation but not antigen recognition, Gene Therapy (2000) 7, 1067-1075.
Hombach, et al., Adoptive Immunotherapy with Genetically Engineered T Cells: Modification of the IgG1 Fc 'Spacer' Domain in the Extracellular Moiety of Chimeric Antigen Receptors Avoids 'Off-Target' Activation and Unintended Initiation of an Innate Immune Response, Gene Ther. (Oct. 2010); 17(10):1206-13.
Honegger et al., A mutation designed to alter crystal packing permits structural analysis of a tight-binding fluorescein-scFv complex, Protein Science (2005) 14(10), 2537-2549.
Huang, J., et al., Modulation by IL-2 of CD70 and CD27 expression on CD8+ T cells: importance for the therapeutic effectiveness of cell transfer immunotherapy J. Immunol. 176 (12), 7726-7735 (2006).
Hudecek et al. Jun. 15, 2013, Receptor affinity and extracellular domain modifications affect tumor recognition by ROR1-specific chimeric antigen receptor T-cells. Clin Cancer Res. 19(12):3153-3164.
Hughes M. S. et al., Transfer of a TCR gene derived from a patient with a marked antitumor response conveys highly active T-cell effector functions. Hum Gene Ther Apr. 2005; 16(4):457-72).
Hunter et al., Inhibition of Fcγ Receptor-Mediated Phagocytosis by a Nonphagocytic FcγReceptor, Blood, vol. 91, No. 5 Mar. 1, 1998: pp. 1762-1768.
Hutchins, B. et al., Site-specific coupling and sterically controlled formation of multimeric antibody fab fragments with unnatural amino acids, J. Mol. Biol., 2011, 406, 595-603.
Hutloff, A. et al., ICOS is an inducible T-cell costimulator structurally and functionally related to CD28, Nature, 1999, 397, 263-266.
Hwu, et al, The Genetic Modification of T Cells for Cancer Therapy: An Overview of Laboratory and Clinical Trials, Cancer Detection and Prevention (1994); 18(1):43-50.
Hyman et al., 2012, Probing oxidative stress: Small molecule fluorescent sensors of metal ions, reactive oxygen species, and thiols. Coordination Chemistry Reviews, 256:2333-2356.
Imai, C. et al., Chimeric receptors with 4-1BB signaling capacity provoke potent cytotoxicity against acute lymphoblastic leukemia, Leukemia, 2004, 18, 676-684.
Imai, K., et al., Comparing Antibody and Small-Molecule Therapies for Cancer; https://www.medscape.com/viewarticle/550008 (26 pages).
Irving, B. A., et al., The cytoplasmic domain of the T cell receptor zeta chain is sufficient to couple to receptor-associated signal transduction pathways Cell (1991); 64:891-901.
Isakov et al., PKC-theta-mediated signal delivery from the TCR/CD28 surface receptors , Frontiers in Immunology, T Cell Biology, Aug. 2012, vol. 3, Article 273, pp. 1-12.
Janeway et al., Appendix I. Immunologists' Toolbox Immunobiology: The Immune System in Health and Disease. 5th ed. New York: Garland Science; 2001 (101 pages).
Janeway et al., The structure of a typical antibody molecule Immunobiology: The Immune System in Health and Disease. 5th Ed. New York: Garland Science; 2001, pp. 1-11.
Jang, I, et al., Human 4-1BB (CD137) Signals Are Mediated by TRAF2 and Activate Nuclear Factor-kB, Biochemical And Biophysical Research Communications (1998);613-620.
Jena et al., Redirecting T-cell specificity by introducing a tumor-specific chimeric antigen Receptor, Blood 2010, vol. 116, No. 7, pp. 1035-1044.
Jensen, M et al. CD20 Is A Molecular Target For scFvFc[zeta] Receptor Redirected T Cells: Implications for Cellular Immunotherapy of CD20+ Malignancy, Biology of Blood and Marrow Transplantation (1998); 4:75-83.
Jensen, M. C., et al., Abstract #98: Targeting Pre-B Acute Lymphoblastic Leukemia With T Cell Clones Engineered To Express A CD19-Specific Chimeric Immunoreceptor, Blood (Nov. 16, 2000); 96(11):26A.
Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.
Johnson et al., 2000, Kabat database and its applications: 30 years after the first variability plot, Nucleic Acids Res., 28(1): 214-218.
Jonnalagadda et al., Chimeric Antigen Receptors With Mutated IgG4 Fc Spacer Avoid Fc Receptor Binding and Improve T Cell Persistence and Antitumor Efficacy, Molecular Therapy 2015, vol. 23, No. 4, pp. 757-768.
Jung et al., Improving in vivo folding and stability of a single-chain Fv antibody fragment by loop grafting, Protein Engineering (1997) vol. 10, No. 8, pp. 956-966.
Jung, S. et al., Selection for improved protein stability by phage display, J. Mol. Biol., 1999, 294, 163-180.

(56) References Cited

OTHER PUBLICATIONS

Kabat et al., 1991, Sequences of Proteins of Immunological Interest, 5th Ed. Public Health Service, National Institutes of Health, Bethesda, Md. (TOC).
Kagoya, Y., et al., Transient stimulation expands superior antitumor T cells for adoptive therapy. JCI Insight, 2017. 2(2): p. e89580 (13 pages).
Kalos et al., T Cells with Chimeric Antigen Receptors Have Potent Antitumor Effects and Can Establish Memory in Patients with Advanced Leukemia, Sci. Transl. Med. (Aug. 10, 2011) 3(95):1-21.
Kandalaft, L. et al., A phase I clinical trial of adoptive transfer of folate receptor-alpha redirected autologous T cells for recurrent ovarian cancer, Journal of Translational Medicine, 2012, 10:157, 10 pages.
Kang, S. et al: Therapeutic uses of anti-interleukin-6 receptor antibody, International Immunology, vol. 27, No. 1, Aug. 20, 2014 (Aug. 20, 2014), pp. 21-29.
Karachaliou et al., Common Co-activation of AXL and CDCP1 in EGFR-mutation-positive Non-small cell Lung Cancer Associated with Poor Prognosis, EBioMedicine (2017) https://doi.org/10/1016/j.ebiom.2018.02.001.
Kariv et al., Analysis of the Site of Interaction of CD28 with Its Counterreceptors CD80 and CD86 and Correlation with Function, 157 J. Immunol.29-38 (1996).
Katz et al., Recognition of HLA-Cw4 but Not HLA-Cw6 by the NK Cell Receptor Killer Celllg-Like Receptor Two-Domain Short Tail No. 4 , J Immunol 2001; 166:7260-7267.
Kennedy, M. et al., Optical imaging of metastatic tumors using a folate-targeted fluorescent probe, J. Biomed. Opt., 2003, 8, 636-641.
Kim el al. Redirection of Genetically Engineered CAR•T Cells Using Bifunctional Small Molecules, Journal of the American Chemical Society (Feb. 18, 2015) vol. 137, No. 8, pp. 2832-2835, with 8 page supporting document.
Kim et al., NMR Structural Studies of Interactions of a Small, Nonpeptidyl Tpo Mimic with the Thrombopoietin Receptor Extracellular Juxtamembrane and Transmembrane Domains, J Biol Chem (2007) 282(19):14253-14261.
Kim et al., Protein conjugation with genetically encoded unnatural amino acids, Curr OpinChem Biol (2013); 17:412-419 (Epub May 9, 2013).
Kim et al., Therapeutic Potential of 4-1BB (CD137) As a Regulator for Effector CD8+ T Cells, Journal of Hematotherapy & Stem Cell Research (2001) 10:441-449.
Kintzing et al., Emerging Strategies for Developing Next-Generation Protein Therapeutics for Cancer Treatment Trends in Pharmacological Sciences, vol. 37, No. 12, Dec. 2016, pp. 993-1008.
Klotz et al., Macromolecule-Small Molecule Interactions. Strong Binding by Intramolecularly Cross-Linked Polylysine Biochemistry. vol. 10, No. 6, Mar. 16, 1971, pp. 923-926.
Kochenderfer et al., Construction and pre-clinical evaluation of an anti-CD19 chimeric antigen receptor, Journal of Immunotherapy (2009); 32(7): 689-702.
Kochenderfer et al., Treating B-cell cancer with T cells expressing anti-CD19chimeric antigen receptors 2013, Nature Reviews Clinical Oncology, 10, 267-276 (2013).
Kochenderfer, J. et al., B-cell depletion and remissions of malignancy along with cytokine-associated toxicity in a clinical trial of anti-CD19 chimeric-antigen-receptor-transduced T cells, Blood, 2012, 119, 2709-2720.
Kochenderfer, J. et al., Eradication of B-lineage cells and regression of lymphoma in a patient treated with autologous T cells genetically engineered to recognize CD19, Blood, 2010, 116, 4099-4102.
Kolmar, H. et al., Alternative binding proteins: biological activity and therapeutic potential of cystine-knot miniproteins, The FEBS Journal, 2008, 275, 26684-26690.
Kozer et al., 2011, Evidence for extended YFP-EGFR dimers in the absencse of ligand on the surface of living cells, Physical Biology, 8:066002, 12 pp.
Kranz et al., Partial elucidation of an anti-hapten repertoire in BALB/c mice: comparative characterization of several monoclonal antiFLuorescyl antibodies, Mol Immunol (1981) 18(10), 889-898.
Krause, A., et al., Genetic approaches to sustain the function of tumor-specific T-lymphocytes, Mol. Ther. (2000); 1 (S260): 713.
Kularatne, S.A. et al., Prostate-specific membrane antigen targeted imaging and therapy of prostate cancer using a PSMA inhibitor as a homing ligand, Mol. Pharm., 2009, 6,780-789.
Kunik et al., Jun. 6, 2012, Paratome: an online tool for systematic identiifcation of antigen-binding regions in antibodies based on sequence or structure, Nucl Acids Res. 40:W521-W524.
Kuwana, Y. et al., Expression of chimeric receptor composed of immunoglobulin-derived V regions and T-cell receptor-derived C regions, Biochem. Biophys. Res. Comm. (1987); 149:960-968.
Kwon, B, et al., cDNA sequences of two inducible T-cell genes, cDNA sequences of two inducible T-cell genes (1989); 86: 1963-1967.
Kwon, B, et al., Expression Characteristics of Two Potential T Cell Mediator Genes, Cellular Immunology (1989); 414-422.
Lafage-Pochitaloff M, Costello R, Couez D, Simonetti J, Mannoni P, Mawas C, Olive D. Human CD28 and CTLA-4 lg superfamily genes are located on chromosome 2 at bands q33-q34 Immunogenetics 1190;31(3):198-201.
Lamers et al., Immune responses to transgene and retroviral vector in patients treated withex vivo-engineered T cells, Blood (2011) 117(1): 72-82.
Lamers, C. et al., Treatment of Metastatic Renal Cell Carcinoma With Autologous T-Lymphocytes|Genetically Retargeted Against Carbonic Anhydrase IX: First Clinical Experience, J. Clin. Oncol., 2006, 24, e20-22.
Laroche et al., Characterization of a Recombinant Single-chain Molecule Comprising the Variable Domains of a Monoclonal Antibody Specific for Human Fibrin Fragment D-dimer*, The Journal of Biological Chemistry 1991, vol. 266, No. 25, Issue of Sep. 5, pp. 16343-16349.
Latza, U. et al., The human OX40 homolog: cDNA structure, expression and chromosomal assignment of the ACT35 antigen, Eur. J. Immunol., 1994, 24, 677-683.
Lee et al., Current concepts in the diagnosis and management of cytokine release syndrome Blood. Jul. 10, 2014;124(2):188-95. doi: 10.1182/blood-2014-05-552729. Epub May 29, 2014, with errata.
Lee et al., Jan. 15, 2019, Use of a single CAR T cell and several bispecific adapters facilitates eradication of multiple antigenically different solid tumors, Cancer Research, 79(2):387-396.
Lee, D, et al., 4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells, PLoS One (2013); 8: 1-11.
Lefranc et al., 2003, IMGT unique numbering for immunoglobulin and T cell receptor variable domains and Ig superfamily V-like domains, Dev Comp Immunol. 27:55-77.
Li et al., Jan. 2020, CAIZ-specific CAR-T cells and sunitinib show syngeristic effects against metastatic renal cancer models, J Immunother, 43(1):16-28.
Liebowitz, D. N., Lee, K. P. & June, C. H. Co-stimulatory approaches to adoptive immunotherapy. Curr. Opin. Oncol. 10, 533-541 (1998).
Lin et al., Transglutaminase-catalyzed site-specific conjugation of small-molecule probes to proteins in vitro and on the surface of living cells, J. Am. Chem. Soc. (2006);128:4542-4543.
Linenberger, CD33-directed therapy with gemtuzumab ozogamicin in acute myeloid leukemia: progress in understanding cytotoxicity and potential mechanisms of drug resistance , Leukemia (2005) 19, 176-182.
Liou et al., A chimeric mouse-human antibody that retains specificity for HIV gp 120 and mediates the lysis of HIV-infected cells, J Immunol 1989; 143: 3967-3975.
Liu et al., 2012, Phospholipid-Graphene Nanoassembly as a Fluorescence Biosensor for Sensitive Detection of Phospholipase D Activity. Anal. Chem. 84(14):5944-5950.
Lodish et al., Hierarchical Structure of Proteins Molecular Cell Biology. 4th Ed. New York: W.H. Freeman; 2000. pp. 1-25.

(56) References Cited

OTHER PUBLICATIONS

Lohmueller et al., 2018, mSA2 affinity-enhanced biotin-binding CAR T cells for universal tumore targeting, Oncolmmunology, 7(1):e1368604.
Long, A.H., et al., 4-IBB costimulation ameliorates T cell exhaustion induced by tonic signaling of chimeric antigen receptors. Nat Med, 2015. 21(6): p. 581-90.
Love et al., ITAM-mediated Signaling by the T-Cell Antigen Receptor, Cold Spring HarbPerspect Biol 2010;2:a002485.
Lowin-Kropf et al., Cytoskeletal Polarization of T Cells Is Regulated by an Immunoreceptor Tyrosine-based Activation Motif-dependent Mechanism, The Journal of Cell Biology 1998, vol. 140, No. 4, pp. 861-871.
Lu et al., Mar. 2019, Preclinical Evaluation of Bispecific Adaptor Molecule Controlled Folate Receptor CAR-T Cell Therapy with Special Focus on Pediatric Malignancies. Frontiers in Oncology, 9(51):1-20.
Lu et al., Preclinical pharmacokinetics, tissue distribution, and antitumor activity of afolate-hapten conjugate-targeted immunotheraphy in hapten-immunized mice, Molecular Cancer Therapeutics, 2006, 5, 3258-3267.
Lu, Y. et al., Folate-targeted dinitrophenyl hapten immunotherapy: effect of linkerchemistry on antitumor activity and allergic potential, Mol. Pharm., 2007, 695-706.
Lueders et al., The Long Terminal Repeat of an Endogenous Intracisternal A—ParticleGene Functions as a Promoter When Introduced into Eucaryotic Cells by Transfection Molecular and Cellular Biology, vol. 4, No. 10, Oct. 1984, pp. 2128-2135.
Lustgarten, J., et al., Specific Elimination of IgE Production Using T Cell Lines Expressing Chimeric T Cell Receptor Genes, European Journal of Immunology (1995); 25(10):2985-2991.
Ma et al., Jul. 12, 2019, Enhanced CAR-T cell activity against solid tumors by vaccine boosting through the chimeric receptor, Science, 365(6449):162-168.
Ma et al., Versatile strategy for controlling the specificity and activity of engineered T cells, Proc. Nat. Acad. Sci. U.S.A (Jan. 12, 2016) vol. 113, No. 4, pp. 450-458.
Ma, Q. et al., Carcinoembryonic antigen-immunoglobulin Fc fusion protein (CEA-Fc) for identification and activation of anti-CEA immunoglobulin-T-cell receptor-modified T cells, representative of a new class of Ig fusion proteins, Cancer Gene Therapy (2004); 11: 297-306.
Ma, Q., et al., Genetically engineered T cells as adoptive immunotherapy of cancer, Cancer Chemother Biol Response Modif (2002); 20: 315-41.
Maeda et al., Tumor vascular permeability and the EPR effect in macromolecular therapeutics: a review, Journal of Controlled Release 65 (2000), pp. 271-284 (14 pages).
Maher, et al., Human T-lymphocyte cytotoxicity and proliferation directed by a single chimeric TCRzeta/CD28 receptor, Nature Biotechnology (2002); 20: 70-75.
Makabe et al., Jan. 11, 2008, Thermodynamic consequences of mutations in Vernier zone residues of a humanized anti-human epidermal growth factor receptor murine antibody, 528, Journal of Biological Chemistry, 283(2):1156-1166.
Marincola, F. M., et al., Escape of human solid tumors from T cell recognition: molecular mechanisms and functional significance, Adv. Immunol. (2000); 74: 181-273.
Martin et al., Dec. 1989, Modeling antibody hypervariable loops: a combined algorithm, Proc Natl Acad Sci (USA), 86:9268-9272.
Maude Shannon L. et al. Chimeric Antigen Receptor T Cells for Sustained Remissions in Leukemia N Engl J Med. Oct. 16, 2014;371(16):1507-17.
Maude Shannon L. et al. Managing Cytokine Release Syndrome Associated With Novel T Cell-Engaging Therapies Cancer J. Mar.-Apr. 2014;20(2):119-22.
Maus et al., Ex vivo expansion of polyclonal and antigen-specific cytotoxic T lymphocytes by artificial APCs expressing ligands for the T-cell receptor, CD28 and 4-1BB, Nature Biotechnology, Nature Publishing Group, New York, NY, US, vol. 20, No. 2, Feb. 1, 2002, pp. 143-148.
Maus, M.V., et al., T cells expressing chimeric antigen receptors can cause anaphylaxis in humans. Cancer Immunol Res, 2013. 1(1): p. 26-31.
McEnaney et al., Jul. 20, 2012, Antibody-recruiting molecules: an emerging paradigm for engaging immune function in treating human disease. ACS Chem Biol. 7(7):1139-1151.
Mcguinness RP, et al., Anti-tumor activity of human T cells expressing the CC49-zeta chimeric immune receptor, Hum Gene Ther. (Jan. 20, 1999); 10(2):165-73.
Medstrand et al., Long Terminal Repeats Are Used as Alternative Promoters for the Endothelin B Receptor and Apolipoprotein C-I Genes in Humans, The Journal of Biological Chemistry, vol. 276, No. 3, Issue of Jan. 19, pp. 1896-1903, 2001.
Melero, I, et al., Amplification of tumor immunity by gene transfer of the co-stimulatory 4-1BB ligand: synergy with the CD28 co-stimulatory pathway, Bristol-Myers Squibb Pharmaceutical Research Institute (1998); 1116-1121.
Melief, C. J. et al., Strategies for immunotherapy of cancer, Adv. Immunol. (2000); 75:235-282.
Mooney et al., Concise Review: Neural Stem Cell-Mediated Targeted Cancer Therapies Stem Cells Translational Medicine, 2018, pp. 740-747.
Moore et al., Characterisation of salmon and trout CD8a and CD8B, Molecular Immunology 42 (2005) 1225-1234.
Moretta et al., Activating Receptors and Coreceptors Involved in Human Natural Killer Cell-Mediated Cytolysis, Annu. Rev. Immunol. 2001. 19:197-223.
Morgan RA, et al., Cancer regression in patients after transfer of genetically engineered lymphocytes, Science (Oct. 6, 2006); 314(5796): 126-9.
Morrison, C, CAR-T Field Booms as Next-Generation Platforms Attract Big Players, Nature Biotechnology (Jun. 2015); 33: 571-72.
Muller T, et al., Expression of a CD20-specific chimeric antigen receptor enhances cytotoxic activity of NK cells and overcomes NK-resistance of lymphoma and leukemia cells, Cancer Immunol. Immunother. (2008); 57: 411-423.
Mungra et al., Targeted human cytolytic fusion proteins at the cutting edge: harnessing the apoptosis-inducing properties of human enzymes for the selective elimination of tumor cells Oncotarget, vol. 10, No. 8, 2019, pp. 897-915.
Munn et al., Role of Low-Affinity Fc Receptors in Antibody-dependent Tumor Cell Phagocytosis by Human Monocyte-derived Macrophages, Cancer Research 51, 1117-1123, Feb. 15, 1991.
Nam, K, et al., Cross-Linking of 4-1BB Activates TCR-Signaling Pathways in CD8 T Lymphocytes1, The Journal of Immunology; 1898-1905.
National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 fromhttp://www.cancer.gov/cancertopics/research-updates/2013/CAR-T-Cells.
Nelson, Aaron L., Antibody fragments, mAbs 2010, Landes Bioscience, vol. 2, Issue 1, pp. 77-83.
Nieba, L. et al., Disrupting the hydrophobic patches at the antibody variable/constant domain interface: improved in vivo folding and physical characterization of an engineered scFv fragment, Protein Eng., 1997, 10, 435-444.
Oelke et al., Ex vivo induction and expansion of antigen-specific cytotoxic T cells by HLA-Ig-coated artificial antigen-presenting cells, Nature Medicine (2003); 9(5):619-624.
Oelsner, S., et al., Continuously expanding CAR NK-92 cells display selective cytotoxicity against B-cell leukemia and lymphoma, Cytotherapy, 2017; 19: 235-249.
Ohgaki et al., 2017, Ratiometric fluorescence imaging of cell surface pH by poly(ethylene glycol)-phospholipid conjugated with fluorescein isothiocyanate. Scientific Reports, 7:17484, p. 1-9.
Okazaki et al., PD-1 immunoreceptor inhibits B cell receptor mediated signaling by recruiting src homology2-domain-containing tyrosine phosphatase 2 to phosphotyrosine , PNAS Nov. 20, 2001, vol. 98, No. 24, 13866-13871.

(56) References Cited

OTHER PUBLICATIONS

Orr, B. et al., Rapid method for measuring ScFv thermal stability by yeast surface display, Biotechnol Prog., 2003. 19, 631-638.
Pages et al., Two Distinct Intracytoplasmic Regions of the T-cell Adhesion Molecule CD28 Participatein Phosphatidylinositol 3-Kinase Association The Journal of Biological Chemistry, vol. 271, No. 16, Apr. 19, 1996, pp. 9403-9409.
Paillard, F. Immunotherapy with T cells bearing chimeric antitumor(1999); 10: 151-153.
Paillasse, M, et al., Insights into the Cholecystokinin 2 Receptor Binding Site and Processes of Activation, The American Society for Pharmacology and Experimental Therapeutics (2006); 70:1935-1945.
Pameijer, C.R., et al., Conversion of a tumor-binding peptide identified by phage display to a functional chimeric T cell antigen receptor, Cancer Gene Ther., 2007, 14, 91-07.
Park et al., Treating cancer with genetically engineered T cells Trends Biotechnol. Nov. 29, 2011(11): 550-557.
Parkhurst et al. Characterization of genetically modified T-cell receptors that recognize the CEA:691-699 peptide in the context of HLA-A2.1 on human colorectal cancer cells (2009) Clin Cancer Res. Jan. 1, 2009;15(1):169-80.
Patel Jaina M et al: Cancer CARtography: charting out a new approach to cancer immunotherapy, Immunotherapy. 2014;6(6):675-8.
Pollock et al., Inducible T cell antigen 4-1BB. Analysis of expression and function, J Immunol 1993; 150:771-781.
Porter DL, et al. Chimeric antigen receptor T cells persist and induce sustained remissions in relapsed refractory chronic lymphocytic leukemia. Science translational medicine. 2015;7(303):303-39. doi: 10. 1 126/scitranslmed.aac5415. PubMed PMID:26333935.
Porter, D.L. et al., Chimeric antigen receptor-modified T cells in chronic lymphoid leukemia, N. Engl. J. Med., 2011, 365, 725-733.
Prasad et al., T-cell antigen CD28 interacts with the lipid kinase phosphatidylinositol3-kinase by a cytoplasmic Tyr(P)-Met-Xaa-Met motif , Proc. Natl. Acad. Sci. USA, vol. 91, pp. 2834-2838, Mar. 1994.
Product brochure for the Engineered Autologous Cell Therapy (eACT™) Platform, available from Kite Pharma, retrieved Oct. 25, 2015 from http://www.kitepharma.com/c/products/eact.php.
Pule et al., Artificial T-cell receptors, Cytotherapy (2003) 5(3):211-226.
Pule et al., Virus-specific T cells engineered to coexpress tumor-specific receptors: persistence and antitumor activity in individuals with neuroblastoma, Nat. Med. (2008); 14: 1264-1270.
Qin et al., Incorporation of a hinge domain improves the expansion of chimeric antigen receptor T cells, Journal of Hematology & Oncology (2017) 10:68.
Rafiq et al., Dec. 17, 2019, Engineering strategies to overcome the current roadblocks in CAR T cell therapy, Nature Reviews Clinical Oncology, 17(3):147-167.
Rai et al., Expression systems for production of heterologous proteins, Current Science2001, vol. 80, No. 9, pp. 1121-1128.
Recent patent applications in chimeric antigen receptors, *Nature Biotechnology* 32(3): 239 (2014).
Reddy et al., Elimination of Fc Receptor-Dependent Effector Functions of a Modified lgG4Monoclonal Antibody to Human CD4, J Immunol 2000; 164: 1925-1933.
Redmond et al., The role of OX40-mediated co-stimulation in T cell activation and survival, Crit. Rev. Immunol. 2009, 29(3): 187-201.
Reichert, J. Day 1, Emerging Disruptive Technologies and Cutting-Edge Analytical Techniques, MAbs, 2009, 1, 190-209.
Restifo et al., Adoptive immunotherapy for cancer: harnessing the T cell response, Nat. Rev. Immunol. (Mar. 22, 2012) 12(4):269-281.
Reubi, Jean Claude, Peptide Receptors as Molecular Targets for Cancer Diagnosis and Therapy, Endocrine Reviews 24(4): 389-427.
Riha et al., CD28 co-signaling in the adaptive immune response Self/Nonself 1:3,231-240; Jul./Aug./Sep. 2010.
Riley et al., The CD28 family: a T-cell rheostat for therapeutic control of T-cell activation, Blood, Jan. 1, 2005, vol. 105, No. 1, pp. 13-21.
Riviere, I., Gallardo, H. F., Hagani, A B. & Sadelain, M. Retroviral-mediated gene transfer in primary murine and human T-lymphocytes. Mol. Biotechnol. 15, 133-142 (2000).
Roberts et al., Chemistry for peptide and protein PEGylation, Advanced Drug Delivery Reviews (2002); 54:459-476.
Rodgers, D. et al., Switch-mediated activation and retargeting of CAR-T cells for B-cell malignancies, Proc. Natl. Acad. Sci., 2016, 113, E459-468.
Romeo, C. at al., Sequence requirements for induction of cytolysis by the T cell antigen/Fc receptor zeta chain, Cell (1992); 68:889-897.
Romeo, C., et al., Cellular immunity to HIV activated by CD4 fused to T cell or Fc receptor polypeptides, Cell (1991); 64:1037-1046.
Rosenberg Cell transfer immunotherapy for metastatic solid cancer—what clinicians need to know (2011) Nat Rev Clin Oncol. 8(10):577-85).
Rosenberg et al. Adoptive cell transfer: a clinical path to effective cancer immunotherapy. Nat Rev Cancer. Apr. 2008; 8(4):299-308.
Rosenberg, S. A. et al., Adoptive cell therapy for the treatment of patients with metastatic melanoma, Current Opinion in Immunology, 2009, 21, 233-240.
Rotz Seth J. et al. Severe cytokine release syndrome in a patient receivingPD-1-directed therapy Pediatr Blood Cancer. Dec. 2017;64(12). Epub May 24, 2017 (4 pages).
Rueckert S, et al., A monoclonal antibody as an effective therapeutic agent in breast cancer: trastuzumab Expert Opin Biol Ther. Jun. 2005;5(6):853-66.
Ruella et al., 2016, Dual CD19 and CD123 targeting prevents antigen-loss replaces after cd19-directed immunotherapies, J Clin Invest. 126(10):3814-3826.
Rushworth et al., 2014, Universal artificial antigen presenting cells to selectively propagate T cells expressing chimeric antigen receptor independent of specificity, Journal of Immunotherapy, 37(4):204-213.
Sadelain et al., Targeting Tumours with Genetically Enhanced T Lymphocytes, Nat Rev Cancer (Jan. 2003); 3(1): 35-45.
Sadelain, et al., The promise and potential pitfalls of chimeric antigen receptors, Current Opinion in Immunology (2009); 21: 215-223.
Sadelain, M. et al., The basic principles of chimeric antigen receptor design, Cancer Discov., 2013, 3, 388-398.
Samudrala et al., 1999, Ab Initio Protein Structure Prediction Using a Combined Hierarchical Approach, Proteins, Structure, Function and Genetics Suppl., 3:194-198.
Saoulli, C, et al., CD28-independent, TRAF2-dependent Costimulation of Resting T Cells by 4-1BB Ligand, Master of Science Thesis, Department of Immunology University of Toronto (1998), 77 pp.
Saraswat et al., DNA as Therapeutics; an Update, Indian J Pharm Sci. Sep.-Oct. 2009;71(5): 488-498.
Scholler, J., et al., Decade-long safety and function of retroviral-modified chimeric antigen receptor T cells, Sci Transl Med (May 2, 2012); 4(132): 132ra53 (7 pages).
Schonfeld, K, et al., Selective Inhibition of Tumor Growth by Clonal NK Cells Expressing an Erb82/HER2-Specific Chimeric Antigen Receptor , Mol. Ther., vol. 23 No. 2, 330-338 Feb. 2015.
Schreiber, S.L., Organic synthesis toward small-molecule probes and drugs PNAS, vol. 108, No. 17, Apr. 26, 2011, pp. 6699-6702.
Schwesinger et al., Unbinding forces of single antibody-antigen complexes correlate with their thermal dissociation rates, PNAS (2000) 97(18), 9972-9977.
Scott, D., et al., Immunogenicity of biotinylated hapten-avidin complexes, Mol Immunol(1984); 21(11): 1055-60.
Sega, E. et al., Tumor detection using folate receptor-targeted imaging agents, Cancer Metastasis Rev., 2008, 27, 655-664.
Sentman Challenges of creating effective chimeric antigen receptors for cancer therapy Immunotherapy. Aug. 2013;5(8):783-5.
Serghides et al., Evaluation of OX40 Ligand as a Costimulator of Human Antiviral Memory CD8 T Cell Responses: Comparison with B7.1 and 4-1BBL, The Journal of Immunology 175:6368-6377 (2005).

(56) References Cited

OTHER PUBLICATIONS

Shields et al., High Resolution Mapping of the Binding Site on Human IgG1 for FcγRI, FcγRII, FcγRIII, and FcRn and Design of IgG1 Variants with Improved Binding to the FcγR*, The Journal of Biological Chemistry 2001, vol. 276, No. 9, Issue of Mar. 2, pp. 6591-6604.
Shirasu, N. et al., Construction and Molecular Characterization of Human Chimeric T-Cell Antigen Receptors Specific for Carcinoernbryonic Antigen, Anticancer Research (2010); 30:2731-2738.
Singh et al., May 2013, Manufacture of clinical-grade CD19-specific T cells stably expressing chimeric antigen receptor using sleeping beauty system and artificial antigen presenting cells, Plos One, 8(5):e64138, 12 pp.
Sobota et al., Binding of IgG-Opsonized Particles to FcγR Is an Active Stage of Phagocytosis That Involves Receptor Clustering and Phosphorylation, The Journal of Immunology 2005; 175:4450-4457.
Stancovski et al., Targeting of T Lymphocytes to Neu/HER2-Expressing Cells Using Chimeric Single Chain Fv Receptors, J. Immunol. (1993); 151(11):6577-6582.
Stein, P, et al., The Cytoplasmic Domain of CD28 Is both Necessary and Sufficient for Costimulation of Interleukin-2 Secretion and Association with Phosphatidylinositol3'-Kinase, American Society for Microbiology (1994); 14: 3392-3402.
Stephan et al., T cell-encoded CD80 and 4-1BBL induce auto- and transcostimulation, resulting in potent tumor rejection, Nature Medicine (Dec. 2007); 13(12): 1440-1449.
Stevens et al., Generation of Tumor-Specific CTLs from Melanoma Patients by Using Peripheral Blood Stimulated with Allogeneic Melanoma Tumor Cell Lines, J. Immunol(1995); 154:762-771.
Stothard, 2000, The Sequence Manipulation Suite: JavaScript Programs for Analyzing and Formatting Protein and DNA Sequences. Biotechniques, 28(6):1102-1104.
Suhoski, M.M., et al., Engineering artificial antigen-presenting cells to express a diverse array of co-stimulatory molecules. Mol Ther, 2007. 15(5): p. 981-8.
Sun et al., Jan. 2018, Immunotherapy with CAR-Modified T cells: toxicities and overcoming strategies, Journal of Immunology Research, 2018:1-10.
Sutherland et al., 2020, Modular Chimeric Antigen Receptor Systems for Universal CART Cell Retargeting. Int. J. Mol. Sci., 21(19):7222, p. 1-14.
Swanson et al., 2015, Fluorescent Cancer-Selective Alkylphosphocholine Analogs for Intraoperative Glioma Detection. Neurosurgery, 76:115-124.
Swanson et al., The coordination of signaling during Fc receptor-mediated phagocytosis, Journal of Leukocyte Biology, vol. 76, Dec. 2004, pp. 1093-1103.
Tam et al., Functional, Biophysical, and Structural Characterization of Human IgG1 andIgG4 Fc Variants with Ablated Immune Functionality, Antibodies 2017, 6, 12.
Tamada et al. Redirecting Gene-Modified T Cells toward Various Cancer Types Using Tagged Antibodies, Clinical Cancer Research (Oct. 2, 2012) vol. 18, Iss. 23, pp. 6436-6445, with correction.
Tanaka, Toshio et al. Immunotherapeutic implications of IL-6 blockade for cytokine storm. Immunotherapy. Jul. 2016; 8(8):959-70.
Tapeinos et al., 2016, Physical, Chemical, and Biological Structures based on ROS-Sensitive Moieties that are Able to Respond to Oxidative Microenvironments, Adv. Mater. 28:5553-5585.
Tatsumi et al., 2012, he non-invasive cell surface modification of hepatocytes with PEG-lipid derivatives, Biomaterials, 33:821-828.
Teachey D. T. et al. Cytokine release syndrome after blinatumomab treatment related to abnormal macrophage activation and ameliorated with cytokine-directed therapy Blood. Jun. 27, 2013;121(26):5154-7. doi: 10.1182/blood-2013-02-485623. Epub May 15, 2013.
Themeli, M., et al., Generation of tumor-targeted human T lymphocytes from induced pluripotent stem cells for cancer therapy, Nat Biotechnol (2013); 31(10):928-33 (Epub Aug. 11, 2013).
Tsukahara et al. CD19 target-engineered T-cells accumulate at tumor lesions in human B-cell lymphoma xenograft mouse models (2013) Biochem Biophys Res Commun 438(1): 84-9. Epub Jul. 17, 2013.
Tumor necrosis factor receptor superfamily, HUGO Gene Nomenclature Committee, 2 pp.
Turatti, F., et al., Redirected activity of human antitumor chimeric immune receptors is governed by antigen and receptor expression levels and affinity of interaction, J Immunother (2007); 30(7): 684-93.
Turtle et al., Engineered T cells for anti-cancer therapy Curr. Opin. Immunol., Oct. 2012; 24(5): 633-39. Epub Jul. 18, 2012.
Uherek, C, et al., Chimeric antigen receptors for the retargeting of cytotoxic effector cells, J. Hematother. Stem Cell Res. (2001); 10: 523-534.
UniProtKB—O43914, TYRO protein tyrosine kinase-binding protein, pp. 1-15.
UniProtKB—P01732 (CD8A_HUMAN). T-cell surface glycoprotein CD8 alpha chain; 11pages; retrieved on May 13, 2016 from http://www.uniprot.org/uniprot/P01732.
UniProtKB—P02701, AVidin Precursor—Gallus Chicken.
UniProtKB—P10747 (CD28_HUMAN).
UniProtKB—P10966 (CD8B_HUMAN).
UniProtKB—P20963 (CD3Z_HUMAN). T-cell surface glycoprotein CD3 zeta chain; 12pages; retrieved on May 13, 2016 from http://www.uniprot.org/uniprot/P20963.
UniProtKB—Q07011 (TNR9_HUMAN). Tumor necrosis factor receptor superfamily member 9; 14 pages; retrieved on May 13, 2016 from http://www.uniprot.org/uniprot/Q07011.
Urba, W.J et al., Redirecting T cells, New Engl. J. Med., 2011, 365, 754-757.
Urbanska et al., A Universal Strategy for Adoptive Immunotherapy of Cancer through Use of a Novel T-cell Antigen Receptor, Cancer Research (2012) 72(7): 1844-1852.
Urbanska, K., et al., A Universal Immune Receptor Expressed by T Cells for the Targeting of Diverse and Multiple Tumor Associated Antigens IN Abstracts for the 26th Annual Scientific Meeting of the Society for Immunotherapy of Cancer (SITC), J Immunother, vol. 34, No. 9, Nov.-Dec. 2011 (62 pages), p. 381.
Uttenthal, B.J., et al., Challenges in T cell receptor gene therapy. J Gene Med (Jun. 2012); 14(6): 386-99.
Van Dam, G. et al., Intraoperative tumor-specific fluorescence imaging in ovarian cancer by folate receptor-α targeting: first in-human results, Nature Medicine, 2011, 17, 1315-1319.
Van Rhijn et al., Nov. 30, 2015, Human autoreactive T cells recognize CD1b and phospholipids, Proceedings of the National Academy of Sciences 113(2):380-385.
Vaughan et al., Human antibodies with sub-nanomolar affinitis isolate from a large non-immunized phage display library, Nature Biotechnology (1996) vol. 14(3), pp. 309-314.
Verdine et al., The Challenge of Drugging Undruggable Targets in Cancer: Lessons Learned from Targeting BCL-2 Family Members Clin. Cancer Res. vol. 13, No. 24, Dec. 15, 2007, pp. 7264-7270.
Verhoeyen et al. Lentiviral vector gene transfer into human T cells (2009) Methods Mol Biol. 506: 97-114.
Vidarsson et al., Oct. 20, 2014, IgG subclasses and allotypes: from structure to effector functions. Front. Immunol. 5:520, 17 pp.
Wang et al. Phenotypic and functional attributes of lentivirus-modified CD19-specific human CD8+ central memory T cells manufactured at clinical scale (2012) J Immunother.35(9):689-701.
Wang et al., Current status and perspectives of chimeric antigen receptor modified T cells for cancer treatment, Protein Cell 2017, 8(12):896-925.
Wayua, C. et al., Evaluation of a Cholecystokinin 2 Receptor-Targeted Near-Infrared Dye for Fluorescence-Guided Surgery of Cancer, Molecular Pharmaceutics, 2014, 11,468-476.
Weichert et al., Jun. 11, 2014, Alkylphosphocholine analogs for broad-spectrum cancer imaging and therapy. Science Translational Medicine, 6(240):240ra75, 24 pp.
Weijtens, M. E. et al., Single chain Ig/gamma gene-redirected human T lymphocytes produce cytokines, specifically lyse tumor cells, and recycle lytic capacity., J. Immunol.(Jul. 15, 1996); 157(2):836-43.

(56) References Cited

OTHER PUBLICATIONS

Weissman et al., Molecular cloning and chromosomal localization of the human T-cell receptor zeta chain: Distinction from the molecular CD3 complex Proc. Natl. Acad. Sci. vol. 85, Dec. 1988, pp. 9709-9713.
Weissman et al., Role of the zeta chain in the expression of the T cell antigen receptor: genetic reconstitution studies The EMBO Journal, vol. 8, No. 12, 1989, pp. 3651-3656.
Wen et al., 2002, 4-1BB Ligand-Mediated Costimulation of Human T Cells Induces CD4 andCD8 T Cell Expansion, Cytokine Production, and the Development of Cytolytic Effector Function1, 168:4897-4906.
Wesolowski, J, et al., Single domain antibodies: promising experimental and therapeutic tools in infection and immunity, Med Microbiol Immunol (2009) 198:157-174.
Wilkie et al., Retargeting of Human T Cells to Tumor-Associated MUC1: The Evolution of a Chimeric Antigen Receptor, The Journal of Immunology Apr. 2008, pp. 4901-4909.
Wilson, et al. DAP12 and KAP10 (DAP10)-novel transmembrane adapter proteins of the CD3zeta family, Immunol Res. (2000); 22(1):21-42.
Wu et al., Adoptive T-cell therapy using An A tumor-infiltrating lymphocytes for metastatic melanoma: current status and future outlook Cancer, Mar. 2012 18(2): 160-75.
Wu et al., Remote control of therapeutic T cells through a small molecule-gated chimeric receptor, Science (2015) vol. 350, Issue 6258, pp. 293 and aab4077-aab4077.
Wu, et al., An activating immunoreceptor complex formed by NKG2D and DAP10, Science (1999); 285:730-732.
Xu et al., Cytokine release syndrome in cancer immunotherapy with chimeric antigen receptor engineered T cells Cancer Lett. Feb. 28, 2014;343(2):172-8. Epub Oct. 16, 2013.
Xu, X.J., et al., Efficacy and safety of adoptive immunotherapy using anti-CD 19 chimeric antigen receptor transduced T-cells: a systematic review of phase I clinical trials, LeukLymphoma (2013); 54(2): 255-60 (Published online: Sep. 8, 2012).
Yamamoto et al., 2016, Interaction of poly(ethylene glycol)-conjugated phospholipids with supported lipid membranes and their influence on protein adsorption. Science and Technology of Advanced Materials, 17(1):677-684.
Ye et al., Sep. 1999, The Structural Basis for the Recognition of Diverse Receptor Sequences by TRAF2, The Weill Medical College and Graduate School of Medical Sciences of Cornell University; 4:321-330.
Yee, C., et al., Prospects for Adoptive T Cell Therapy, Current Opinion in Immunology(1997); 9(5):702-708.
Zarour, 2016, Reversing T-cell dysfunction and exhaustion in cancer, Clinical Cancer Resarch, 22(8):1856-1864.
Zhang et al., Phase I Escalating-Dose Trial of CAR-T Therapy Targeting CEA+ Metastatic Colorectal Cancers, Molecular Therapy (2017), 25(5): 1248-1258.
Zhang, H., et al., 4-IBB is superior to CD28 costimulation for generating CD8+ cytotoxic lymphocytes for adoptive immunotherapy. J Immunol, 2007. 179(7): p. 4910-8.
Zhao, Y. et al., A herceptin-based chimeric antigen receptor with modified signaling domains leads to enhanced survival of transduced T lymphocytes and antitumor activity, J. Immunol, 2009, 183, 5563-5574.
Zheng et al., Arming Tumor-Reactive T Cells with Costimulator B7-1 Enhances Therapeutic Efficacy of the T Cells, Cancer Research, 2006, vol. 66, No. 13, pp. 6793-6799.
Zhong, et al., Integrated CD28 and 4-1BB Signals Strongly Potentiate CD8+ T Cell MediatedEradication of Metastatic Prostate Cancer, Molecular Therapy (Jan. 1, 2006); 13: p. S103, Abstract.
Leahy, Daniel J. et al., "Sequences of 12 monoclonal anti-dinitrophenyl spin-label antibodies for NMR studies" Proc. Natl. Acad. Sci. USA, Jun. 1988, pp. 3661-3665, vol. 85.
International Search Report for PCT/US2021/016177 dated May 24, 2021.
Butler et al., Jan. 2014, Human cell-based artificial antigen-presenting cells for cancer immunotherapy. Immunol Rev. 257(1):191-209.
Kiselevsky et al., 2019, Prospectives of application of the genetically modified lymphocytes with chimeric T-cell receptor (CAR-T-cells) for the therapy of solid tumors, Immunologiya. 40(4):48-55.
Lee et al., 2017, Abstract LB-187: New methods for controlling CAR T cell-mediated cytokine storms, Cancer Res, 77(13_ Supplement):LB-187.
Low et al., 2020, Abstract 3236:Rejuvenation of exhausted CAR-T cells with a targeted TLR7 agonist, Cancer Res. 80 (16_ Supplement): 3236.
Luo et al., 2022, Targeted Rejuvenation of Exhausted Chimeric Antigen Receptor T Cells Regresses Refractory Solid Tumors, Mol Cancer Res. 20(5):823-833.
Lv et al., May 2, 2016, Evaluation of a Carbonic Anhydrase IX-Targeted Near-Infrared Dye for Fluorescence-Guided Surgery of Hypoxic Tumors, Mol Pharm. 13(5):1618-1625.
Napoleon et al., 2022, Design, Synthesis, and Targeted Delivery of an Immune Stimulant that Selectively Reactivates Exhausted CAR T Cells, Angew Chem Int Ed Engl. 61(15):e202113341.
Ruella et al., 2017, Kinase inhibitor ibrutinib to prevent cytokine-release syndrome after anti-CD19 chimeric antigen receptor T cells for B-cell neoplasms, Leukemia. 31(1):246-248.
Schuijs et al., Jan. 2019, Professional and 'Amateur' Antigen-Presenting Cells In Type 2 Immunity. Trends Immunol. 40(1):22-34.
Zah et al., Jun. 2016, T cells expressing CD19/CD20 bispecific chimeric antigen receptors prevent antigen escape by malignant B cells. Cancer immunology research. 4(6):498-508.
Brunger et al., 1991, 2.9 A resolution structure of an anti-dinitrophenyl-spin-label monoclonal antibody fab fragment with bound hapten, Journal of Molecular Biology, 221:239-256.
Gonzalez et al., Jun. 2004, Genetic engineering of cytolytic T lymphocytes for adoptive T-cell therapy of neuroblastoma, The Journal of Gene Medicine, 6(6):704-711.
Van Blitterswijk et al., 2013, Anticancer mechanisms and clinical application of alkylphopholipids, Biochimica et Biophysica Acta, 1831(3):663-674.
Van der Luit et al., 2007, A new class of anticancer alkylphospholipids uses lipid rafts as membrane gateways to induce apoptosis in lymphoma cells, Mol Cancer Ther, 6(8):2337-2345.
Midelfort. 2006, Context-dependent mutations predominate in an engineered high-affinity single chain antibody fragment. Protein Sci;15(2):324-334.

* cited by examiner

SEQUENCE LISTING

```
<160> NUMBER OF SEQ ID NOS: 29

<210> SEQ ID NO 1
<211> LENGTH: 217
<212> TYPE: PRT
<213> ORGANISM: Artificial Sequence
<220> FEATURE:
<223> OTHER INFORMATION: VH of anti DNP scFv (Ab-1; 1BAF)

<400> SEQUENCE: 1

Asp Val Gln Leu Gln Glu Ser Gly Pro Gly Leu Val Lys Pro Ser Gln
1               5                   10                  15

Ser Gln Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Met Ser Tyr Ser Gly Ser Thr Arg Tyr Asn Pro Ser Leu
    50                  55                  60

Arg Ser Arg Ile Ser Ile Thr Arg Asp Thr Ser Lys Asn Gln Phe Phe
65                  70                  75                  80
```

-continued

```
Leu Gln Leu Lys Ser Val Thr Thr Glu Asp Thr Ala Thr Tyr Phe Cys
                85                  90                  95

Ala Arg Gly Trp Pro Leu Ala Tyr Trp Gly Gln Gly Thr Gln Val Ser
            100                 105                 110

Val Ser Glu Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Pro Arg Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys
    210                 215


<210> SEQ ID NO 2
<211> LENGTH: 214
<212> TYPE: PRT
<213> ORGANISM: Artificial Sequence
<220> FEATURE:
<223> OTHER INFORMATION: VL of anti DNP scFv (Ab-1; 1BAF)

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Tyr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Val Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 3
<211> LENGTH: 125
<212> TYPE: PRT
<213> ORGANISM: Artificial Sequence
<220> FEATURE:
<223> OTHER INFORMATION: VH of anti DNP scFv (Ab-2; XC)

<400> SEQUENCE: 3

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Ser Ser Tyr Cys Ile Cys Trp Val Arg Gln Ala Pro Gly Lys Gly
        35                  40                  45

Leu Glu Trp Ile Gly Cys Ile Tyr Ala Gly Ser Ser Gly Ser Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Ala Pro Tyr Ser Ser Gly Trp Val Leu
            100                 105                 110

Tyr Phe Asn Leu Trp Gly Pro Gly Thr Leu Val Ile Val
        115                 120                 125
```

<210> SEQ ID NO 4
<211> LENGTH: 104
<212> TYPE: PRT
<213> ORGANISM: Artificial Sequence
<220> FEATURE:
<223> OTHER INFORMATION: VL of anti DNP scFv (Ab-2; XC)

<400> SEQUENCE: 4

```
Ala Gln Val Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Gly Asn
            20                  25                  30

Ser Arg Leu Ala Trp Tyr Gln Gln Lys Pro Gly Gln Ser Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Ser Tyr Tyr Cys Gln Gly Gly Tyr Tyr Ser
                85                  90                  95

Gly Asn Leu Asp Ala Leu Ala Phe
            100
```

<210> SEQ ID NO 5
<211> LENGTH: 125
<212> TYPE: PRT
<213> ORGANISM: Artificial Sequence
<220> FEATURE:
<223> OTHER INFORMATION: VH of anti DNP scFv (Ab-3)

<400> SEQUENCE: 5

```
Gln Gln Leu Glu Gln Ser Gly Gly Gly Ala Glu Gly Gly Leu Val Lys
1               5                   10                  15
```

-continued

```
Pro Gly Gly Ser Leu Glu Leu Cys Cys Lys Ala Ser Gly Phe Ser Leu
            20                  25                  30

Ser Ser Ser Tyr Cys Ile Cys Trp Val Arg Gln Ala Pro Gly Lys Gly
        35                  40                  45

Leu Glu Trp Ile Gly Cys Ile Tyr Ala Gly Ser Ser Gly Ser Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Ala Pro Tyr Ser Ser Gly Trp Val Leu
            100                 105                 110

Tyr Phe Asn Leu Trp Gly Pro Gly Thr Leu Val Ile Val
        115                 120                 125


<210> SEQ ID NO 6
<211> LENGTH: 119
<212> TYPE: PRT
<213> ORGANISM: Artificial Sequence
<220> FEATURE:
<223> OTHER INFORMATION: VL of anti DNP scFv (Ab-3)

<400> SEQUENCE: 6

Pro Gly Ala Thr Phe Ala Gln Val Leu Thr Gln Thr Pro Ser Pro Val
1               5                   10                  15

Ser Ala Ala Val Gly Gly Thr Val Thr Ile Ser Cys Gln Ser Ser Glu
            20                  25                  30

Ser Val Tyr Gly Asn Ser Arg Leu Ala Trp Tyr Gln Gln Lys Pro Gly
        35                  40                  45

Gln Ser Pro Lys Leu Leu Ile Tyr Tyr Ala Ser Thr Leu Ala Ser Gly
    50                  55                  60

Val Pro Ser Arg Phe Lys Gly Ser Gly Ser Gly Thr Gln Phe Thr Leu
65                  70                  75                  80

Thr Ile Ser Asp Leu Glu Cys Asp Asp Ala Ala Ser Tyr Tyr Cys Gln
                85                  90                  95

Gly Gly Tyr Tyr Ser Gly Asn Leu Asp Ala Leu Ala Phe Gly Gly Gly
            100                 105                 110

Thr Glu Val Val Val Arg Gly
        115


<210> SEQ ID NO 7
<211> LENGTH: 263
<212> TYPE: PRT
<213> ORGANISM: Artificial Sequence
<220> FEATURE:
<223> OTHER INFORMATION: VL-linker-VH of anti DNP scFv (Ab-3)

<400> SEQUENCE: 7

Pro Gly Ala Thr Phe Ala Gln Val Leu Thr Gln Thr Pro Ser Pro Val
1               5                   10                  15

Ser Ala Ala Val Gly Gly Thr Val Thr Ile Ser Cys Gln Ser Ser Glu
            20                  25                  30

Ser Val Tyr Gly Asn Ser Arg Leu Ala Trp Tyr Gln Gln Lys Pro Gly
        35                  40                  45

Gln Ser Pro Lys Leu Leu Ile Tyr Tyr Ala Ser Thr Leu Ala Ser Gly
    50                  55                  60

Val Pro Ser Arg Phe Lys Gly Ser Gly Ser Gly Thr Gln Phe Thr Leu
65                  70                  75                  80
```

-continued

```
Thr Ile Ser Asp Leu Glu Cys Asp Asp Ala Ala Ser Tyr Tyr Cys Gln
                85                  90                  95

Gly Gly Tyr Tyr Ser Gly Asn Leu Asp Ala Leu Ala Phe Gly Gly Gly
            100                 105                 110

Thr Glu Val Val Val Arg Gly Gly Gly Gly Gly Ser Gly Gly Gly Gly
        115                 120                 125

Ser Gly Gly Gly Gly Ser Gln Cys Gln Gln Leu Glu Gln Ser Gly Gly
    130                 135                 140

Gly Ala Glu Gly Gly Leu Val Lys Pro Gly Gly Ser Leu Glu Leu Cys
145                 150                 155                 160

Cys Lys Ala Ser Gly Phe Ser Leu Ser Ser Ser Tyr Cys Ile Cys Trp
                165                 170                 175

Val Arg Gln Ala Pro Gly Lys Gly Leu Glu Trp Ile Gly Cys Ile Tyr
            180                 185                 190

Ala Gly Ser Ser Gly Ser Thr Tyr Tyr Ala Ser Trp Val Asn Gly Arg
        195                 200                 205

Phe Thr Leu Ser Arg Asp Ile Asp Gln Ser Thr Gly Cys Leu Gln Leu
    210                 215                 220

Asn Ser Leu Thr Ala Ala Asp Thr Ala Met Tyr Tyr Cys Ala Arg Ala
225                 230                 235                 240

Pro Tyr Ser Ser Gly Trp Val Leu Tyr Phe Asn Leu Trp Gly Pro Gly
                245                 250                 255

Thr Leu Val Ile Val Ser Ser
            260


<210> SEQ ID NO 8
<211> LENGTH: 263
<212> TYPE: PRT
<213> ORGANISM: Artificial Sequence
<220> FEATURE:
<223> OTHER INFORMATION: VH-linker-VL of anti DNP scFv (Ab-3)

<400> SEQUENCE: 8

Gln Cys Gln Gln Leu Glu Gln Ser Gly Gly Gly Ala Glu Gly Gly Leu
1               5                   10                  15

Val Lys Pro Gly Gly Ser Leu Glu Leu Cys Cys Lys Ala Ser Gly Phe
            20                  25                  30

Ser Leu Ser Ser Ser Tyr Cys Ile Cys Trp Val Arg Gln Ala Pro Gly
        35                  40                  45

Lys Gly Leu Glu Trp Ile Gly Cys Ile Tyr Ala Gly Ser Ser Gly Ser
    50                  55                  60

Thr Tyr Tyr Ala Ser Trp Val Asn Gly Arg Phe Thr Leu Ser Arg Asp
65                  70                  75                  80

Ile Asp Gln Ser Thr Gly Cys Leu Gln Leu Asn Ser Leu Thr Ala Ala
                85                  90                  95

Asp Thr Ala Met Tyr Tyr Cys Ala Arg Ala Pro Tyr Ser Ser Gly Trp
            100                 105                 110

Val Leu Tyr Phe Asn Leu Trp Gly Pro Gly Thr Leu Val Ile Val Ser
        115                 120                 125

Ser Gly Gly Gly Gly Ser Gly Gly Gly Gly Ser Gly Gly Gly Gly Ser
    130                 135                 140

Pro Gly Ala Thr Phe Ala Gln Val Leu Thr Gln Thr Pro Ser Pro Val
145                 150                 155                 160

Ser Ala Ala Val Gly Gly Thr Val Thr Ile Ser Cys Gln Ser Ser Glu
                165                 170                 175
```

```
Ser Val Tyr Gly Asn Ser Arg Leu Ala Trp Tyr Gln Gln Lys Pro Gly
            180                 185                 190

Gln Ser Pro Lys Leu Leu Ile Tyr Tyr Ala Ser Thr Leu Ala Ser Gly
        195                 200                 205

Val Pro Ser Arg Phe Lys Gly Ser Gly Ser Gly Thr Gln Phe Thr Leu
    210                 215                 220

Thr Ile Ser Asp Leu Glu Cys Asp Asp Ala Ala Ser Tyr Tyr Cys Gln
225                 230                 235                 240

Gly Gly Tyr Tyr Ser Gly Asn Leu Asp Ala Leu Ala Phe Gly Gly Gly
                245                 250                 255

Thr Glu Val Val Val Arg Gly
            260


<210> SEQ ID NO 9
<211> LENGTH: 446
<212> TYPE: PRT
<213> ORGANISM: Artificial Sequence
<220> FEATURE:
<223> OTHER INFORMATION: VH-linker-VL of anti DNP scFv (1BAF)

<400> SEQUENCE: 9

Asp Val Gln Leu Gln Glu Ser Gly Pro Gly Leu Val Lys Pro Ser Gln
1               5                   10                  15

Ser Gln Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Met Ser Tyr Ser Gly Ser Thr Arg Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Lys Ser Val Thr Thr Glu Asp Thr Ala Thr Tyr Phe Cys
                85                  90                  95

Ala Arg Gly Trp Pro Leu Ala Tyr Trp Gly Gln Gly Thr Gln Val Ser
            100                 105                 110

Val Ser Glu Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Pro Arg Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Gly Gly Gly Ser Gly Gly
    210                 215                 220

Gly Gly Ser Gly Gly Gly Gly Ser Gln Ile Val Leu Thr Gln Ser Pro
225                 230                 235                 240

Ala Ile Met Ser Ala Ser Pro Gly Glu Lys Val Thr Met Thr Cys Ser
                245                 250                 255

Ala Ser Ser Ser Val Tyr Tyr Met Tyr Trp Tyr Gln Gln Lys Pro Gly
            260                 265                 270
```

-continued

```
Ser Ser Pro Arg Leu Leu Ile Tyr Asp Thr Ser Asn Leu Ala Ser Gly
        275                 280                 285

Val Pro Val Arg Phe Ser Gly Ser Gly Ser Gly Thr Ser Tyr Ser Leu
    290                 295                 300

Thr Ile Ser Arg Met Glu Ala Glu Asp Ala Ala Thr Tyr Tyr Cys Gln
305                 310                 315                 320

Gln Trp Ser Ser Tyr Pro Pro Ile Thr Phe Gly Val Gly Thr Lys Leu
                325                 330                 335

Glu Leu Lys Arg Ala Asp Ala Ala Pro Thr Val Ser Ile Phe Pro Pro
            340                 345                 350

Ser Ser Glu Gln Leu Thr Ser Gly Gly Ala Ser Val Val Cys Phe Leu
        355                 360                 365

Asn Asn Phe Tyr Pro Lys Asp Ile Asn Val Lys Trp Lys Ile Asp Gly
    370                 375                 380

Ser Glu Arg Gln Asn Gly Val Leu Asn Ser Trp Thr Asp Gln Asp Ser
385                 390                 395                 400

Lys Asp Ser Thr Tyr Ser Met Ser Ser Thr Leu Thr Leu Thr Lys Asp
                405                 410                 415

Glu Tyr Glu Arg His Asn Ser Tyr Thr Cys Glu Ala Thr His Lys Thr
            420                 425                 430

Ser Thr Ser Pro Ile Val Lys Ser Phe Asn Arg Asn Glu Cys
        435                 440                 445


<210> SEQ ID NO 10
<211> LENGTH: 446
<212> TYPE: PRT
<213> ORGANISM: Artificial Sequence
<220> FEATURE:
<223> OTHER INFORMATION: VL-linker-VH of anti DNP scFv (1BAF)

<400> SEQUENCE: 10

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Tyr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Val Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190
```

```
Thr Cys Glu Ala Thr His Lys Thr Ser Thr Ser Pro Ile Val Lys Ser
        195                 200                 205

Phe Asn Arg Asn Glu Cys Gly Gly Gly Gly Ser Gly Gly Gly Gly Ser
    210                 215                 220

Gly Gly Gly Gly Ser Asp Val Gln Leu Gln Glu Ser Gly Pro Gly Leu
225                 230                 235                 240

Val Lys Pro Ser Gln Ser Gln Ser Leu Thr Cys Thr Val Thr Gly Tyr
                245                 250                 255

Ser Ile Thr Ser Asp Tyr Ala Trp Asn Trp Ile Arg Gln Phe Pro Gly
            260                 265                 270

Asn Lys Leu Glu Trp Met Gly Tyr Met Ser Tyr Ser Gly Ser Thr Arg
        275                 280                 285

Tyr Asn Pro Ser Leu Arg Ser Arg Ile Ser Ile Thr Arg Asp Thr Ser
    290                 295                 300

Lys Asn Gln Phe Phe Leu Gln Leu Lys Ser Val Thr Thr Glu Asp Thr
305                 310                 315                 320

Ala Thr Tyr Phe Cys Ala Arg Gly Trp Pro Leu Ala Tyr Trp Gly Gln
                325                 330                 335

Gly Thr Gln Val Ser Val Ser Glu Ala Lys Thr Thr Pro Pro Ser Val
            340                 345                 350

Tyr Pro Leu Ala Pro Gly Ser Ala Ala Gln Thr Asn Ser Met Val Thr
        355                 360                 365

Leu Gly Cys Leu Val Lys Gly Tyr Phe Pro Glu Pro Val Thr Val Thr
    370                 375                 380

Trp Asn Ser Gly Ser Leu Ser Ser Gly Val His Thr Phe Pro Ala Val
385                 390                 395                 400

Leu Gln Ser Asp Leu Tyr Thr Leu Ser Ser Ser Val Thr Val Pro Ser
                405                 410                 415

Ser Pro Arg Pro Ser Glu Thr Val Thr Cys Asn Val Ala His Pro Ala
            420                 425                 430

Ser Ser Thr Lys Val Asp Lys Lys Ile Val Pro Arg Asp Cys
        435                 440                 445


<210> SEQ ID NO 11
<211> LENGTH: 246
<212> TYPE: PRT
<213> ORGANISM: Artificial Sequence
<220> FEATURE:
<223> OTHER INFORMATION: VH-linker-VL of anti DNP scFv (XC)

<400> SEQUENCE: 11

Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Ser Ser Tyr Cys Ile Cys Trp Val Arg Gln Ala Pro Gly Lys Gly
        35                  40                  45

Leu Glu Trp Ile Gly Cys Ile Tyr Ala Gly Ser Ser Gly Ser Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Ala Pro Tyr Ser Ser Gly Trp Val Leu
            100                 105                 110
```

```
Tyr Phe Asn Leu Trp Gly Pro Gly Thr Leu Val Ile Val Ser Ser Gly
        115                 120                 125

Gly Gly Gly Ser Gly Gly Gly Gly Ser Gly Gly Gly Gly Ser Ala Gln
    130                 135                 140

Val Leu Thr Gln Thr Pro Ser Pro Val Ser Ala Ala Val Gly Gly Thr
145                 150                 155                 160

Val Thr Ile Ser Cys Gln Ser Ser Glu Ser Val Tyr Gly Asn Ser Arg
                165                 170                 175

Leu Ala Trp Tyr Gln Gln Lys Pro Gly Gln Ser Pro Lys Leu Leu Ile
            180                 185                 190

Tyr Tyr Ala Ser Thr Leu Ala Ser Gly Val Pro Ser Arg Phe Lys Gly
        195                 200                 205

Ser Gly Ser Gly Thr Gln Phe Thr Leu Thr Ile Ser Asp Leu Glu Cys
    210                 215                 220

Asp Asp Ala Ala Ser Tyr Tyr Cys Gln Gly Gly Tyr Tyr Ser Gly Asn
225                 230                 235                 240

Leu Asp Ala Leu Ala Phe
                245


<210> SEQ ID NO 12
<211> LENGTH: 254
<212> TYPE: PRT
<213> ORGANISM: Artificial Sequence
<220> FEATURE:
<223> OTHER INFORMATION: VL-linker-VH of anti DNP scFv (XC)

<400> SEQUENCE: 12

Ala Gln Val Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Gly Asn
            20                  25                  30

Ser Arg Leu Ala Trp Tyr Gln Gln Lys Pro Gly Gln Ser Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Ser Tyr Tyr Cys Gln Gly Gly Tyr Tyr Ser
                85                  90                  95

Gly Asn Leu Asp Ala Leu Ala Phe Gly Gly Gly Thr Glu Val Val Val
            100                 105                 110

Arg Gly Gly Gly Gly Gly Ser Gly Gly Gly Gly Ser Gly Gly Gly Gly
        115                 120                 125

Ser Gln Gln Leu Glu Gln Ser Gly Gly Gly Ala Glu Gly Gly Leu Val
    130                 135                 140

Lys Pro Gly Gly Ser Leu Glu Leu Cys Cys Lys Ala Ser Gly Phe Ser
145                 150                 155                 160

Leu Ser Ser Ser Tyr Cys Ile Cys Trp Val Arg Gln Ala Pro Gly Lys
                165                 170                 175

Gly Leu Glu Trp Ile Gly Cys Ile Tyr Ala Gly Ser Ser Gly Ser Thr
            180                 185                 190

Tyr Tyr Ala Ser Trp Val Asn Gly Arg Phe Thr Leu Ser Arg Asp Ile
        195                 200                 205

Asp Gln Ser Thr Gly Cys Leu Gln Leu Asn Ser Leu Thr Ala Ala Asp
    210                 215                 220
```

```
Thr Ala Met Tyr Tyr Cys Ala Arg Ala Pro Tyr Ser Ser Gly Trp Val
225                 230                 235                 240

Leu Tyr Phe Asn Leu Trp Gly Pro Gly Thr Leu Val Ile Val
                245                 250


<210> SEQ ID NO 13
<211> LENGTH: 1338
<212> TYPE: DNA
<213> ORGANISM: Artificial Sequence
<220> FEATURE:
<223> OTHER INFORMATION: VH-linker-VL of anti DNP scFv (1BAF)

<400> SEQUENCE: 13

gacgtacaac tgcaagaatc aggtccggga ctggtcaaac ctagccagtc tcagtccttg     60

acgtgcaccg tgacgggcta tagtataacg agtgattacg cttggaattg gattcggcag    120

tttccaggca ataagcttga gtggatgggc tatatgtctt actccggctc aactaggtat    180

aatccgagcc ttcggtctcg gatttctatc acaagagata cgagtaagaa tcagtttttt    240

cttcaactca aaagcgtcac cacggaggat accgccacat atttctgtgc taggggatgg    300

cctcttgctt attgggggca agggacacaa gtgtctgttt ccgaagccaa aacaacgccc    360

ccttcagtct atccgctggc accgggaagc gcggcacaaa ccaatagtat ggtaacgctc    420

ggatgtctcg tcaaggggta ttttcccgag cctgtgacag tgacatggaa ttctgggagt    480

cttagcagcg gagtacatac ttttccggca gtacttcaat ccgatttgta cacgctctcc    540

tctagtgtta cagttccaag ctctccacga cctagtgaga ccgttacatg taacgtcgcg    600

catccggcct cttccactaa agtggataaa aagattgtgc ccagggactg cggcggaggg    660

ggctctggcg gcggaggatc tgggggaggg ggcagccaaa ttgtgttgac ccagtccccg    720

gccataatgt ccgcttctcc tggcgagaag gttactatga cttgctcagc ctcctccagt    780

gtgtattata tgtactggta tcaacaaaag ccgggctctt ccccccggct ccttatatac    840

gacacgagta atctggcaag tggcgtgcct gttagatttt ctgggtccgg ctctggaact    900

tcatactccc tgacaattag ccgaatggaa gccgaggacg cggcgacata ctactgccag    960

caatggtcat cctatccgcc tatcactttt ggagtaggga ccaaattgga gttgaagcgg   1020

gctgatgcgg ctcccacagt tagtattttc cctccgtcca gtgaacaact tacctccggg   1080

ggagcctccg ttgtttgctt tctgaacaac ttttacccga aagatataaa tgtcaagtgg   1140

aagatcgacg gctcagagcg ccaaaacggg gtactcaact catggacaga tcaggatagt   1200

aaagattcaa cttacagtat gtctagtacc ctgacactga cgaaagatga atacgaaaga   1260

cataatagtt atacctgtga agctacacat aagacttcaa cctctcctat tgtaaaatca   1320

ttcaaccgaa acgaatgt                                                 1338


<210> SEQ ID NO 14
<211> LENGTH: 1338
<212> TYPE: DNA
<213> ORGANISM: Artificial Sequence
<220> FEATURE:
<223> OTHER INFORMATION: VL-linker-VH of anti DNP scFv (1BAF)

<400> SEQUENCE: 14

caaattgtgt tgacccagtc cccggccata atgtccgctt ctcctggcga gaaggttact     60

atgacttgct cagcctcctc cagtgtgtat tatatgtact ggtatcaaca aaagccgggc    120

tcttcccccc ggctccttat atacgacacg agtaatctgg caagtggcgt gcctgttaga    180
```

-continued

```
ttttctgggt ccggctctgg aacttcatac tccctgacaa ttagccgaat ggaagccgag    240

gacgcggcga catactactg ccagcaatgg tcatcctatc cgcctatcac ttttggagta    300

gggaccaaat tggagttgaa gcgggctgat gcggctccca cagttagtat tttccctccg    360

tccagtgaac aacttacctc cgggggagcc tccgttgttt gctttctgaa caacttttac    420

ccgaaagata taaatgtcaa gtggaagatc gacggctcag agcgccaaaa cggggtactc    480

aactcatgga cagatcagga tagtaaagat tcaacttaca gtatgtctag taccctgaca    540

ctgacgaaag atgaatacga aagacataat agttatacct gtgaagctac acataagact    600

tcaacctctc ctattgtaaa atcattcaac cgaaacgaat gtggcggagg gggctctggc    660

ggcggaggat ctgggggagg gggcagcgac gtacaactgc aagaatcagg tccgggactg    720

gtcaaaccta gccagtctca gtccttgacg tgcaccgtga cgggctatag tataacgagt    780

gattacgctt ggaattggat tcggcagttt ccaggcaata agcttgagtg gatgggctat    840

atgtcttact ccggctcaac taggtataat ccgagccttc ggtctcggat ttctatcaca    900

agagatacga gtaagaatca gtttttttctt caactcaaaa gcgtcaccac ggaggatacc    960

gccacatatt tctgtgctag gggatggcct cttgcttatt gggggcaagg gacacaagtg   1020

tctgtttccg aagccaaaac aacgccccct tcagtctatc cgctggcacc gggaagcgcg   1080

gcacaaacca atagtatggt aacgctcgga tgtctcgtca aggggtattt tcccgagcct   1140

gtgacagtga catggaattc tgggagtctt agcagcggag tacatacttt tccggcagta   1200

cttcaatccg atttgtacac gctctcctct agtgttacag ttccaagctc tccacgacct   1260

agtgagaccg ttacatgtaa cgtcgcgcat ccggcctctt ccactaaagt ggataaaaag   1320

attgtgccca gggactgc                                                 1338
```

<210> SEQ ID NO 15
<211> LENGTH: 738
<212> TYPE: DNA
<213> ORGANISM: Artificial Sequence
<220> FEATURE:
<223> OTHER INFORMATION: VH-linker-VL of anti DNP scFv (XC)

<400> SEQUENCE: 15

```
cagcagctgg agcagtccgg aggaggagcc gaaggaggcc tggtcaagcc tgggggatcc     60

ctggaactct gctgcaaagc ctctggattc tccctcagta gtagctactg catatgttgg    120

gtccgccagg ctccagggaa ggggctggag tggatcggat gcatttatgc tggtagtagt    180

ggtagcactt actacgcgag ctgggtgaat ggccgattca ctctctccag agacattgac    240

cagagcacag gttgcctaca actgaacagt ctgacagccg cggacacggc catgtattac    300

tgtgcgagag ccccctatag tagtggctgg gtcctctact ttaacttgtg gggcccaggc    360

accctggtca ttgtctcctc aggcggaggg ggctctggcg gcggaggatc tgggggaggg    420

ggcagcgccc aagtgctgac ccagactcca tcgcctgtgt ctgcagctgt gggaggcaca    480

gtcaccatca gttgccagtc cagtgagagt gtttatggta acagccgctt agcctggtat    540

cagcagaaac cagggcagtc tcccaagctc ctgatctatt atgcatccac tctggcatct    600

ggggtccctt cgcggttcaa aggcagtgga tctgggacac agttcactct caccattagc    660

gacctggagt gtgacgatgc tgcctcttac tactgtcaag gcggttatta tagtggtaat    720

cttgatgcgc ttgctttc                                                  738
```

<210> SEQ ID NO 16
<211> LENGTH: 762

<212> TYPE: DNA
<213> ORGANISM: Artificial Sequence
<220> FEATURE:
<223> OTHER INFORMATION: VL-linker-VH of anti DNP scFv (XC)

<400> SEQUENCE: 16
gcccaagtgc tgacccagac tccatcgcct gtgtctgcag ctgtgggagg cacagtcacc 60
atcagttgcc agtccagtga gagtgtttat ggtaacagcc gcttagcctg gtatcagcag 120
aaaccagggc agtctcccaa gctcctgatc tattatgcat ccactctggc atctggggtc 180
ccttcgcggt tcaaaggcag tggatctggg acacagttca ctctcaccat tagcgacctg 240
gagtgtgacg atgctgcctc ttactactgt caaggcggtt attatagtgg taatcttgat 300
gcgcttgctt tcggcggagg gaccgaggtg gtggtcagag gtggcggagg gggctctggc 360
ggcggaggat ctgggggagg gggcagccag cagctggagc agtccggagg aggagccgaa 420
ggaggcctgg tcaagcctgg gggatccctg gaactctgct gcaaagcctc tggattctcc 480
ctcagtagta gctactgcat atgttgggtc cgccaggctc cagggaaggg gctggagtgg 540
atcggatgca tttatgctgg tagtagtggt agcacttact acgcgagctg ggtgaatggc 600
cgattcactc tctccagaga cattgaccag agcacaggtt gcctacaact gaacagtctg 660
acagccgcgg acacggccat gtattactgt gcgagagccc cctatagtag tggctgggtc 720
ctctacttta acttgtgggg cccaggcacc ctggtcattg tc 762

<210> SEQ ID NO 17
<211> LENGTH: 788
<212> TYPE: DNA
<213> ORGANISM: Artificial Sequence
<220> FEATURE:
<223> OTHER INFORMATION: VH-linker-VL of anti DNP scFv (Ab-3)

<400> SEQUENCE: 17
ccaggtgcca catttgccca agtgctgacc cagactccat cgcctgtgtc tgcagctgtg 60
ggaggcacag tcaccatcag ttgccagtcc agtgagagtg tttatggtaa cagccgctta 120
gcctggtatc agcagaaacc agggcagtct cccaagctcc tgatctatta tgcatccact 180
ctggcatctg gggtcccttc gcggttcaaa ggcagtggat ctgggacaca gttcactctc 240
accattagcg acctggagtg tgacgatgct gcctcttact actgtcaagg cggttattat 300
agtggtaatc ttgatgcgct tgctttcggc ggagggaccg aggtggtggt cagaggtggc 360
ggagggggct ctggcggcgg aggatctggg ggagggggca gccagtgtca gcagctggag 420
cagtccggag gaggagccga aggaggcctg gtcaagcctg ggggatccct ggaactctgc 480
tgcaaagcct ctggattctc cctcagtagt agctactgca tatgttgggt ccgccaggct 540
ccagggaagg ggctggagtg gatcggatgc atttatgctg gtagtagtgg tagcacttac 600
tacgcgagct gggtgaatgg ccgattcact ctctccagag acattgacca gagcacaggt 660
tgcctacaac tgaacagtct gacagccgcg gacacggcca tgtattactg tgcgagagcc 720
ccctatagta gtggctgggt cctctacttt aacttgtggg gcccaggcac cctggtcatt 780
gtctcctc 788

<210> SEQ ID NO 18
<211> LENGTH: 789
<212> TYPE: DNA
<213> ORGANISM: Artificial Sequence
<220> FEATURE:
<223> OTHER INFORMATION: anti DNP scFv
VH-linker-VL of anti DNP scFv (Ab-3)

<400> SEQUENCE: 18

```
cagtgtcagc agctggagca gtccggagga ggagccgaag gaggcctggt caagcctggg      60
ggatccctgg aactctgctg caaagcctct ggattctccc tcagtagtag ctactgcata     120
tgttgggtcc gccaggctcc agggaagggg ctggagtgga tcggatgcat ttatgctggt     180
agtagtggta gcacttacta cgcgagctgg gtgaatggcc gattcactct ctccagagac     240
attgaccaga gcacaggttg cctacaactg aacagtctga cagccgcgga cacggccatg     300
tattactgtg cgagagcccc ctatagtagt ggctgggtcc tctactttaa cttgtggggc     360
ccaggcaccc tggtcattgt ctcctcaggc ggagggggct ctggcggcgg aggatctggg     420
ggagggggca gcccaggtgc cacatttgcc caagtgctga cccagactcc atcgcctgtg     480
tctgcagctg tgggaggcac agtcaccatc agttgccagt ccagtgagag tgtttatggt     540
aacagccgct tagcctggta tcagcagaaa ccagggcagt ctcccaagct cctgatctat     600
tatgcatcca ctctggcatc tggggtccct tcgcggttca aaggcagtgg atctgggaca     660
cagttcactc tcaccattag cgacctggag tgtgacgatg ctgcctctta ctactgtcaa     720
ggcggttatt atagtggtaa tcttgatgcg cttgctttcg gcggagggac cgaggtggtg     780
gtcagaggt                                                             789
```

<210> SEQ ID NO 19
<211> LENGTH: 15
<212> TYPE: PRT
<213> ORGANISM: Artificial Sequence
<220> FEATURE:
<223> OTHER INFORMATION: linker

<400> SEQUENCE: 19

```
Gly Gly Gly Gly Ser Gly Gly Gly Gly Ser Gly Gly Gly Gly Ser
1               5                   10                  15
```

<210> SEQ ID NO 20
<211> LENGTH: 229
<212> TYPE: PRT
<213> ORGANISM: Artificial Sequence
<220> FEATURE:
<223> OTHER INFORMATION: Long spacer: IgG4hinge-CH2(L235D)-CH3

<400> SEQUENCE: 20

```
Glu Ser Lys Tyr Gly Pro Pro Cys Pro Pro Cys Pro Ala Pro Glu Phe
1               5                   10                  15

Asp Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
```

-continued

```
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 21
<211> LENGTH: 119
<212> TYPE: PRT
<213> ORGANISM: Artificial Sequence
<220> FEATURE:
<223> OTHER INFORMATION: Medium spacer: IgG4 hinge-CH3

<400> SEQUENCE: 21

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 22
<211> LENGTH: 12
<212> TYPE: PRT
<213> ORGANISM: Artificial Sequence
<220> FEATURE:
<223> OTHER INFORMATION: Short spacer: IgG4 hinge

<400> SEQUENCE: 22

Glu Ser Lys Tyr Gly Pro Pro Cys Pro Pro Cys Pro
1               5                   10


<210> SEQ ID NO 23
<211> LENGTH: 28
<212> TYPE: PRT
<213> ORGANISM: Artificial Sequence
<220> FEATURE:
<223> OTHER INFORMATION: CD28tm

<400> SEQUENCE: 23

Met Phe Trp Val Leu Val Val Val Gly Gly Val Leu Ala Cys Tyr Ser
1               5                   10                  15
```

Leu Leu Val Thr Val Ala Phe Ile Ile Phe Trp Val
20 25

<210> SEQ ID NO 24
<211> LENGTH: 42
<212> TYPE: PRT
<213> ORGANISM: Artificial Sequence
<220> FEATURE:
<223> OTHER INFORMATION: 4-1BB

<400> SEQUENCE: 24

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 25
<211> LENGTH: 112
<212> TYPE: PRT
<213> ORGANISM: Artificial Sequence
<220> FEATURE:
<223> OTHER INFORMATION: CD3 zeta

<400> SEQUENCE: 25

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 26
<211> LENGTH: 21
<212> TYPE: PRT
<213> ORGANISM: Artificial Sequence
<220> FEATURE:
<223> OTHER INFORMATION: T2A

<400> SEQUENCE: 26

Gly Gly Gly Glu Gly Arg Gly Ser Leu Leu Thr Cys Gly Asp Val Glu
1 5 10 15

Glu Asn Pro Gly Pro
20

<210> SEQ ID NO 27
<211> LENGTH: 357
<212> TYPE: PRT
<213> ORGANISM: Artificial Sequence
<220> FEATURE:
<223> OTHER INFORMATION: GM-CSF receptor ss to EGFRt

<400> SEQUENCE: 27

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 28
<211> LENGTH: 187
<212> TYPE: PRT
<213> ORGANISM: Artificial Sequence
<220> FEATURE:
<223> OTHER INFORMATION: DHFRdm

<400> SEQUENCE: 28

-continued

```
Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 29
<211> LENGTH: 22
<212> TYPE: PRT
<213> ORGANISM: Artificial Sequence
<220> FEATURE:
<223> OTHER INFORMATION: GM-CSF signal Sequence

<400> SEQUENCE: 29

```
Met Leu Leu Leu Val Thr Ser Leu Leu Leu Cys Glu Leu Pro His Pro
1               5                   10                  15

Ala Phe Leu Leu Ile Pro
            20
```

ANTI-DINITROPHENOL CHIMERIC ANTIGEN RECEPTORS

CROSS-REFERENCE TO RELATED APPLICATIONS

This application is a U.S. National Phase Application of PCT International Application Number PCT/US2021/016177, filed on Feb. 2, 2021, designating the United States of America and published in the English language, which is an International Application of and claims the benefit of priority to U.S. Provisional Application No. 62/969,931, filed on Feb. 4, 2020. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-269NP, created Jul. 14, 2022, which is approximately 43 Kb in size. The information in the electronic format of the Sequence Listing is incorporated herein by reference in its entirety.

FIELD OF THE INVENTION

Embodiments provided herein include methods and compositions comprising anti-dinitrophenol chimeric antigen receptors (CARs). Some embodiments include nucleic acids encoding such CARs, polypeptides encoded by such nucleic acids, cells comprising such polypeptides, and methods utilizing such cells. Some embodiments also include the use of dinitrophenol (DNP) and derivatives thereof.

BACKGROUND OF THE INVENTION

Immunotherapy using adoptive cell transfer of chimeric antigen receptor (CAR) bearing T-cells is an effective approach to treat cancer. The structure of a CAR includes an antigen binding domain, a spacer domain, a transmembrane domain, and one or more co-stimulatory activation domains. CAR T cells may be prepared from T cells obtained from a patient or from a donor. In some instances, CARs function by binding to a specific antigen on a cell surface, which causes lysis of the antigen-bearing cell. Although considerable research has focused on the design of CAR ligand binding domains, which target desired cell surface antigens with reduced toxicity, there remains a need for additional CAR T cell-mediated therapies.

SUMMARY OF THE INVENTION

Some embodiments of the methods and compositions provided herein include a nucleic acid encoding a chimeric antigen receptor (CAR), wherein the CAR comprises: a ligand binding domain which specifically binds to a dinitrophenol (DNP) moiety; a spacer; a transmembrane domain; and an intracellular signaling domain.

In some embodiments, the ligand binding domain comprises an amino acid sequence having at least 90% identity to the amino acid sequence set forth in any one of SEQ ID NOs:01-12. In some embodiments, the ligand binding domain comprises the amino acid sequence set forth in any one of SEQ ID NOs:01-12.

In some embodiments, the ligand binding domain comprises an amino acid sequence having at least 90% identity to the amino acid sequence set forth in SEQ ID NOs:01, 02, 09, or 10. In some embodiments, the ligand binding domain comprises the amino acid sequences set forth in SEQ ID NOs:01, 02, 09, or 10.

In some embodiments, the spacer is selected from the group consisting of: a short spacer having a length of 12 consecutive amino acid residues or less but, preferably not 1 amino acid in length, a medium spacer having a length of 119 consecutive amino acid residues or less but, preferably not 1 amino acid in length, and a long spacer having a length greater than 119 consecutive amino acid residues.

In some embodiments, the spacer is selected from the group consisting of: a short spacer comprising an IgG4 hinge domain, a medium spacer comprising an IgG4 hinge-CH3 domain, and a long spacer comprising an IgG4 hinge—CH2-CH3 domain.

In some embodiments, the spacer is a long spacer having a length of at least 229 consecutive amino acid residues.

In some embodiments, the transmembrane domain comprises a CD28 transmembrane domain.

In some embodiments, the intracellular signaling domain comprises a portion of CD3 zeta and/or a portion of 4-1BB.

Some embodiments also include a polynucleotide encoding a selectable gene, a cell surface selectable marker, or a cleavable linker. In some embodiments, the selectable gene comprises a dihydrofolate reductase double mutant (DHFRdm). In some embodiments, the cell surface selectable marker is selected from the group consisting of a truncated EGFR (EGFRt), a truncated Her2 (Her2tG), and a truncated CD19 (CD19t). In some embodiments, the cleavable linker comprises a ribosome skip sequence is selected from the group consisting of P2A, T2A, E2A and F2A.

Some embodiments of the methods and compositions provided herein include a vector comprising any one of the nucleic acids provided herein. In some embodiments, the vector comprises a lentiviral vector.

Some embodiments of the methods and compositions provided herein include a method for preparing a population of cells for an infusion, comprising: introducing the nucleic acid of any one of the nucleic acids provided herein encoding an anti-DNP CAR into a cell; and culturing the cell under conditions suitable to obtain a population of cells sufficient for an infusion.

Some embodiments of the methods and compositions provided herein include a CAR encoded by any one of the nucleic acids provided herein.

Some embodiments of the methods and compositions provided herein include a cell comprising any one of the CARs provided herein.

In some embodiments, the cell is derived from a CD4+ T cell, a CD8+ T cell, a precursor T cell, or a hematopoietic stem cell. In some embodiments, the CD8+ T cell is a CD8+ cytotoxic T lymphocyte cell selected from the group consisting of a naïve CD8+ T cell, a central memory CD8+ T cell, an effector memory CD8+ T cell, and a bulk CD8+ T cell. In some embodiments, the central memory CD8+ T cell is positive for CD45RO and CD62L. In some embodiments, the CD4+ cell is a CD4+ helper T lymphocyte cell selected from the group consisting of a naïve CD4+ T cell, a central memory CD4+ T cell, an effector memory CD4+ T cell, and a bulk CD4+ T cell. In some embodiments, the naïve CD4+ T cell is positive for CD45RA and CD62L, and negative for CD45RO.

In some embodiments, the cell is ex vivo. In some embodiments, the cell is in vivo.

In some embodiments, the cell is mammalian. In some embodiments, the cell is human.

Some embodiments of the methods and compositions provided herein include a composition comprising: any one of the CARs provided herein; and a DNP moiety attached to a target cell, wherein the CAR is specifically bound to the DNP moiety.

In some embodiments, the DNP moiety is attached to the target cell via an antibody or antigen binding fragment thereof that binds to the target cell.

In some embodiments, the DNP moiety is attached to the target cell via a folate moiety.

In some embodiments, the DNP moiety is attached to a cell surface of the target cell via a lipid integrated into the cell surface. In some embodiments, the lipid comprises a polar head group and a hydrophobic group. In some embodiments, the polar head comprises a group selected from choline, phosphatidylcholine, phosphocholine, sphingomyelin, aphosphoethanolamine, a sugar residue, phosphatidyl serine, phosphatidyl inositol, a piperidine, or a trimethylarseno-ethyl-phosphate. In some embodiments, the hydrophobic group comprises an aliphatic chain or a terpenoid moiety. In some embodiments, the hydrophobic group comprises an ether linkage, wherein the ether linkage is between the polar head group and the aliphatic chain. In some embodiments, the aliphatic chain comprises a $C_{10-20}$ alkyl chain. In some embodiments, the lipid is a phospholipid ether (PLE).

In some embodiments, the target cell is a cancer cell. In some embodiments, the cancer cell is selected from the group consisting of a breast cancer cell, brain cancer cell, colon cancer cell, renal cancer cell, pancreatic cancer cell, and ovarian cancer cell.

In some embodiments, the target cell is ex vivo. In some embodiments, the target cell is in vivo.

In some embodiments, the target cell is mammalian. In some embodiments, the target cell is human.

Some embodiments of the methods and compositions provided herein include a method of treating or ameliorating a cancer in a subject comprising: administering any one of anti-DNP CAR T cells provided herein to the subject in combination with a composition comprising a DNP moiety.

In some embodiments, the cell is administered prior to administration of the composition. In some embodiments, the cell is administered subsequent to administration of the composition. In some embodiments, the cell is co-administered with the composition.

In some embodiments, the composition is adapted to target the cancer.

In some embodiments, the DNP moiety is attached to an antibody of antigen binding fragment thereof which specifically binds to the cancer.

In some embodiments, the DNP moiety is attached to a folate.

In some embodiments, the DNP moiety is attached to a lipid. In some embodiments, the lipid comprises a polar head group and a hydrophobic group. In some embodiments, the polar head comprises a group selected from choline, phosphatidylcholine, phosphocholine, sphingomyelin, aphosphoethanolamine, a sugar residue, phosphatidyl serine, phosphatidyl inositol, a piperidine, or a trimethylarseno-ethyl-phosphate. In some embodiments, the hydrophobic group comprises an aliphatic chain or a terpenoid moiety. In some embodiments, the hydrophobic group comprises an ether linkage, wherein the ether linkage is between the polar head group and the aliphatic chain. In some embodiments, the aliphatic chain comprises a $C_{10-20}$ alkyl chain. In some embodiments, the lipid is a PLE.

In some embodiments, the cancer comprises a target cell selected from the group consisting of a breast cancer cell, brain cancer cell, colon cancer cell, renal cancer cell, pancreatic cancer cell, and ovarian cancer cell.

In some embodiments, the cell is autologous to the subject.

In some embodiments, the subject is mammalian. In some embodiments, the subject is human.

Some embodiments of the methods and compositions provided herein include use of any one of anti-DNP CAR T cells provided herein in combination with a composition comprising a DNP moiety to treat a cancer in a subject.

Some embodiments of the methods and compositions provided herein include use of any one of anti-DNP CAR T cells provided herein in combination with a composition comprising a DNP moiety in the manufacture of a medicament a to treat a cancer in a subject.

Some embodiments of the methods and compositions provided herein include any one of anti-DNP CAR T cells provided herein for use in a medicament.

DETAILED DESCRIPTION

Figure 1:
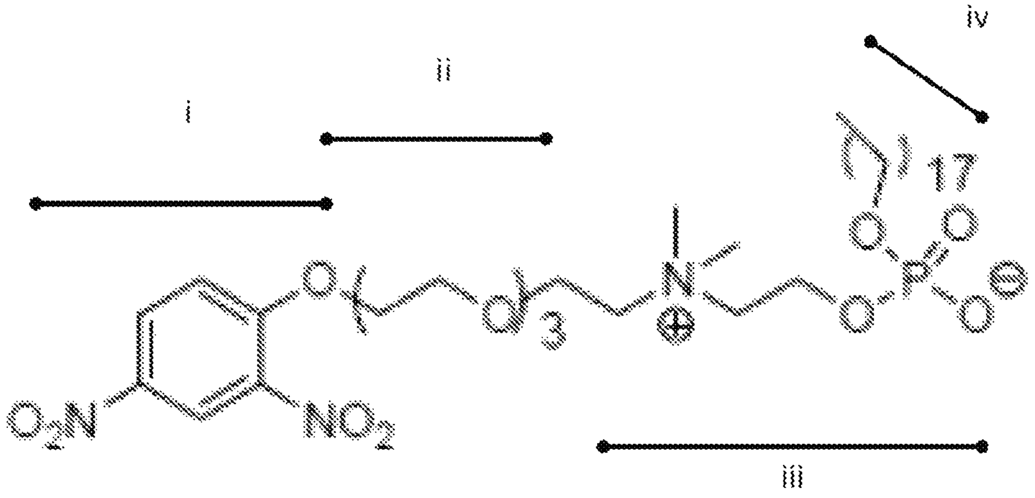
FIG. 1 depicts an embodiment of a DNP phospholipid ether (DNP-PLE) which includes: (i) a DNP moiety; (ii) a polyethylene glycol (PEG) moiety; (iii) a polar head moiety; and (iv) a hydrophobic tail moiety.

Embodiments provided herein include methods and compositions comprising anti-dinitrophenol chimeric antigen receptors (CARs). Some embodiments include nucleic acids encoding such CARs, polypeptides encoded by such nucleic acids, cells comprising such polypeptides, and methods utilizing such cells. Some embodiments also include the use of dinitrophenol (DNP) and derivatives thereof.

While the adoptive transfer of transgene modified T cells has been successful in select settings, such as CD19 B cell lineage malignancies, these therapies have proved difficult to genericize to other cancer types because of the lack of a single target antigen that is present on all forms of cancer but not normal, healthy cells. The development of CAR T cell therapies, which treat the multitude of cancers afflicting humans, has been hampered by the onerous task of identifying and vetting tens of hundreds of antigens presented on cancer cells, e.g., CAR targets. In some embodiments described herein, this problem is addressed by using a DNP phospholipid ether (DNP-PLE), which associates with tumor cells and displays a unique target molecule for T cells bearing DNP-specific CARS to interact with and thereby lyse the DNP-presenting tumor cells. By this approach, one can eliminate the need to identify and validate tens of hundreds of unique antigen specific CARs.

Some embodiments provided herein include CARS comprising a specificity or a selected affinity or avidity for a DNP moiety. In some embodiments a DNP moiety is joined to a molecule, which can be associated with or bound to the surface of a tumor cell. In some embodiments, the molecule is a PLE. In some embodiments, the molecule can include an antibody or antigen-binding fragment thereof which specifically binds to a cell. In some embodiments, methods of redirected anti-tumor T cell reactivity can then be performed using said DNP-PLE, or other DNP-molecule, and T cells having said CARS. In some embodiments, the DNP-PLE is a synthetic molecule having a structure designed to integrate into the plasma membrane of tumor cells in a manner that allows for the molecule's DNP moiety to be adjacent to the outer leaflet of the plasma membrane and displayed in the extracellular space in an orientation or proximity that allows for a desired interaction with a T cell bearing a CAR having a desired affinity, specificity, or avidity for the DNP moiety. Similarly, in some embodiments, the CARS described herein have a unique structure designed to allow the anti-DNP ligand binding domain of the receptor to be displayed on the T cell plasma membrane in an orientation or proximity that allows for a desired interaction or avidity with the DNP-PLE-bearing tumor cells. Thus, in some embodiments, the DNP-PLE molecule and CARs described herein imbue therapeutically important attributes and the use of such DNP-PLE molecules with or without the anti-DNP specific CARs as a medicament are contemplated. Stated differently, any one or more of the CARs and the DNP-PLE molecules described herein are useful for the treatment or amelioration of a human disease or condition, such as a cancer.

Additional embodiments relate to CARs that target and interact with a DNP moiety joined to a PLE molecule, which can be constitutively expressed, or placed under regulated control in a cell, preferably a T cell, nucleic acids encoding said CARS, cells having said nucleic acids and CARS, preferably T cells, and methods of making and using these compositions to treat a disease such as cancer in humans. Some embodiments of the methods and compositions provided herein include aspects disclosed in WO 2018/148224; WO 2019/156795; WO 2019/144095; U.S. 2019/0224237; and PCT/US2019/044981, which are each hereby expressly incorporated herein by reference in its entirety.

Definitions

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), or fragments generated by any of ligation, scission, endonuclease action, or exonuclease action. Nucleic acid molecules can be composed of monomers that are naturally-occurring nucleotides (such as DNA or RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars or carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate, and the like. The term "nucleic acid molecule" also includes "peptide nucleic acids," which comprise naturally-occurring or modified nucleic acid bases attached to a polyamide backbone. Nucleic acids can be either single stranded or double stranded. "Coding for" is used herein to refer to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence. "Specific" or "Specificity" can refer to the characteristic of a ligand for a binding partner or alternatively, a binding partner for a ligand, and can include complementary shape, charge or hydrophobic specificity for binding. Specificity for binding can include stereospecificity, regioselectivity and/or chemoselectivity. In some embodiments, a method of making a nucleic acid encoding a chimeric antigen receptor is provided such that a nucleic acid encoding a chimeric antigen receptor is generated that is specific for a DNP moiety joined to or associated with a PLE molecule, which can be associated or joined to a tumor cell.

A "vector" or "construct" is a nucleic acid used to introduce heterologous nucleic acids into a cell that can also have regulatory elements to provide expression of the heterologous nucleic acids in the cell. Vectors include but are not limited to plasmid, minicircles, yeast, or viral genomes. In some embodiments, the vectors are plasmid, minicircles, viral vectors, DNA or mRNA. In some embodiments, the vector is a lentiviral vector or a retroviral vector. In some embodiments, the vector is a lentiviral vector.

"Chimeric receptor" as used herein refers to a synthetically designed receptor comprising a ligand binding domain of an antibody or other protein sequence that binds to a target molecule and is linked via a spacer domain to one or more intracellular signaling domains of a T cell or other receptors, such as a costimulatory domain. Chimeric receptors can also be referred to as artificial T cell receptors, chimeric T cell receptors, chimeric immunoreceptors, or chimeric antigen receptors (CARs). These receptors can be used to graft the specificity of a monoclonal antibody or binding fragment thereof or other ligand binding domain onto a T-cell, wherein transfer of the required coding sequences is facilitated by viral vectors, such as a retroviral vector or a lentiviral vector. CARs are e.g., genetically engineered T-cell receptors designed to redirect T-cells to target cells that express or display the specific cell-surface antigen to which the CAR is directed. T-cells can be removed from a subject and modified so that they express receptors that are specific for a desired antigen by a process called "adoptive cell transfer." The T-cells are then reintroduced into the patient, wherein they recognize, target and bind to molecules displaying the antigen presented on cells. These CARs are engineered receptors that graft a selected specificity onto an immune receptor cell. The term chimeric antigen receptors or "CARs" is also considered by some investigators to include the antibody or antibody fragment, the spacer, signaling domain(s), and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements.

A "single-chain variable fragment," (scFv) is a fusion protein that can have variable regions of the heavy (VH) and light chains (VL) of immunoglobulins, connected with a short linker peptide of ten to 25 amino acids. The short linker peptide can comprise 10, 11, 12, 13, 14, 15, 16, 17, 18, 19, 20, 21, 22, 23, 24, or 25 amino acids or any number of amino acids within a range defined by any two aforementioned values. The linker is usually rich in glycine for flexibility, as well as, serine or threonine for solubility, and can either connect the N-terminus of the VH with the C-terminus of the VL, or vice versa. This protein retains the specificity of the original immunoglobulin, despite removal of the constant regions and the introduction of the linker. The scFv can be specific for an antigen. "Antigen" or "Ag" as used herein, refers to a molecule that provokes an immune response. This immune response can involve either antibody production, or the activation of specific immunologically-competent cells, or both. An antigen can be generated, synthesized, produced recombinantly or can be derived from a biological sample. Such a biological sample can include, but is not limited to a tissue sample, a tumor sample, a cell or a biological fluid such, for example, blood, plasma or ascites fluid. In some embodiments herein, a composition is provided, wherein the composition comprises cells, preferably T cells, manufactured by any one of the alternative methods herein. In some embodiments, the cells, preferably T cells, comprise a chimeric antigen receptor, wherein the chimeric antigen receptor comprises a scFv that is specific for a DNP moiety joined to or associated with a PLE molecule, which can be associated or joined to a tumor cell.

"Antigen specific binding domains" can include protein or protein domains that specifically bind to an epitope on a protein at a low or high binding affinity (fM to mM binding capacity). In some embodiments, the fusion protein comprises a protein or portion thereof that modulate an immune response. In some embodiments, the protein comprises an antigen specific binding domain.

Several types of "spacers" are described herein. With regard to CARs, a spacer for a CAR refers to a polypeptide spacer, which spacer length is configured to or is selected for its ability to promote an increase in binding or interaction with a chimeric antigen receptor or to reduce or minimizes an adverse side effect associated with CAR T cell therapy. In some embodiments, a short spacer domain of a CAR has 12 or about 12 amino acids or less but greater than 1 amino acid and comprises all or a portion of a IgG4 hinge region sequence or variant thereof. In some embodiments, an intermediate (medium) spacer domain of a CAR has 119 or about 119 amino acids or less but greater than 1 amino acid and comprises all or a portion of a IgG4 hinge region sequence and a CH3 region or variant thereof. In some embodiments, a long spacer domain of a CAR has 229 or about 229 amino acids or less but greater than 1 amino acid and comprises all or a portion of a IgG4 hinge region sequence, a CH2 region, and a CH3 region or variant thereof. In some embodiments, the spacer length or sequence or both are selected based on a desired avidity or interaction with a DNP moiety joined to or associated with a PLE molecule, which can be associated or joined to a tumor cell.

A "transmembrane domain" is a region of a protein that is hydrophobic that can reside in the bilayer of a cell to anchor a protein that is embedded to the biological membrane. Without being limiting, the topology of the transmembrane domain can be a transmembrane alpha helix. In some embodiments of the method of making genetically modified T-cells, which have a chimeric antigen receptor, the vector comprises a sequence encoding a transmembrane domain. In some embodiments of the method, the transmembrane domain comprises a CD28 transmembrane sequence or a fragment thereof that is a length of 10, 11, 12, 13, 14, 15, 16, 17, 18, 19, 20, 21, 22, 23, 24, 25, 26, 27, or 28 amino acids or a length within a range defined by any two of the aforementioned lengths. In some embodiments of the method, the CD28 transmembrane sequence or fragment thereof comprise 28 amino acids in length. In some embodiments, the chimeric receptor comprises a transmembrane domain. The transmembrane domain provides for anchoring of the chimeric receptor in the membrane.

"Co-stimulatory domain," or "intracellular signaling domain" has its plain and ordinary meaning when read in light of the specification, and may include but is not limited to, for example, a signaling moiety that provides to T cells a signal which, in addition to the primary signal provided by for instance the CD3 zeta chain of the TCR/CD3 complex, mediates a T cell response, including, but not limited to, activation, proliferation, differentiation, or cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83. In some embodiments, the co-stimulatory domain is an intracellular signaling domain that interacts with other intracellular mediators to mediate a cell response including any one or more of activation, proliferation, differentiation or cytokine secretion.

A "marker sequence," as described herein, encodes a protein that is used for selecting or tracking a protein or cell that has a protein of interest. In the embodiments described herein, the fusion protein provided can comprise a marker sequence that can be selected in experiments, such as flow cytometry. In some embodiments, the marker is the protein Her2tG, CD19t, or EGFRt.

A "ribosome skip sequence" as described herein refers to a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. As described herein, this is the "linker" sequence. In some embodiments of the nucleic acids provided herein, the nucleic acids comprise a ribosome skip sequence between the sequence for the chimeric antigen receptor and the sequence of the marker protein, such that the proteins are co-expressed and not linked by a peptide bond. In some embodiments, the ribosome skip sequence is a P2A, T2A, E2A or F2A sequence. In some embodiments, the ribosome skip sequence is a T2A sequence. In some embodiments, there are ribosome skip sequences between the two chimeric antigen receptors and a second ribosome skip sequence between one of the chimeric antigen receptors and the marker.

As used herein, 2,4-Dinitrophenol (2,4-DNP or simply DNP) is an organic compound with the formula $HOC_6H_3(NO_2)_2$, and has its plain and ordinary meaning when read in light of the specification. DNP is used as an antiseptic, non-selective bioaccumulating pesticide, herbicide, among others. It is a chemical intermediate in the production of sulfur dyes, wood preservatives, and picric acid. In some embodiments herein, DNP is a target moiety on a lipid that is recognized and bound by a chimeric antigen receptor. In some embodiments, the hapten is DNP or derivatives thereof. In some embodiments, the lipid is a phospholipid, such as a phospholipid ether (PLE).

"Lipid" as described herein, is a class of organic compounds that comprise carbon chains, fatty acids or a fatty acid derivative that is typically insoluble in water but can integrate into or mix with hydrophobic or organic solvents. Without being limiting, lipids can include fats, waxes, fat soluble vitamins, monoglycerides, diglycerides, triglycerides, sphingolipids, cerebrosides, ceramides, or phospholipids. Described herein are amphiphilic lipids that can have a polar head group and a hydrophobic moiety or hydrophobic group. "Hydrophobic group" or hydrophobic moiety, as described herein, is a molecule or a part of a molecule that is repelled from a mass of water and tends to be non-polar. This can include alkanes, oils or fats. Without being limiting, lipids can be glycerolipids, glycerophospholipids, sphingolipids, sterol lipids, prenol lipids, saccharolipids or polyketides. In the embodiments herein a complex is provided, wherein the complex comprises a lipid. In some embodiments, the lipid comprises a polar head group and a hydrophobic moiety. In some embodiments, the hydrophobic moiety is a hydrophobic carbon tail. In some embodiments the hydrophobic carbon tail is saturated or unsaturated. In some embodiments, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some embodiments, the hydrophobic moiety is a steroid or a cholesterol. In some embodiments, the lipid comprises a glycerolipid, glycerophospholipid, sphingolipid, sterol lipid, prenol lipid, saccharolipid or polyketide. In some embodiments, the lipid is a phospholipid ether. In some embodiments, the lipid contains branched alkyl tails.

In some embodiments, the lipid is a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, or various sugar monomers or dimers, yielding cerebrosides and globosides, respectively. Cerebrosides and globosides are collectively known as glycosphingolipids. In some embodiments, the lipid is a glycosphingolipid.

As provided herein, the lipid comprises a polar head group and a hydrophobic group. In some embodiments, the hydrophobic group comprises a fatty acid such as an aliphatic chain. The fatty acid can be saturated or unsaturated. In some embodiments, the hydrophobic group comprises an alkyl, alkenyl or alkynyl group. In some embodiments, the hydrophobic group comprises a terpenoid lipid, such as a steroid or cholesterol. In some embodiments, the hydrophobic group comprises an ether linkage, wherein the ether linkage is between the polar head group and the aliphatic chain. In some embodiments, the lipid is a phospholipid ether. In some embodiments, the polar head comprises a choline, a phosphatidylcholine, sphingomyelin, phosphoethanolamine group, an oligosaccharide residue, a sugar residue, phosphatidyl serine or phosphatidyl inositol. In some embodiments, the sugar is a glycerol or sugar alcohol.

In some embodiments, the lipid is a single chain alkylphospholipid.

In some embodiments, the lipid comprises a structure of synthetic alkylphospholipids, such as edelfosine, perifosine or erucylphosphocholine. In some embodiments, the lipid is a lysophosphatidylcholine, edlfosine, erucylphosphocholine, D-21805 or perfisone. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; hereby expressly incorporated by reference in its entirety). In some embodiments of the lipids described herein, a choline within the polar head group can be substituted with a piperidine moiety. In some embodiments, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; hereby expressly incorporated by reference in its entirety).

In some embodiments, the lipids provided herein are synthetic and structurally related anti-tumor agents that interact with a cell membrane. These types of synthetic lipids are alkylphospholipids and are described by e.g., van Blitterswijk et al. ("Anticancer mechanisms and clinical application of alkylphopholipids" Biochimica et al. Biophysica Acta 1831 (2013)663-674; hereby incorporated by reference in its entirety herein). Without being limiting, the synthetic alkylphospholipids can include edelfosine, miltefosine, perifosine, erucylphosphocholine or Erufosine. In some embodiments, the lipid is edelfosine, miltefosine, perifosine, erucylphosphocholine or Erufosine. In some embodiments, the lipid is a stable analog of lysophosphatidylcholine. In some embodiments, the lipid is a thio-ether variant of edelfosine, or 1-hexadecylthio-2-methoxymethyl-rac-glycero-3-phosphocholine. In some alternatives, the lipid is LysoPC, edelfosine, Ilmofosine, Miltefosine, Perifosine, Erucylphosphocholine, or Erufosine.

"Polar-head group" as described herein, is the hydrophilic group of a lipid, such as a phospholipid. "Phospholipids" as described herein are a specific class of lipids that can form lipid bilayers due to their amphiphilic characteristic. The phospholipid molecule comprises at least one hydrophobic fatty acid "tail" and a hydrophilic "head" or "polar-head group." In the alternative herein, the phospholipid or phospholipid ether comprises a polar-head group. In some embodiments, the polar-head group comprises phosphocholine, a piperidine moiety or a trimethylarseno-ethyl-phosphate moiety. In some embodiments, the lipid comprises a target moiety, preferably DNP, and the CAR is joined to or is configured to join to said lipid through an interaction with said target moiety. In some embodiments, the lipid comprises a polar-head group (e.g., comprising an aromatic ring) and a carbon alkyl chain. In some embodiments herein, a complex is provided, wherein the complex comprises one or more of said lipids. In some embodiments, the lipid comprises a polar head group. In some embodiments, the lipid is a phospholipid ether. In some embodiments, the phospholipid ether comprises a target moiety, preferably DNP, and the CAR is joined to or is configured to join to said phospholipid ether through an interaction and/or binding with said target moiety. In some embodiments, the phospholipid ether comprises a polar-head group and a carbon alkyl chain. In some embodiments, the polar head group comprises a choline, a phosphatidylcholine, sphingomyelin, phosphoethanolamine group, an oligosaccharide residue, a sugar residue, phosphatidyl serine or phosphatidyl inositol. In some embodiments, the polar head group comprises phosphocholine, a piperidine moiety or a trimethylarsenoethyl-phosphate moiety. In some embodiments, the lipid is a phospholipid ether (PLE). In some embodiments, the sugar is a glycerol or sugar alcohol. In some embodiments, the polar head group comprises a sugar group. In some embodiments, the lipid comprises a mannose-containing head group. In some embodiments, the polar head group comprises sphingosine. In some embodiments, the polar head group comprises a glucose. In some embodiments, the polar head group comprises a di-, tri- or tetra-saccharide. In some embodiments, the lipid is a glucosylcerebroside. In some embodiments, the lipid is a lactosylceramide. In some embodiments, the lipid is a glycolipid. In some embodiments, the glycolipid comprises sugar units, such as n-glucose, n-galactose or N-actyl-n-galactosamine. In some embodiments, the lipid comprises a hydrocarbon ring such as a sterol.

In some embodiments, the polar head group of the lipid comprises glycerol or a sugar alcohol. In some embodiments, the polar head group of the lipid comprises a phosphate group. In some embodiments, the polar head group of the lipid comprises choline. In some embodiments, the lipid is a phosphatidylethanolamine. In some embodiments, the lipid is a phosphatidylinositol. In some embodiments, the lipid comprises a sphingoid base backbone. In some embodiments, the lipid comprises a sterol lipid, such as cholesterol or its derivatives. In some embodiments, the lipid comprises saccharolipids. In some embodiments, the polar head group comprises choline, phosphate or glycerol.

In some embodiments, the lipid is a glycolipid. In some embodiments, the lipid comprises a sugar. In some embodiments, the lipid is derived from sphingosine. In some embodiments, the lipid is a glycerol-glycolipid or a sphingo-glycolipid.

In some embodiments, the lipid is an ether lipid with branched hydrophobic chains.

"Terpenoid" as described herein, is a molecule that is derived from five carbon isoprene units. Steroids and sterols can be produced from terpenoid precursors. For example, steroids and cholesterol can be biosynthesized by terpenoid precursors.

"Phospholipid ether" (PLE) as described herein is a lipid in which one or more of the carbon atoms on a polar head group are bonded to an alkyl chain via an ether linkage, as opposed to the more common ester linkage. In some embodiments, the polar head group is a glycerol.

Several types of "spacers" are described herein and with regards to lipids, a lipid can comprise a spacer e.g., bound to the polar-head group of the lipid, which separates the target moiety, preferably DNP, from the lipid and a cell that is joined to or associates with said lipid so as to achieve a desired orientation or degree of freedom from steric hindrance. The spacer of the lipid can comprise a PEG spacer, a Hapten spacer, a small peptide or an alkane chain. In some embodiments, the hapten spacer comprises two haptens (hapten (2×) spacer). In some embodiments, the lipid comprises a hydrophobic group, such as an alkane chain. In some embodiments, the alkane chain can comprise 2, 3, 4, 5, 6, 7, 8, 9, 10, 11, 12, 13, 14, 15, 16, 17, or 18 carbons, or any number of carbons between a range defined by any two aforementioned values. In some embodiments, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values. Preferably, the length and type of spacer is selected to display the target moiety, preferably DNP, in an orientation or proximity that allows for a desired affinity or avidity to an anti-DNP CAR displayed on a cell, such as a T cell.

T-cells" or "T lymphocytes" as used herein, can be from any mammalian species, preferably primate, including monkeys, dogs, and humans. In some embodiments, the T-cells are allogeneic (from the same species but different donor) as the recipient subject; in some embodiments the T-cells are autologous (the donor and the recipient are the same); in some embodiments the T-cells are syngeneic (the donor and the recipients are different but are identical twins).

In some embodiments, the T cells are preferably "memory" T cells ($T_M$ cells) that are antigen-experienced. In some embodiments, the cell is a precursor T cell. In some embodiments, the precursor T cell is a hematopoietic stem cell. In some embodiments, the cell is a CD8+ T cytotoxic lymphocyte cell selected from the group consisting of naïve CD8+ T cells, central memory CD8+ T cells, effector memory CD8+ T cells and bulk CD8+ T cells. In some embodiments, the cell is a CD4+ T helper lymphocyte cell that is selected from the group consisting of naïve CD4+ T cells, central memory CD4+ T cells, effector memory CD4+ T cells, and bulk CD4+ T cells.

"Cytotoxic T lymphocyte" (CTL), as used herein, refers to a T lymphocyte that expresses CD8 on the surface thereof (e.g., a $CD8^+$ T-cell). In some embodiments, such cells are preferably "memory" T-cells ($T_M$ cells) that are antigen-experienced. In some embodiments, a cell for fusion protein secretion is provided. In some embodiments, the cell is a cytotoxic T lymphocyte. "Central memory" T-cell (or "$T_{CM}$") as used herein, refers to an antigen experienced CTL that expresses CD62L, CCR-7 and/or CD45RO on the surface thereof, and does not express or has decreased expression of CD45RA, as compared to naive cells. In some embodiments, a cell for fusion protein secretion is provided. In some embodiments, the cell is a central memory T-cell ($T_{CM}$).

In some embodiments, the central memory cells are positive for expression of CD62L, CCR7, CD28, CD127, CD45RO, and/or CD95, and may have decreased expression of CD54RA, as compared to naïve cells. "Effector memory" T-cell (or "$T_{EM}$") as used herein refers to an antigen experienced T-cell that does not express or has decreased expression of CD62L on the surface thereof, as compared to central memory cells, and does not express or has a decreased expression of CD45RA, as compared to naïve cell. In some embodiments, a cell for fusion protein secretion is provided. In some embodiments, the cell is an effector memory T-cell.

In some embodiments, effector memory cells are negative for expression of CD62L and/or CCR7, as compared to naïve cells or central memory cells, and may have variable expression of CD28 and/or CD45RA.

"Naïve T-cells" as used herein, refers to a non-antigen experienced T lymphocyte that expresses CD62L and/or CD45RA, and does not express CD45RO-, as compared to central or effector memory cells. In some embodiments, a cell for fusion protein secretion is provided. In some embodiments, the cell is a naïve T-cell. In some embodiments, naïve CD8+ T lymphocytes are characterized by the expression of phenotypic markers of naïve T-cells including CD62L, CCR7, CD28, CD127, and/or CD45RA.

"T-cells" or "T lymphocytes" as used herein can be from any mammalian, preferably primate, species, including monkeys, dogs, and humans. In some embodiments the T-cells are allogeneic (from the same species but different donor) as the recipient subject; in some embodiments the T-cells are autologous (the donor and the recipient are the same); in some embodiments the T-cells are syngeneic (the donor and the recipients are different but are identical twins).

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative ($CD4^-CD8^-$) cells. As they progress through their development, they become double-positive thymocytes ($CD4^+CD8^+$), and finally mature to single-positive ($CD4^+$ $CD8^-$ or $CD4^-CD8^+$) thymocytes that are then released from the thymus to peripheral tissues.

As described herein, "CD8 T-cells" or "killer T-cells" are T-lymphocytes that can kill cancer cells, cells that are infected with viruses or cells that are damages. CD8 T-cells recognize specific antigens, or a protein that is capable of stimulating an immune response and is produced by cancer cells or viruses. If the T-cell receptor of the CD8 T-cell recognizes the antigen, the CD8 T-cell can bind to the presented antigen and destroy the cell.

"Central memory T-cell" ($T_{CM}$) as used herein refers to an antigen experienced CTL that expresses CD62L or CCR-7 and CD45RO on the surface thereof and does not express or has decreased expression of CD45RA as compared to naïve cells. In some embodiments, central memory cells are positive for expression of CD62L, CCR7, CD28, CD127, CD45RO, and/or CD95, and have decreased expression of CD54RA as compared to naïve cells. "Effector memory" T-cell (or "$T_{EM}$") as used herein refers to an antigen experienced T-cell that does not express or has decreased expression of CD62L on the surface thereof as compared to central memory cells, and does not express or has decreased expression of CD45RA as compared to naïve cell. In some embodiments, effector memory cells are negative for expression of CD62L and/or CCR7, as compared to naïve cells or central memory cells, and have variable expression of CD28 and/or CD45RA. "Effector T-cells" ($T_E$ cells) as used herein, refers to antigen experienced cytotoxic T lymphocyte cells that do not express or have decreased expression of CD62L, CCR7, and/or CD28, and are positive for granzyme B and/or perforin, as compared to central memory or naïve T-cells. In some embodiments, a cell for fusion protein secretion is provided. In some embodiments, the cell is an effector T-cell. In some embodiments, the cell does not express or have decreased expression of CD62L, CCR7, and/or CD28, and are positive for granzyme B and/or perforin, as compared to central memory or naïve T-cells.

"Combination therapy" as described herein, refers to a therapy that uses more than one medication or modality for a therapy Combination therapy, for example, can also refer to multiple therapies for a single disease, and often all the therapies are pharmaceutical product combinations. Combination therapy can also involve prescribing and administering separate drugs in which the dosage can also have more than one active ingredient. In some embodiments, a combination therapy is provided, wherein the combination therapy comprises administering a genetically modified immune cell for modifying a tumor microenvironment. In some embodiments, the combination therapy comprises administering a genetically modified immune cell for modulating the suppression of the immune response in a tumor microenvironment. In some embodiments, the combination therapy comprises administering a genetically modified immune cell for minimizing the proliferation of tumor and suppressive cells in a subject in need thereof e.g. a human. In some embodiments, the combination therapy comprises administering a genetically modified immune cell for increasing the efficiency of an anti-cancer therapy, anti-infection therapy, antibacterial therapy, anti-viral therapy, or anti-tumoral therapy in a subject in need thereof e.g., a human. In some embodiments, the combination therapy further comprises administration of an inhibitor. In some embodiments, the inhibitor is not an enzymatic inhibitor. In some embodiments, the inhibitor is an enzymatic inhibitor. In some embodiments, the combination therapy comprises administering a therapeutic dose of an inhibitor or an antibody or a binding fragment thereof. These antibodies or binding fragments thereof can be humanized in some embodiments. In some embodiments, the combination therapy can further comprise administering a CAR bearing T-cell to a subject in need e.g., a human.

"Subject" or "patient," as described herein, refers to any organism upon which the embodiments described herein may be used or administered, e.g., for experimental, diagnostic, prophylactic, and/or therapeutic purposes. Subjects or patients include, for example, animals. In some embodiments, the subject is mice, rats, rabbits, non-human primates, or humans. In some embodiments, the subject is a cow, sheep, pig, horse, dog, cat, primate or a human.

"Cancer," as described herein, is a group of diseases involving abnormal cell growth with the potential to invade or spread to other parts of the body. Subjects that can be addressed using the methods described herein include subjects identified or selected as having cancer, including but not limited to colon, lung, liver, breast, renal, prostate, ovarian, skin (including melanoma), bone, leukemia, multiple myeloma, or brain cancer, etc. Such identification and/or selection can be made by clinical or diagnostic evaluation. In some embodiments, the tumor associated antigens or molecules are known, such as melanoma, breast cancer, brain cancer, squamous cell carcinoma, colon cancer, leukemia, myeloma, or prostate cancer. Examples include but are not limited to B cell lymphoma, breast cancer, brain cancer, prostate cancer, and/or leukemia. In some embodiments, one or more oncogenic polypeptides are associated with kidney, uterine, colon, lung, liver, breast, renal, prostate, ovarian, skin (including melanoma), bone, brain cancer, adenocarcinoma, pancreatic cancer, chronic myelogenous leukemia or leukemia.

In some embodiments, a method of treating, ameliorating, or inhibiting one or more of the aforementioned cancers in a subject is provided. In some embodiments, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some embodiments, the subject that receives one of the therapies set forth herein e.g., DNP-PLE and T cells having a CAR with a selective avidity for DNP as described herein, is also selected to receive an additional cancer therapy, which can include a cancer therapeutic, radiation, chemotherapy, or a cancer therapy drug. In some embodiments, the cancer therapy drug provided comprises Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid.

"Tumor microenvironment" as described herein is a cellular environment, wherein a tumor exists. Without being limiting, the tumor microenvironment can include surrounding blood vessels, immune cells, fibroblasts, bone marrow-derived inflammatory cells, lymphocytes, signaling molecules or the extracellular matrix (ECM).

Certain Nucleic Acids Encoding CARs

Some embodiments of the methods and compositions provided herein include one or more nucleic acids encoding a CAR specific for a DNP moiety associated with or joined to a PLE molecule. In some embodiments, the DNP moiety is associated or joined to an antibody or a folate. In some embodiments, the DNP moiety is in an orientation or proximity on an extracellular cell surface that allows for a desired affinity or avidity to the anti-DNP CAR, such as a T cell or a component of said CAR, such as a ligand binding domain. In some embodiments, the CAR comprises a selected ligand binding domain, which binds to a DNP moiety, a selected spacer of a desired length, a transmembrane domain; and an intracellular signaling domain(s) and, preferably said CAR is displayed on the surface of a T cell in an orientation that promotes or obtains a desired affinity or avidity to DNP-PLE, which may be associated with or joined to a tumor cell.

In some embodiments, one or more nucleic acids encode a ligand binding domain of one or more CARs set forth herein, which comprises an scFv domain comprising a VH sequence, and VL sequence derived from an antibody. In some embodiments, the VH and VL sequences are joined together via a linker. TABLE 1 lists example embodiments for a series of CARs, and TABLE 2 lists sequences for components of certain CARs. Example embodiments of VH sequences, VL sequences and linkers encoded by one or more of the nucleic acids set forth herein are listed in TABLE 2. In some embodiments, the one or more nucleic acids encoding a ligand binding domain of one or more CARs set forth herein encodes a ligand binding domain that comprises an amino acid sequence having at least 70%, 80%, 90%, 95%, 96%, 97%, 98%, 99% or 100% identity to the amino acid sequence set forth in any one of SEQ ID NOs:01-12. In some embodiments, the one or more nucleic acids encode a ligand binding domain that comprises the amino acid sequence set forth in any one of SEQ ID NOs:01-12. In some embodiments, the one or more nucleic acids encode a ligand binding domain that comprises an amino acid sequence having at least 70%, 80%, 90%, 95%, 96%, 97%, 98%, 99% or 100% identity to the amino acid sequence set forth in SEQ ID NOs:01, 02, 09, or 10.

TABLE 1

| Ligand binding domain derived from scFv | Spacer | Transmembrane domain | Co-stimulatory domain |
|---|---|---|---|
| VH-linker-VL of Ab-1 (1BAF) | short | CD28tm | 41BB and CD3-zeta |
| VH-linker-VL of Ab-1 (1BAF) | medium | CD28tm | 41BB and CD3-zeta |
| VH-linker-VL of Ab-1 (1BAF) | long | CD28tm | 41BB and CD3-zeta |
| VL-linker-VH of Ab-1 (1BAF) | short | CD28tm | 41BB and CD3-zeta |
| VL-linker-VH of Ab-1 (1BAF) | medium | CD28tm | 41BB and CD3-zeta |
| VL-linker-VH of Ab-1 (1BAF) | long | CD28tm | 41BB and CD3-zeta |
| VH-linker-VL of Ab-2 (XC) | short | CD28tm | 41BB and CD3-zeta |
| VH-linker-VL of Ab-2 (XC) | medium | CD28tm | 41BB and CD3-zeta |
| VH-linker-VL of Ab-2 (XC) | long | CD28tm | 41BB and CD3-zeta |
| VL-linker-VH of Ab-2 (XC) | short | CD28tm | 41BB and CD3-zeta |
| VL-linker-VH of Ab-2 (XC) | medium | CD28tm | 41BB and CD3-zeta |
| VL-linker-VH of Ab-2 (XC) | long | CD28tm | 41BB and CD3-zeta |
| VH-linker-VL of Ab-3 | short | CD28tm | 41BB and CD3-zeta |
| VH-linker-VL of Ab-3 | medium | CD28tm | 41BB and CD3-zeta |
| VH-linker-VL of Ab-3 | long | CD28tm | 41BB and CD3-zeta |
| VL-linker-VH of Ab-3 | short | CD28tm | 41BB and CD3-zeta |
| VL-linker-VH of Ab-3 | medium | CD28tm | 41BB and CD3-zeta |
| VL-linker-VH of Ab-3 | long | CD28tm | 41BB and CD3-zeta |

TABLE 2

| SEQ ID NO | Sequence |
|---|---|
| SEQ ID NO: 01 VH of anti DNP scFv (Ab-1; 1BAF) | DVQLQESGPGLVKPSQSQSLTCTVTGYSITSDYAWNWIRQFP GNKLEWMGYMSYSGSTRYNPSLRSRISITRDTSKNQFFLQLK SVTTEDTATYFCARGWPLAYWGQGTQVSVSEAKTTPPSVYP LAPGSAAQTNSMVTLGCLVKGYFPEPVTVTWNSGSLSSGVH TFPAVLQSDLYTLSSSVTVPSSPRPSETVTCNVAHPASSTKV DKKIVPRDC |
| SEQ ID NO: 02 VL of anti DNP scFv (Ab-1; 1BAF) | QIVLTQSPAIMSASPGEKVTMTCSASSSVYYMYWYQQKPGSS PRLLIYDTSNLASGVTVRFSGSGSGTSYSLTISRMEAEDAATY YCQQWSSYPPITFGVGTKLELKRADAAPTVSIFPPSSEQLTSG GASVVCFLNNFYPKDINVKWKIDGSERQNGVLNSWTDQDSK DSTYSMSSTLTLTKDEYERHNSYTCEATHKTSTSPIVKSFNRN EC |

TABLE 2-continued

| SEQ ID NO | Sequence |
|---|---|
| SEQ ID NO: 03<br>VH of anti<br>DNP scFv<br>(Ab-2, XC) | QQLEQSGGGAEGGLVKPGGSLELCCKASGFSLSSSYCICWVR<br>QAPGKGLEWIGCIYAGSSGSTYYASWVNGRFTLSRDIDQSTG<br>CLQLNSLTAADTAMYYCARAPYSSGWVLYFNLWGPGTLVIV |
| SEQ ID NO: 04<br>VL of anti<br>DNP scFv<br>(Ab-2; XC) | AQVLTQTPSPVSAAVGGTVTISCQSSESVYGNSRLAWYQQKP<br>GQSPKLLIYYASTLASGVPSRFKGSGSGTQFTLTISDLECDD<br>AASYYCQGGYYSGNLDALAF |
| SEQ ID NO: 05<br>VH of anti<br>DNP scFv<br>(Ab-3) | QQLEQSGGGAEGGLVKPGGSLELCCKASGISISSSYCICWVR<br>QAPGKGLEWIGCIYAGSSGSTYYASWVNGRFTLSRDIDQSTG<br>CLQLNSLTAADTAMYYCARAPYSSGWVLYFNLWGPGTLVIV |
| SEQ ID NO: 06<br>VL of anti<br>DNP ScFv<br>(Ab-3) | PGATFAQVLTQTPSPVSAAVGGTVTISCQSSESVYGNSRLAW<br>YQQKPGQSPKLLIYYASTLASGVPSRFKGSGSGTQFTLTISD<br>LECDDAASYYCQGGYYSGNLDALAFGGGTEVVVRG |
| SEQ ID NO: 7<br>VL-linker-VH<br>of anti<br>DNP scFv (Ab-3) | PGATFAQVLTQTPSPVSAAVGGIVFISCQSSESVYGNSRLAW<br>YQQKPGQSPKLLIYYASTLASGVPSRFKGSGSGTQFTLTISD<br>LECDDAASYYCOGGYYSGNLDALAFGGGTEVVVRGGGGGSG<br>GGGSGGGGSQCQQLEQSGGGAEGGLVKPGGSLELCCKASGF<br>SLSSSYCICWVRQAPGKGLEWIGCIYAGSSGSTYYASWVNG<br>RFTLSRDIDQSTGCLQLNSLTAADTAMYYCARAPYSSGWVL<br>YFNLWGPGTLVIVSS |
| SEQ ID NO: 08<br>VH-linker-VL<br>of anti<br>DNP scFv (Ab-3) | QCQQLEQSGGGAEGGLVKPGGSLELCCKASGISISSSYCICW<br>VRQAPGKGLEWIGCIYAGSSGSTYYASWVNGRITLSRDIDQS<br>TGCLQLNSLTAADTAMYYCARAPYSSGWVLYFNLWGPGTL<br>VIVSSGGGGSGGGGSGGGGSPGATFAOVLTOTPSPVSAAVGG<br>TVTISCQSSESVYGNSRLAWYQQKPGQSPKLLIYYASTLASG<br>VPSRFKGSGSGTQFTLTISDLECDDAASYYCQGGYYSGNLDA<br>LAFGGGTEVVVRG |
| SEQ ID NO: 09<br>VH-linker-VL<br>of anti<br>DNP scFv (1BAF) | DVQLQESGPGLVKPSQSQSLTCTVTGYSITSDYAWNWIRQFP<br>GNKLEWMGYMSYSGSTRYNPSLRSRISITRDTSKNQFFLQLK<br>SVTTEDTATYFCARGWPLAYWGQGTQVSVSEAKTTPPSVYPL<br>APGSAAQTNSMVTLGCLVKGYFPEPVTVTWNSGSLSSGVHTF<br>PAVLQSDLYTLSSSVTVPSSPRPSETVTCNVAHPASSTKVDK<br>KIVPRDCGGGGSGGGGSGGGGSQIVLTOSPAIMSASPGEKVT<br>MTCSASSSVYYMYWYQQKPGSSPRLLIYDTSNLASGVPVRFS<br>GSGSGTSYSLTISRMEAEDAATYYCQQWSSYPPITFGVGTKL<br>ELKRADAAPTVSIFPPSSEQLTSGGASVVCFLNNFYPKDINV<br>KWKIDGSERQNGVLNSWTDQDSKDSTYSMSSTLTLTKDEYER<br>HNSYTCEATHKTSTSPIVKSFNRNEC |
| SEQ ID NO: 10<br>VL-linker-VH<br>of anti<br>DNP scFv (1BAF) | QIVLTQSPAIMSASPGEKVTMTCSASSSVYYMYWYQQKPGSS<br>PRLLIYDTSNLASGVPVRFSGSGSGTSYSLTISRMEAEDAAT<br>YYCQQWSSYPPITFGVGTKLELKRADAAPTVSIFPPSSEQLT<br>SGGASVVCFLNNFYPKDINVKWKIDGSERQNGVLNSWTDQDS<br>KDSTYSMSSTLTLTKDEYERHNSYTCEATHKTSTSPIVKSFN<br>RNECGGGGSGGGGSGGGGSDVQLQESGPGLVKPSQSQSLTCT<br>VTGYSITSDYAWNWIRQFPGNKLEWMGYMSYSGSTRYNPSLR<br>SRISITRDTSKNQFFLQLKSVTTEDTATYFCARGWPLAYWGQ<br>GTQVSVSEAKTTPPSVYPLAPGSAAQTNSMVTLGCLVKGYFP<br>EPVTVTWNSGSLSSGVHTFPAVLQSDLYTLSSSVTVPSSPRP<br>SETVTCNVAHPASSTKVDKKIVPRDC |
| SEQ ID NO: 11<br>VH-linker-VL<br>of anti<br>DNP scFv (XC) | QQLEQSGGGAEGGLVKPGGSLELCCKASGFSLSSSYCICWVR<br>QAPGKGLEWIGCIYAGSSGSTYYASWVNGRFTLSRDIDQSTG<br>CLQLNSLTAADIAMYYCARAPYSSGWVLYFNLWGPGTLVIVS<br>SGGGGSGGGGSGGGGSAQVLTQTPSPVSAAVGGTVTISCQSS<br>ESVYGNSRLAWYQQKPGQSPKLLIYYASTLASGVPSRFKGSG<br>SGTQFTLTISDLECDDAASYYCQGGYYSGNLDALAF |
| SEQ ID NO: 12<br>VL-linker-VH<br>of anti<br>DNP scFv (XC) | AQVLTQTPSPVSAAVGGTVTISCQSSESVYGNSRLAWYQQKP<br>GQSPKLLIYYASTLASGYTSRFKGSGSGTQFTLTISDLECDD<br>AASYYCOGGYYSGNLDALAFGGGTEVVVRGGGGGSGGGGSG<br>GGGSQQLEQSGGGAEGGLWPGGSLELCCKASGFSLSSSYCI<br>CWVRQAPGKGLEWIGCIYAGSSGSTYYASWVNGRFTLSRDI<br>DQSTGCLQLNSLTAADTAMYYCARAPYSSGWVLYFNLWGP<br>GTLVIV |

TABLE 2-continued

| SEQ ID NO | Sequence |
|---|---|
| SEQ ID NO: 13<br>VH-linker-VL<br>of anti<br>DNP scFv (1BAF) | gacgtacaactgcaagaatcaggtcegggactggtcaaacctagccagtctcagtecttgacgtg<br>caccgtgacgggctatagtataacgagtgattacgcttggaattggattcggcagtttccaggcaa<br>taagcttgagtggatgggctatatgtcttactccggctcaactaggtataatccgagccttcggtctc<br>ggatttctatcacaagagatacgagtaagaatcagtttttcttcaactcaaaagegtcaccacgga<br>ggataccgccacatatttctgtgctaggggatggcctcttgcttattgggggcaagggacacaagt<br>gtctgtttccgaagccaaaacaacgccccttcagtctatccgctggcaccgggaagcgcggca<br>caaaccaatagtatggtaacgcteggatgtctegtcaaggggtattttecegagectgtgacagtg<br>acatggaattctgggagtcttagcagcggagtacatacttttccggcagtacttcaatccgatttgta<br>cacgctctectctagtgttacagttccaagctctccacgacctagtgagaccgttacatgtaacgtc<br>gcgcatccggcctcttccactaaagtggataaaaagattgtgcccagggactgcggcggaggg<br>ggctctggcggcggaggatctgggggagggggcagccaaattgtgttgacccagtccccggc<br>cataatgtcegettetcetggcgagaaggttactatgacttgetcagectectccagtgtgtattata<br>tgtactggtatcaacaaaagccgggctcttcccccggctccttatatacgacacgagtaatctggc<br>aagtggcgtgcctgttagattttctgggtccggctctggaacttcatactccctgacaattagccga<br>atggaagccgaggacgcggcgacatactactgccagcaatggtcatcctatccgcctatcactttt<br>ggagtagggaccaaattggagttgaagcgggctgatgcggctcccacagttagtattttccctcc<br>gtccagtgaacaacttacctccgggggagcctccgttgtttgctttctgaacaacttttacccgaaa<br>gatataaatgtcaagtggaagatcgacggctcagagcgccaaaacggggtactcaactcatgga<br>cagatcaggatagtaaagattcaacttacagtatgtctagtaccctgacactgacgaaagatgaat<br>acgaaagacataatagttatacctgtgaagctacacataagacttcaacctctcctattgtaaaatca<br>ttcaaccgaaacgaatgt |
| SEQ ID NO: 14<br>VL-linker-VH<br>of anti<br>DNP scFv (1BAF) | caaattgtgttgacccagtccccggccataatgtccgcttctcctggcgagaaggttactatgactt<br>gctcagcctcctccagtgtgtattatatgtactggtatcaacaaaagccgggctcttcccccggct<br>cotta tatacgacacgagtaatctggcaagtggcgtgcctgttagattttctgggtccggctctgg<br>aacttcatactccctgacaattagccgaatggaagccgaggacgcggcgacatactactgccagc<br>aatggtcatcctatccgcctatcacttttggagtagggaccaaattggagttgaagcgggctgatg<br>cggctcccacagttagtattttccctccgtccagtgaacaacttacctccgggggagcctccgttgt<br>ttgctttctgaacaacttttacccgaaagatataaatgtcaagtggaagatcgacggctcagagcg<br>ccaaaacggggtactcaactcatggacagatcaggatagtaaagattcaacttacagtatgtctag<br>taccctgacactgacgaaagatgaatacgaaagacataatagttatacctgtgaagctacacataa<br>gacttcaacctctcctattgtaaaatcattcaaccgaaacgaatgtggcggagggggctctggcg<br>gcggaggatctgggggagggggcagcgacgtacaactgcaagaatcaggtccgggactggtc<br>aaacctagccagtctcagtccttgacgtgcaccgtgacgggctatagtataacgagtgattacgct<br>tggaattggattcggcagtttccaggcaataagcttgagtggatgggctatatgtcttactccggct<br>caactaggtataatccgagccttcggtctcggatttctatcacaagagatacgagtaagaatcagtt<br>ttttcttcaactcaaaagcgtcaccacggaggataccgccacatatttctgtgctaggggatggcct<br>cttgcttattgggggcaagggacacaagtgtctgtttccgaagccaaaacaacgccccttcagtc<br>tatccgctggcaccgggaagcgcggcacaaaccaatagtatggtaacgctcggatgtctcgtca<br>aggggtattttcccgagcctgtgacagtgacatggaattctgggagtcttagcagcggagtacata<br>cttttccggcagtacttcaatccgatttgtacacgctctcctctagtgttacagttccaagctctcc<br>acgacctagtgagaccgttacatgtaacgtcgcgcatccggcctcttccactaaagtggataaaaag<br>attgtgeccagggactge |
| SEQ ID NO: 15<br>VH-linker-VL<br>of anti<br>DNP scFv (XC) | cagcagctggagcagtccggaggaggagccgaaggaggcctggtcaagcctgggggatccc<br>tggaactctgctgcaaagcctctggattctccctcagtagtagctactgcatatgttgggtccgcca<br>ggctccagggaaggggctggagtggatcggatgcatttatgctggtagtagtggtagcacttact<br>acgcgagctgggtgaatggccgattcactctctccagagacattgaccagagcacaggttgccta<br>caactgaacagtctgacagccgcggacacggccatgtattactgtgcgagagccccctatagta<br>gtggctgggtcctctactttaacttgtggggcccaggcaccctggtcattgtctcctcaggcggag<br>gggctctggcggcggaggatctgggggagggggcagcgcccaagtgctgacccagactcc<br>atcgcctgtgtctgcagctgtgggaggcacagtcaccatcagttgccagtccagtgagagtgttta<br>tggtaacagccgcttagcctggtatcagcagaaaccagggcagtctcccaagctcctgatctatta<br>tgcatccactctggcatctggggtcccttcgcggttcaaaggcagtggatctgggacacagttcac<br>tctcaccattagcgacctggagtgtgacgatgctgcctcttactactgtcaaggcggttattatagt<br>ggtaatcttgatgcgcttgctttc |
| SEQ ID NO: 16<br>VL-linker-VH<br>of anti<br>DNP scFv (XC) | gcccaagtgctgacccagactccatcgcctgtgtctgcagctgtgggaggcacagtcaccatca<br>gttgccagtccagtgagagtgtttatggtaacagccgcttagcctggtatcagcagaaaccaggg<br>cagtctcccaagctcctgatctattatgcatccactctggcatctggggtcccttcgcggttcaaag<br>gcagtggatctgggacacagttcactctcaccattagcgacctggagtgtgacgatgctgcctctt<br>actactgtcaaggcggttattatagtggtaatcttgatgcgcttgctttcggcggagggaccgaggt<br>ggtggtcagaggtggcggagggggctctggcggcggaggatctgggggagggggcagcca<br>gcagotggagcagtccggaggaggagccgaaggaggcctggtcaagcctgggggatccctg<br>gaactctgctgcaaagcctctggattctccctcagtagtagctactgcatatgttgggtccgccagg<br>ctccagggaaggggctggagtggatcggatgcatttatgctggtagtagtggtagcacttactac<br>gcgagctgggtgaatggccgattcactctctccagagacattgaccagagcacaggttgcctaca<br>actgaacagtctgacagccgcggacacggccatgtattactgtgcgagagccccctatagtagtg<br>gctgggtcctctactttaacttgtggggcccaggcaccctggtcattgtc |
| SEQ ID NO: 17<br>VH-linker-VL<br>of anti<br>DNP scFv (Ab-3) | ccaggtgccacatttgeccaagtgctgacccagactccategectgtgtctgeagctgtgggagg<br>cacagtcaccatcagttgccagtccagtgagagtgtttatggtaacagccgcttagcctggtatca<br>gcagaaaccagggcagtctcccaagctcctgatctattatgcatccactctggcatctggggtccc<br>ttcgcggttcaaaggcagtggatctgggacacagttcactctcaccattagcgacctggagtgtga<br>cgatgctgcctcttactactgtcaaggcggttattatagtggtaatcttgatgcgcttgctttcggc<br>ggagggaccgaggtggtggtcagaggtggcggagggggctctggcggcggaggatctgggggga<br>gggggcagccagtgtcagcagctggagcagtccggaggaggagccgaaggaggcctggtca |

TABLE 2-continued

| SEQ ID NO | Sequence |
|---|---|
| | agcctgggggatccctggaactctgctgcaaagcctctggattctccctcagtagtagctactgca tatgttgggtccgccaggctccagggaaggggctggagtggatcggatgcatttatgctggtagt agtggtagcacttactacgcgagctgggtgaatggccgattcactctctccagagacattgacca gagcacaggttgcctacaactgaacagtctgacagccgcggacacggccatgtattactgtgcg agagccccctatagtagtggctgggtcctctactttaacttgtggggcccaggcaccctggtcatt gtctcctca |
| SEQ ID NO: 18 anti DNP scFv VH-linker-VL of anti DNP scFv (Ab-3) | cagtgtcagcagctggagcagtccggaggaggagccgaaggaggcctggtcaagcctgggg gatccctggaactctgctgcaaagcctctggattctccctcagtagtagctactgcatatgttggg tccgccaggctccagggaaggggctggagtggatcggatgcatttatgctggtagtagtggtagc acttactacgcgagctgggtgaatggccgattcactctctccagagacattgaccagagcacagg ttgcctacaactgaacagtctgacagccgcggacacggccatgtattactgtgcgagagccccct atagtagtggctgggtcctctactttaacttgtggggcccaggcaccctggtcattgtctcctcag gcggagggggctctggcggcggaggatctgggggagggggcagcccaggtgccacatttgcc caagtgctgacccagactccatcgcctgtgtctgcagctgtgggaggcacagtcaccatcagttg ccagtccagtgagagtgtttatggtaacagccgcttagcctggtatcagcagaaaccagggcagt ctcccaagctcctgatctattatgcatccactctggcatctggggtcccttcgcggttcaaaggcag tggatctgggacacagttcactctcaccattagcgacctggagtgtgacgatgctgcctcttactac tgtcaaggcggttattatagtggtaatcttgatgcgcttgctttcggcggagggaccgaggtggtg gtcagaggt |
| SEQ ID NO: 19 linker | GGGGSGGGGSGGGGS |
| SEQ ID NO: 20 Long spacer: IgG4hinge-CH2(L235D)-CH3 | ESKYGPPCPPCPAPEFDGGPSVFLFPPKPKDTLMISRTPEVTC VVVDVSQEDPEVQFNWYVDGVEVHNAKTKPREEQFNSTYR VVSVLTVLHQDWLNGKEYKCKVSNKGLPSSIEKTISKAKGQ PREPQVYTLPPSQEEMTKNQVSLTCLVKGFYPSDIAVEWESN GQPENNYKTTPPVLDSDGSFFLYSRLTVDKSRWQEGNVFSC SVMHEALHNHYTQKSLSLSLGK |
| SEQ ID NO: 21 Medium spacer: IgG4hinge-CH3 | ESKYGPPCPPCPGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGK |
| SEQ ID NO: 22 Short spacer: hinge IgG4 | ESKYGPPCPPCP |
| SEQ ID NO: 23 CD28tm | MFWVLVVVGGVLACYSLLVTVAFIIFWV |
| SEQ ID NO: 24 4-1BB | KRGRKKLLYIFKQPFMRPVQTTQEEDGCSCRFPEEEEGGCEL |
| SEQ ID NO: 25 CD3 zeta | RVKFSRSADAPAYQQGQNQLYNELNLGRREEYDVLDKRRG RDPEMGGKPRRKNPQEGLYNELQKDKMAEAYSEIGMKGER RRGKGHDGLYQGLSTATKDTYDALHMQALPPR |
| SEQ ID NO: 26 T2A | GGGEGRGSLLTCGDVEENPGP |
| SEQ ID NO: 27 GM-CSF receptor ss to EGFRt | MLLLVTSLLLCELPHPAFLLIPRKVCNGIGIGEFKDSLSINATN IKHFKNCTSISGDLHILPVAFRGDSFTHTPPLDPQELDILKTVK EITGFLLIQAWPENRTDLHAFENLEIIRGRTKQHGQFSLAVVS LNITSLGLRSLKEISDGDVIISGNKNLCYANTINWKKLFGTSG QKTKIISNRGENSCKATGQVCHALCSPEGCWGPEPRDCVSC RNVSRGRECVDKCNLLEGEPREFVENSECIQCHPECLPQAM NITCTGRGPDNCIQCAHYIDGPHCVKTCPAGVMGENNTLVW KYADAGHVCHLCHPNCTYGCTGPGLEGCPTNGPKIPSIATG MVGALLLLLVVALGIGLFM |
| SEQ ID NO: 28 DHFRdm | MVGSLNCIVAVSQNMGIGKNGDFPWPPLRNESRYFQRMTTT SSVEGKQNLVIMGKKTWFSIPEKNRPLKGRINLVLSRELKEP PQGAHFLSRSLDDALKLTEQPELANKVDMVWIVGGSSVYK EAMNHPGHLKLFVTRIMQDFESDTFFPEIDLEKYKLLPEYPG VLSDVQEEKGIKYKFEVYEKND |
| SEQ ID NO: 29 GM-CSF signal Sequence | MLLLVTSLLLCELPHPAFLLIP |

In some embodiments, the one or more nucleic acids described herein comprise a spacer, wherein the spacer is a short spacer having 12 consecutive amino acid residues or less, and not less than 1 amino acid residue. In some embodiments, the one or more nucleic acids described herein encode a spacer, which is a medium spacer having 119 consecutive amino acid residues or less but not less than one amino acid. In some embodiments, the one or more nucleic acids described herein encode a spacer, which is a long spacer having greater than 119 consecutive amino acid residues. In some embodiments, the long spacer has 229 consecutive amino acid residues or less and not less than 1 amino acid. In some embodiments, nucleic acids described herein encode a spacer selected from the group consisting of a short spacer comprising an IgG4 hinge domain, a medium spacer comprising an IgG4 hinge-CH3 domain, and a long spacer comprising an IgG4 hinge —CH2-CH3 domain. In some embodiments, the nucleic acids described herein encode a spacer, which is a long spacer.

In some embodiments, the transmembrane domain comprises a CD28 transmembrane domain.

In some embodiments, the nucleic acids described herein encode an intracellular signaling domain comprises a portion of CD3 zeta and/or a portion of 4-1BB.

Some embodiments also include a polynucleotide encoding a selectable gene, a cell surface selectable marker, or a cleavable linker. In some embodiments, the selectable gene comprises a dihydrofolate reductase double mutant (DHFRdm). In some embodiments, the cell surface selectable marker is selected from the group consisting of a truncated EGFR (EGFRt), a truncated Her2 (Her2tG), and a truncated CD19 (CD19t). In some embodiments, the cleavable linker comprises a ribosome skip sequence is selected from the group consisting of P2A, T2A, E2A and F2A.

Some embodiments of the methods and compositions provided herein include vectors comprising any one of the nucleic acids provided herein. In some embodiments, the vector comprises a lentiviral vector.

Certain CARs

Some embodiments of the methods and compositions provided herein include CARs, which specifically bind to a DNP moiety. In some embodiments, the DNP moiety is associated with a PLE molecule. In some embodiments, the DNP moiety is associated with an antibody or a folate. In some embodiments, the CAR is encoded by the any one or more of the nucleic acids provided herein.

In some embodiments, the ligand binding domain of the CARs described and used herein comprises an scFv domain comprising a VH sequence, and VL sequence derived from an antibody. In some embodiments, the VH and VL sequences are joined together via a linker. Examples of VH sequences, VL sequences and linkers used with one or more of the CARs described herein are listed in TABLE 2. In some embodiments, the ligand binding domain of a CAR set forth herein comprises an amino acid sequence having at least 70%, 80%, 90%, 95%, 96%, 97%, 98%, 99% or 100% identity to the amino acid sequence set forth in any one of SEQ ID NOs:01-12. In some embodiments, the ligand binding domain of a CAR described herein comprises the amino acid sequence set forth in any one of SEQ ID NOs:01-12. In some embodiments, the ligand binding domain of a CAR set forth herein comprises an amino acid sequence having at least 70%, 80%, 90%, 95%, 96%, 97%, 98%, 99% or 100% identity to the amino acid sequence set forth in SEQ ID NOs:01 or 02. In some embodiments, the ligand binding domain of a CAR set forth herein comprises an amino acid sequence having at least 70%, 80%, 90%, 95%, 96%, 97%, 98%, 99% or 100% identity to the amino acid sequence set forth in SEQ ID NOs:01, 02, 09, or 10.

In some embodiments, the CARs described herein comprise a spacer, which is a short spacer having 12 consecutive amino acid residues or less, and not less than 1 amino acid residue. In some embodiments, the CARs described herein comprise a spacer, which is a medium spacer having 119 consecutive amino acid residues or less and not less than 1. In some embodiments, the CARs described herein comprise a spacer, which is a long spacer having greater than 119 consecutive amino acid residues. In some embodiments, the CARs described herein comprise a long spacer having 229 consecutive amino acid residues or less but not less than 1. In some embodiments, the CARs described herein comprise a spacer selected from the group consisting of a short spacer comprising an IgG4 hinge domain, a medium spacer comprising an IgG4 hinge-CH3 domain, and a long spacer comprising an IgG4 hinge —CH2-CH3 domain. In some embodiments, the CARs described herein comprise spacer, which is a long spacer.

In some embodiments, the CARs described herein comprise a transmembrane domain, which comprises a CD28 transmembrane domain. In some embodiments, the CARs described herein comprise an intracellular signaling domain, which comprises a portion of CD3 zeta and/or a portion of 4-1BB.

In some embodiments, a DNP moiety is attached to an antibody or an antigen binding fragment thereof displayed on a CAR, which may be presented by a cell, such as a T cell.

In some embodiments, the DNP moiety is attached to a lipid. In some embodiments, the lipid comprises a polar head group and a hydrophobic group. In some embodiments, the polar head comprises a group selected from choline, phosphatidylcholine, phosphocholine, sphingomyelin, aphosphoethanolamine, a sugar residue, phosphatidyl serine, phosphatidyl inositol, a piperidine, or a trimethylarsenoethyl-phosphate. In some embodiments, the hydrophobic group comprises an aliphatic chain or a terpenoid moiety. In some embodiments, the hydrophobic group comprises an ether linkage, wherein the ether linkage is between the polar head group and the aliphatic chain. In some embodiments, the aliphatic chain comprises a $C_{10-20}$ alkyl chain. In some embodiments, the lipid is a PLE. An embodiment of a DNP moiety attached to a lipid is depicted in FIG. 1.

Certain Cells Comprising CARs

Some embodiments of the methods and compositions provided herein include cells comprising any one of the CARs provided herein and/or comprising any one of the nucleic acids encoding a CAR provided herein.

In some embodiments, the cell is derived from a CD4+ T cell, a CD8+ T cell, a precursor T cell, or a hematopoietic stem cell. In some embodiments, the CD8+ T cell is a CD8+ cytotoxic T lymphocyte cell selected from the group consisting of a naïve CD8+ T cell, a central memory CD8+ T cell, an effector memory CD8+ T cell, and a bulk CD8+ T cell. In some embodiments, the central memory CD8+ T cell is positive for CD45RO and CD62L. In some embodiments, the CD4+ cell is a CD4+ helper T lymphocyte cell selected from the group consisting of a naïve CD4+ T cell, a central memory CD4+ T cell, an effector memory CD4+ T cell, and a bulk CD4+ T cell. In some embodiments, the naïve CD4+ T cell is positive for CD45RA and CD62L, and negative for CD45RO.

In some embodiments, the cell is ex vivo. In some embodiments, the cell is in vivo. In some embodiments, the cell is mammalian. In some embodiments, the cell is human.

Some embodiments of the methods and compositions provided herein include preparing a population of cells comprising one or more of the CARs described herein. In some embodiments, the population of cells comprising a CAR described herein is incorporated into an infusion for administration to a subject in need e.g., a cancer patient. Some embodiments include introducing the nucleic acid of any one or more of the nucleic acids encoding a CAR or component thereof as provided herein. Some embodiments also include culturing the cell under conditions suitable to obtain a population of cells sufficient for an infusion.

Certain Therapies

Some embodiments of the methods and compositions provided herein include methods of treating, inhibiting, or ameliorating a cancer in a subject. Some such methods include administering any one of the anti-DNP CAR T cells provided herein to the subject and optionally selecting said subject to receive such a therapy based on diagnostic or clinical evaluation or both. In some embodiments, the anti-DNP CAR T cell is administered to the subject in combination with a composition comprising a DNP moiety, such as DNP-PLE, or an anti-tumor antigen antibody or antigen binding fragment thereof comprising a DNP moiety.

In some embodiments, the cell is administered prior to administration of the DNP moiety, such as DNP-PLE, or an anti-tumor antigen antibody or antigen binding fragment thereof comprising a DNP moiety. In some embodiments, the cell is administered subsequent to administration of the DNP moiety, such as DNP-PLE, or an anti-tumor antigen antibody or antigen binding fragment thereof comprising a DNP moiety. In some embodiments, the cell is co-administered with the DNP moiety, such as DNP-PLE or an anti-tumor antigen antibody or antigen binding fragment thereof comprising a DNP moiety.

In some embodiments, the composition comprising a DNP moiety, such as DNP-PLE is adapted to or configured to target the cancer. Alternatively, in some embodiments, the DNP moiety is attached to an antibody or antigen binding fragment thereof, which specifically binds to the cancer.

Preferably, the DNP moiety is attached to a lipid. In some embodiments, the lipid comprises a polar head group and a hydrophobic group. In some embodiments, the polar head comprises a group selected from choline, phosphatidylcholine, phosphocholine, sphingomyelin, aphosphoethanolamine, a sugar residue, phosphatidyl serine, phosphatidyl inositol, a piperidine, or a trimethylarseno-ethyl-phosphate. In some embodiments, the hydrophobic group comprises an aliphatic chain or a terpenoid moiety. In some embodiments, the hydrophobic group comprises an ether linkage, wherein the ether linkage is between the polar head group and the aliphatic chain. In some embodiments, the aliphatic chain comprises a $C_{10-20}$ alkyl chain. In some embodiments, the lipid is a PLE.

In some embodiments, the cancer comprises a target cell selected from the group consisting of a breast cancer cell, brain cancer cell, colon cancer cell, renal cancer cell, pancreatic cancer cell, and ovarian cancer cell.

In some embodiments, the anti-DNP CAR T cell is autologous to the subject. In some embodiments, the subject is mammalian. In some embodiments, the subject is human.

Certain Compositions, System and Kits

Some embodiments of the methods and compositions provided herein include compositions comprising: any one of the anti-DNP CARs provided herein, and a DNP moiety attached to a target cell, in which the CAR is specifically bound to the DNP moiety.

In some embodiments, the DNP moiety is attached to the target cell via an antibody or antigen binding fragment thereof that binds to the target cell.

In some embodiments, the DNP moiety is attached to a cell surface of the target cell via a lipid integrated into the cell surface. In some embodiments, the lipid comprises a polar head group and a hydrophobic group. In some embodiments, the polar head comprises a group selected from choline, phosphatidylcholine, phosphocholine, sphingomyelin, aphosphoethanolamine, a sugar residue, phosphatidyl serine, phosphatidyl inositol, a piperidine, or a trimethylarseno-ethyl-phosphate. In some embodiments, the hydrophobic group comprises an aliphatic chain or a terpenoid moiety. In some embodiments, the hydrophobic group comprises an ether linkage, wherein the ether linkage is between the polar head group and the aliphatic chain. In some embodiments, the aliphatic chain comprises a $C_{10-20}$ alkyl chain. In some embodiments, the lipid is a PLE.

In some embodiments, the target cell is a cancer cell. In some embodiments, the cancer cell is selected from the group consisting of a breast cancer cell, brain cancer cell, colon cancer cell, renal cancer cell, pancreatic cancer cell, and ovarian cancer cell. In some embodiments, the target cell is ex vivo. In some embodiments, the target cell is in vivo. In some embodiments, the target cell is mammalian. In some embodiments, the target cell is human.

Some embodiments of the methods and compositions provided herein include systems and/or kits comprising any one of the nucleic acids encoding an anti-DNP CAR and a composition comprising a DNP moiety. In some embodiments, the DNP moiety is attached to an antibody or antigen binding fragment thereof. In some embodiments, the DNP moiety is attached to a lipid.

EXAMPLES

Example 1—Anti-DNP Antibodies Binding to DNP-PLE-Labelled Cells

Figure 2A:
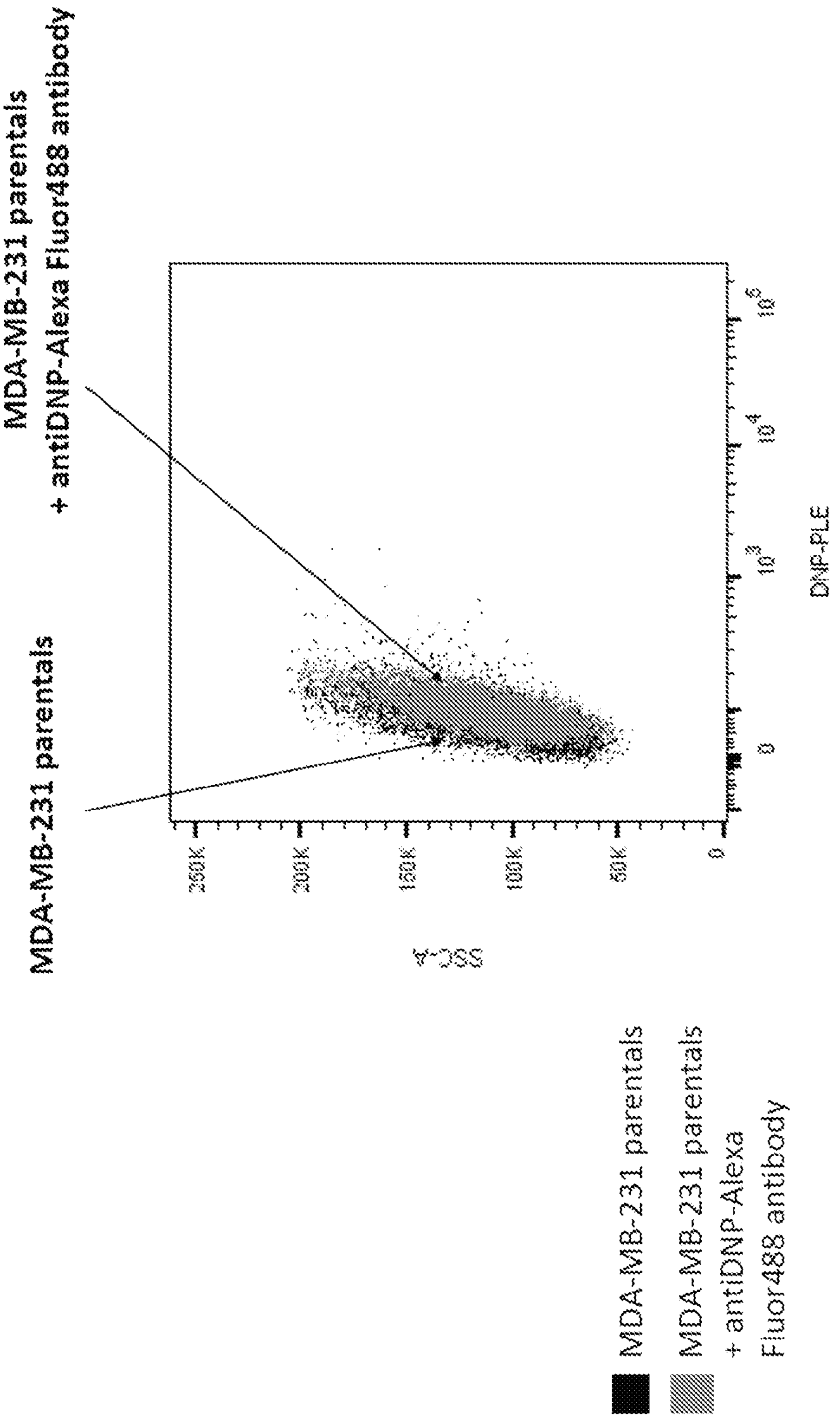
FIG. 2A depicts flow cytometry data for control MDA-MB-231 cells and control MDA-MB-231 cells incubated with an anti-DNP-Alexa Fluor 488 antibody.
Figure 2B:
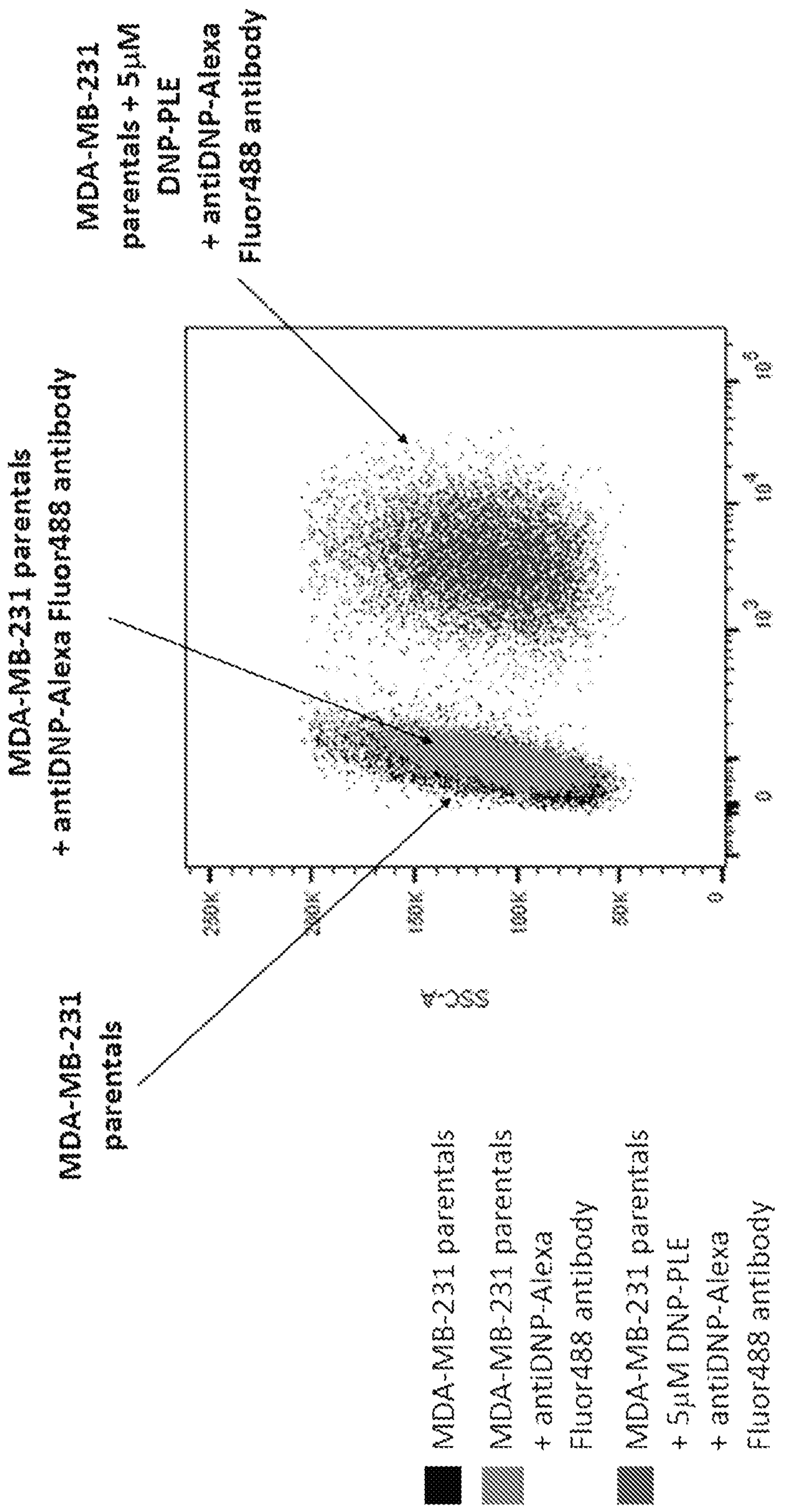
FIG. 2B depicts flow cytometry data for control MDA-MB-231 cells, control MDA-MB-231 cells incubated with an anti-DNP-Alexa Fluor 488 antibody, and MDA-MB-231 cells labelled with 5 μM DNP-PLE and stained with the anti-DNP-Alexa Fluor 488 antibody.
Figure 2C:
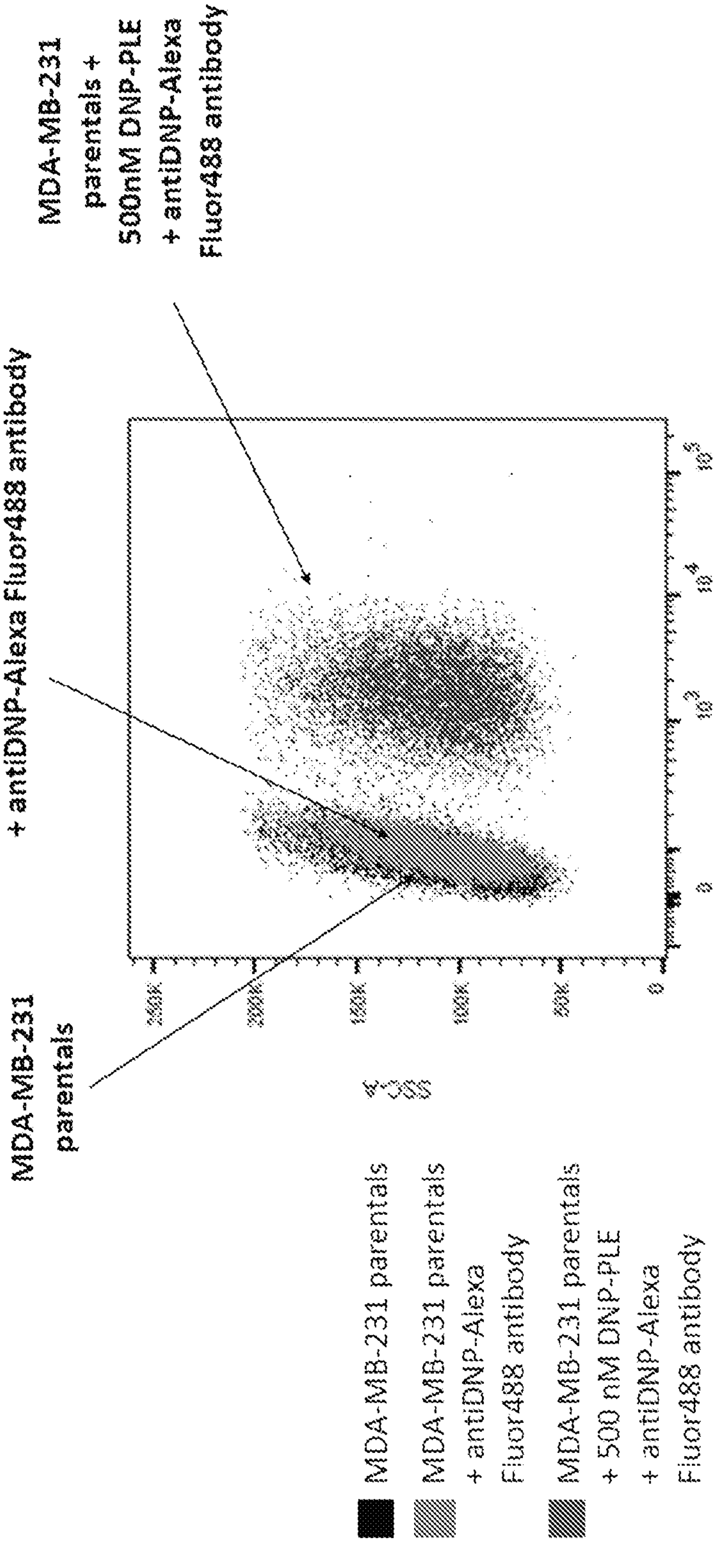
FIG. 2C depicts flow cytometry data for control MDA-MB-231 cells, control MDA-MB-231 cells incubated with an anti-DNP-Alexa Fluor 488 antibody, and MDA-MB-231 cells labelled with 500 nM DNP-PLE and stained with the anti-DNP-Alexa Fluor 488 antibody.
Figure 2D:
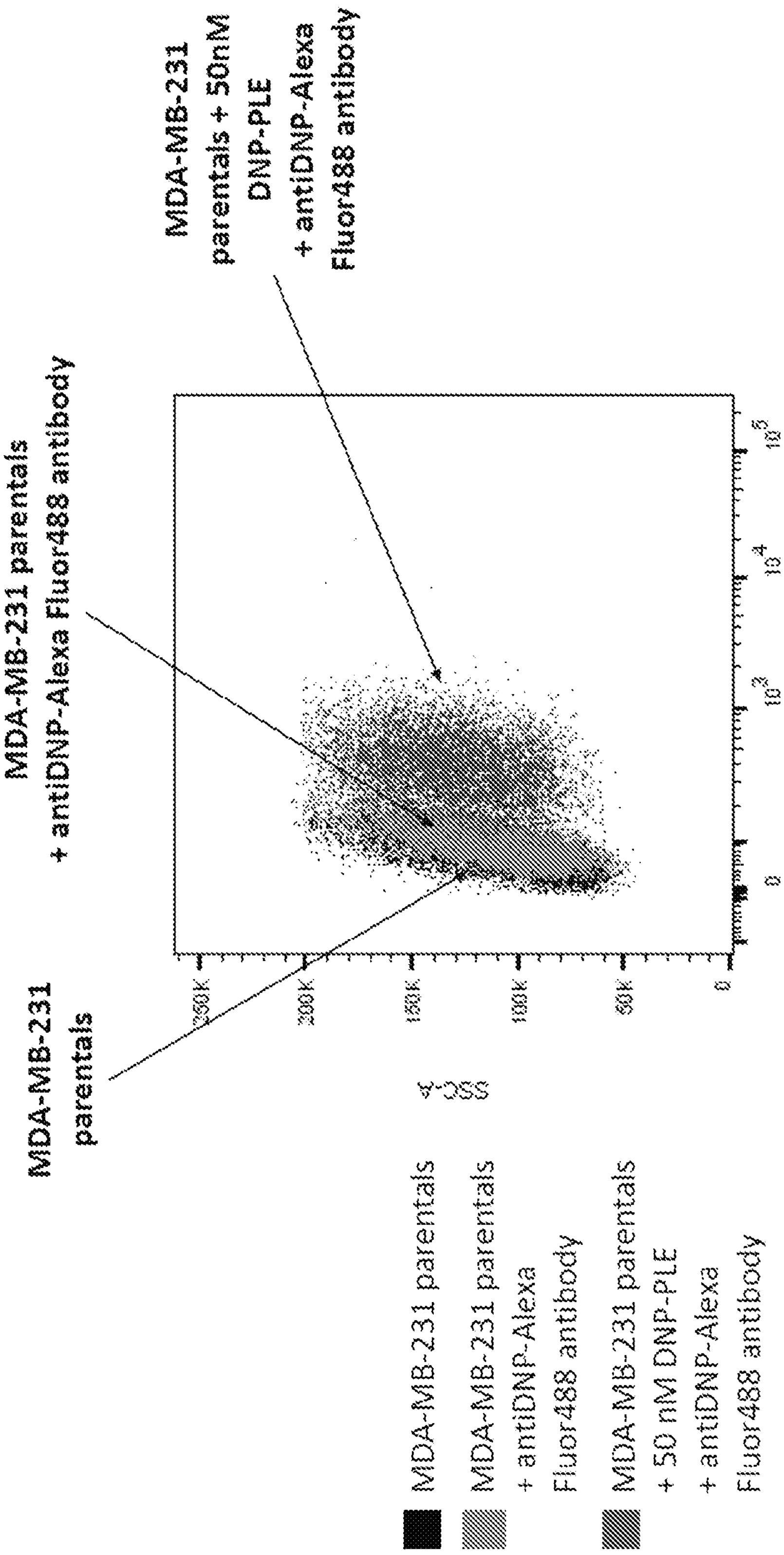
FIG. 2D depicts flow cytometry data for control MDA-MB-231 cells, control MDA-MB-231 cells incubated with an anti-DNP-Alexa Fluor 488 antibody, and MDA-MB-231 cells labelled with 50 nM DNP-PLE and stained with the anti-DNP-Alexa Fluor 488 antibody.
Figure 2E:
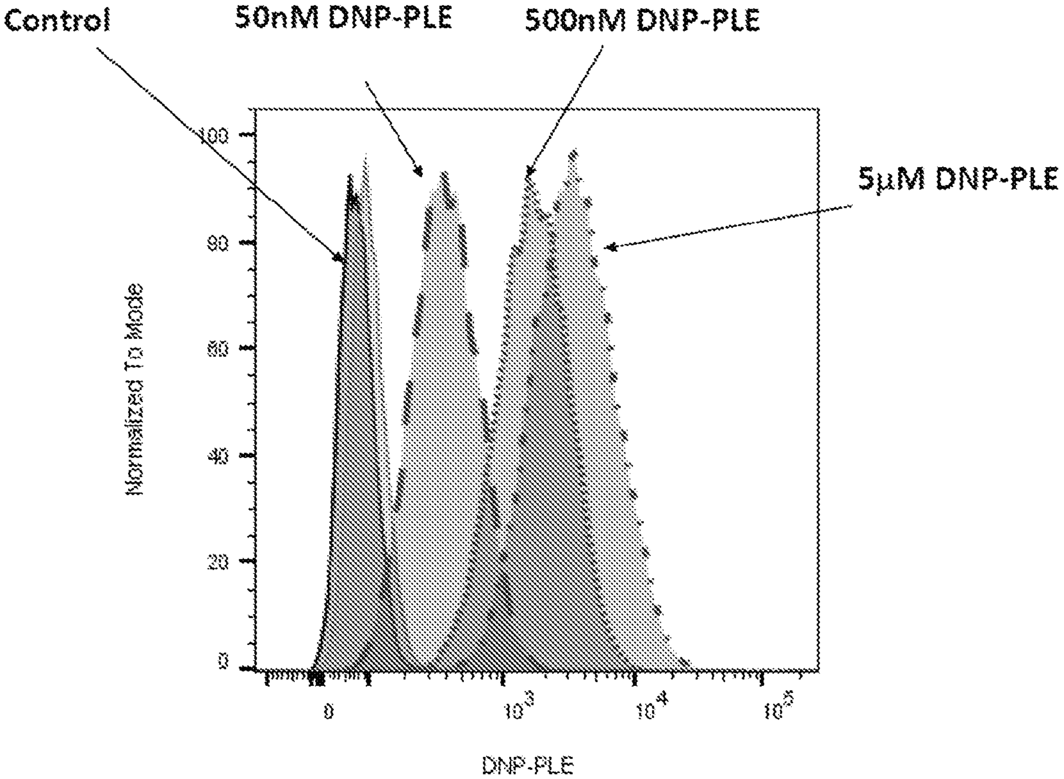
FIG. 2E depicts a histogram plot for the flow cytometry data shown in FIG. 2A-FIG. 2D.

Adenocarcinoma cells, MDA-MB-231, were incubated overnight in the presence of complete media with either 50 nM, 500 nM or 5 μM DNP-PLE. Integration of DNP-PLE into cell membranes was analyzed by contacting the cells with an anti-DNP Alexa Fluor 488 antibody and subsequent flow cytometry. In control cells, no shift was seen between untreated MDA-MB-231 cells and MDA-MB-231 cells stained with the anti-DNP-Alexa Fluor 488 antibody (FIG. 2A). For cells treated with 5 μM DNP-PLE, there was a clear shift from the untreated control cells and treated cells (FIG. 2B); a smaller shift was observed between the untreated control cells and cells treated with 50 nM DNP-PLE (FIG. 2D); and an intermediate shift was observed between the untreated control cells and cells treated with 500 nM DNP-PLE (FIG. 2C). A histogram for the data in FIG. 2A-FIG. 2D is shown in FIG. 2E.

Figure 3A:
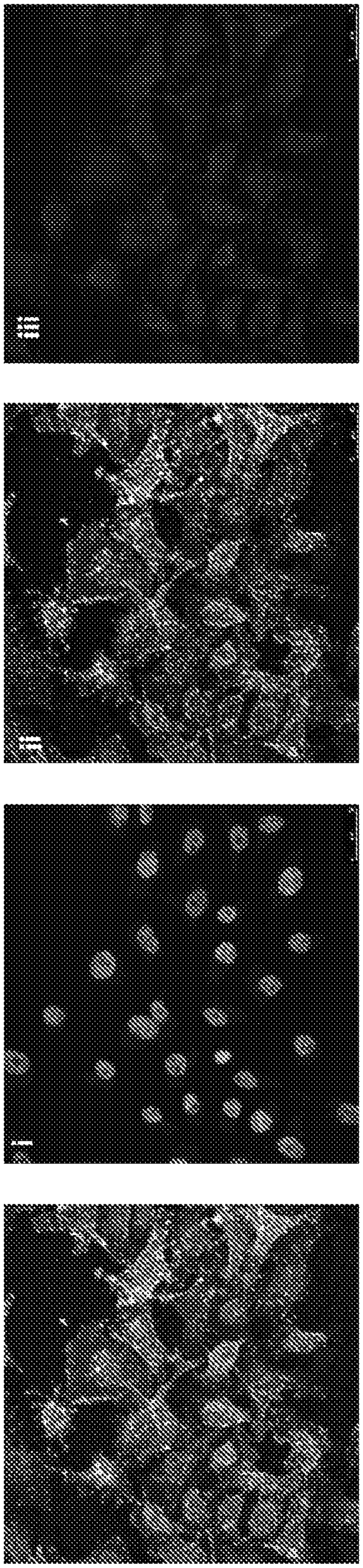
FIG. 3A depicts confocal images of control MDA-MB-231 cells incubated with anti-DNP-Alexa Fluor 488 antibody.
Figure 3B:
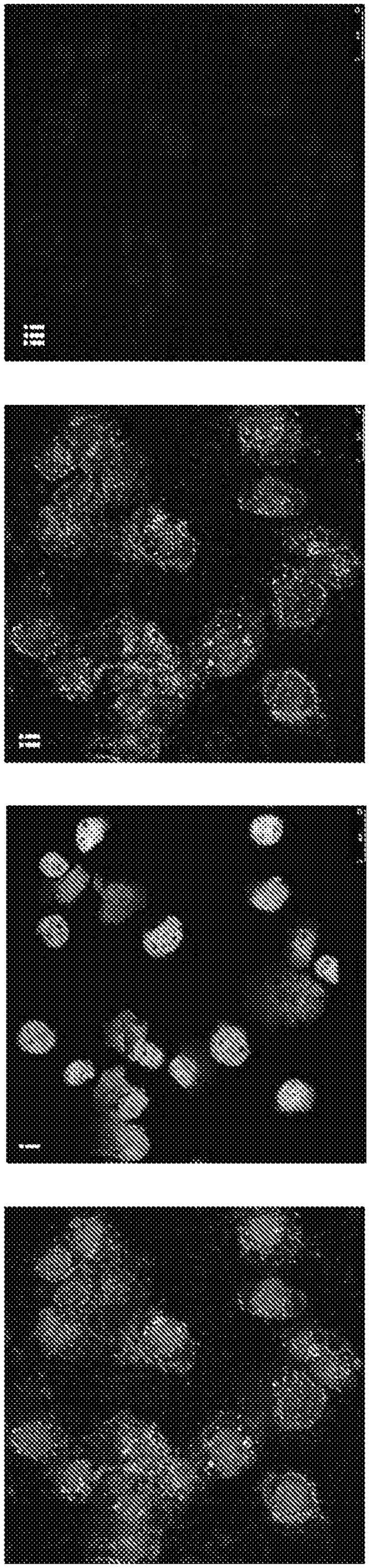
FIG. 3B depicts confocal images of MDA-MB-231 cells incubated with 5 μM DNP-PLE.
Figure 3C:
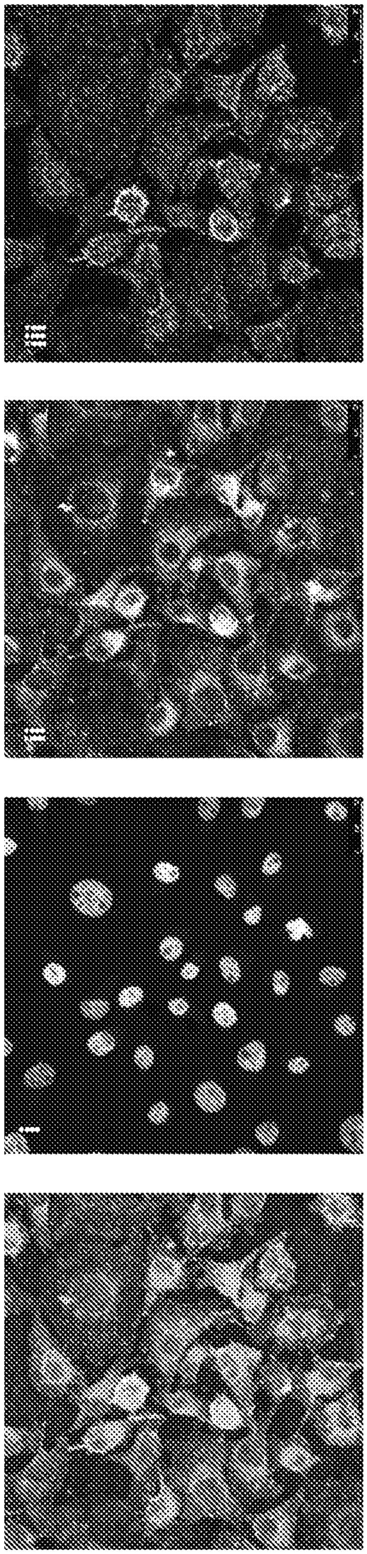
FIG. 3C depicts confocal images of MDA-MB-231 cells incubated with 5 μM DNP-PLE and stained with anti-DNP-Alexa Fluor 488 antibody.
Figure 3D:
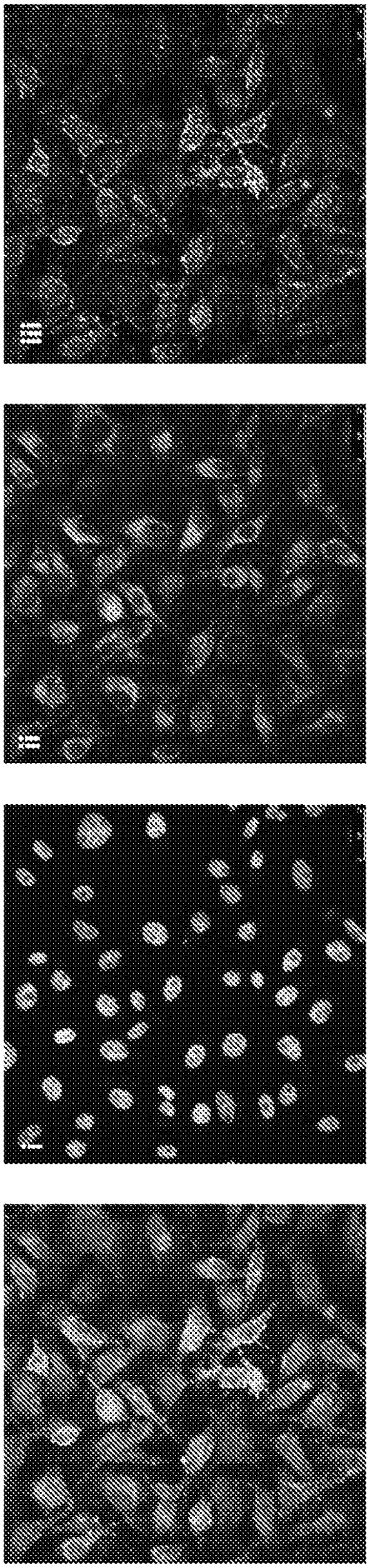
FIG. 3D depicts confocal images of MDA-MB-231 cells incubated with 1 μM DNP-PLE and stained with anti-DNP-Alexa Fluor 488 antibody.

In a further study, MDA-MB-231 cells were incubated overnight with either 1 μM or 5 μM DNP-PLE, washed and imaged by confocal microscopy to confirm the location of DNP-PLE integration in the cells. Nuclei were stained with DAPI (i); cell surfaces were stained with wheat germ agglutinin (WGA) (ii); and DNP was stained with anti-DNP Alexa Fluor 488 antibody (iii). FIG. 3A depicts confocal images of control MDA-MB-231 cells incubated with anti-DNP-Alexa Fluor 488 antibody. FIG. 3B depicts confocal images of MDA-MB-231 cells incubated with 5 μM DNP-PLE. FIG. 3C depicts confocal images of MDA-MB-231 cells incubated with 5 μM DNP-PLE and stained with anti-DNP-Alexa Fluor 488 antibody. FIG. 3D depicts confocal images of MDA-MB-231 cells incubated with 1 μM DNP-PLE and stained with anti-DNP-Alexa Fluor 488 antibody. Anti-DNP staining was localized to the cell surfaces (iii), confirming that DNP-PLE integrated at these sites (FIG. 3C, FIG. 3D). This study also confirmed that the DNP moiety was accessible for antibody binding.

Example 2—Generation of Anti-DNP CARs

Figure 4:
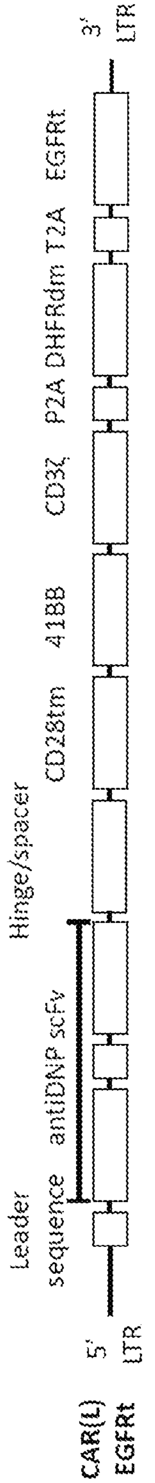
FIG. 4 depicts a schematic of a second generation long CAR cassette for an anti-DNP CAR.

FIG. 4 shows the components of an example polynucleotide encoding an anti-DNP CAR which includes a leader sequence, a ligand binding domain comprising an anti-DNP scFv, a spacer, a CD28 transmembrane domain, intracellular co-stimulatory domains including a 41BB domain and a CD3-zeta domain, a P2A sequence, a selectable marker including a DHFRdm, a T2A sequence, and a cell surface selectable marker including an EGFRt.

A series of polynucleotides encoding different anti-DNP CARs are prepared. Some polynucleotides encode CARs having different spacers, such as a long spacer, a medium spacer, or a short spacer. Some polynucleotides encode CARs having different anti-DNP ligand binding domains, such as different scFv derived from different anti-DNP antibodies (See e.g., Brunger, A. T., et al., (1991) Journal of Molecular Biology, 5:239-56 which is incorporated by reference in its entirety). Some ligand binding domains include a VH sequence, and a VL sequence. Some ligand binding domains include a VH sequence, and a VL sequence having a linker there between. TABLE 1 lists a series of CARs that are prepared, and TABLE 2 lists sequences for components of the CARs. For example, a CAR comprising a ligand binding domain for VH-linker-VL of Ab-1 (1BAF) with a long spacer includes a polynucleotide encoding the following amino acid sequences in a NH—COOH orientation: [SEQ ID NO:29, GM-CSF signal Sequence] [SEQ ID NO:01, VH of anti DNP scFv (Ab-1; 1BAF)] [SEQ ID NO:19, linker] [SEQ ID NO:02, VL of anti DNP scFv (Ab-1; 1BAF)] [SEQ ID NO:20, Long spacer: IgG4hinge-CH2(L235D)-CH3] [SEQ ID NO:23, CD28tm] [SEQ ID NO:24, 4-1BB] [SEQ ID NO:25, CD3 zeta] [P2A nucleic acid] [SEQ ID NO:28, DHFRdm] [SEQ ID NO:28, GM-CSF receptor ss to EGFRt].

Example 3—Preparation of Anti-DNP CAR T Cells

A polynucleotide encoding an anti-DNP CAR having a long spacer was transduced into H9 cells (CD4+ and CD3+ cutaneous T lymphocytes). Transduced cells were selected using methotrexate. The efficiency of transduction was determined using flow cytometry to quantify the presence of a EGFRt cell surface marker on transduced cells. Flow plots demonstrated a 92% positive anti-DNP CAR H9 population.

Example 4—Anti-DNP CARs Binding to DNP-PLE-Labelled Cells

MDA-MB-231 cells were incubated overnight with 5 μM DNP-PLE, washed, and co-cultured with anti-DNP CAR T cells. Cells were imaged by confocal microscopy to confirm an interaction between the anti-DNP CAR T cells and DNP-labelled cells. Nuclei were stained with DAPI (i); cell surfaces were stained with wheat germ agglutinin (WGA) (ii); and DNP was stained with anti-DNP Alexa Fluor 488 antibody (iii; and iv). H9 CAR T cells were distinguished from MDA-MB-231 using an anti-CD3 antibody (red). Under each color image is a grey scale for each layer making up the full confocal image: nucleus (i), cell surface (ii), DNP-PLE (iii) and (iv) anti-DNP CAR H9 cells.

Figure 5A:
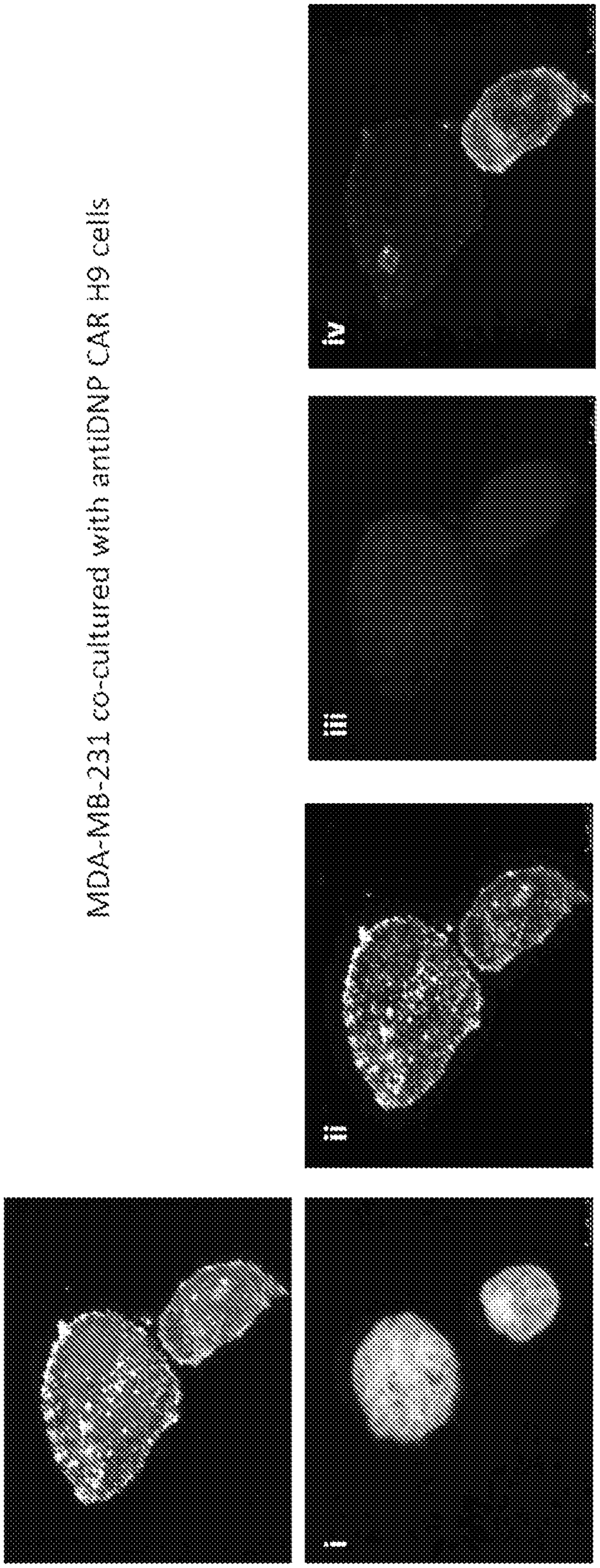
FIG. 5A depicts confocal images of control MDA-MB-231 cells co-cultured with anti-DNP CAR H9 cells.
Figure 5B:
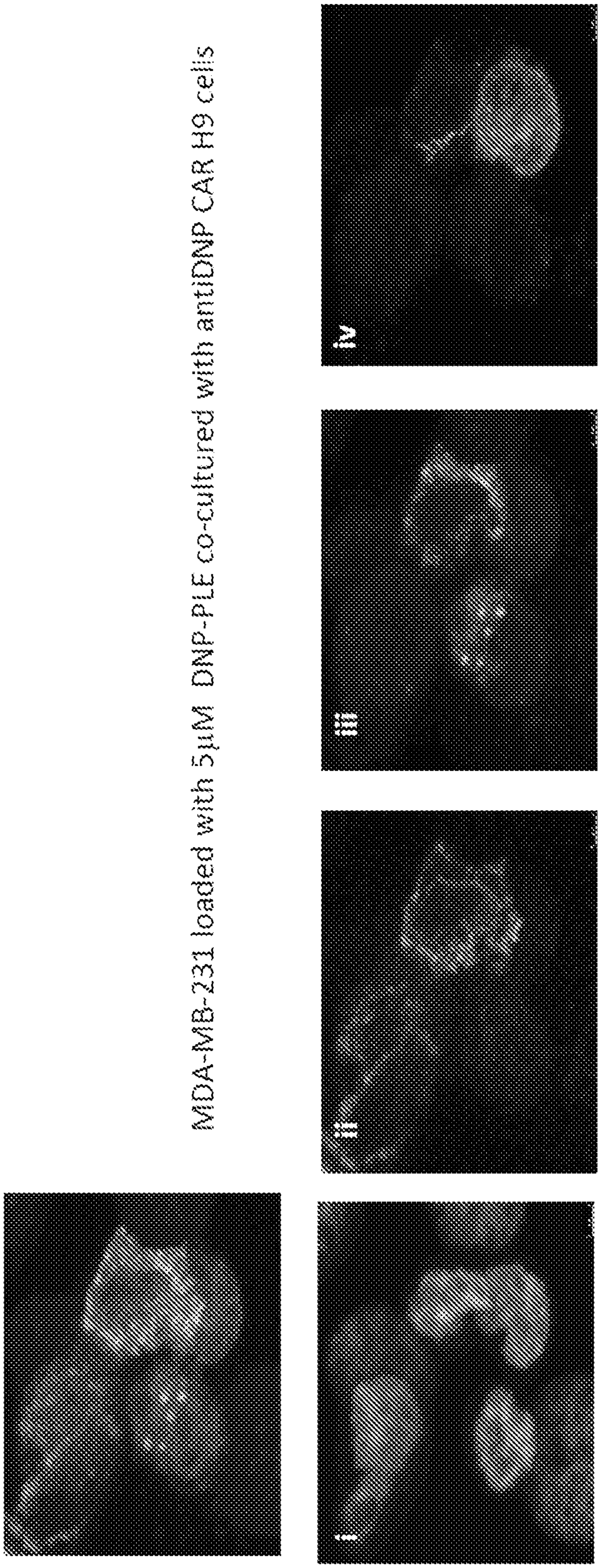
FIG. 5B depicts confocal images MDA-MB-231 cells stained with 5 μM DNP-PLE and co-cultured with anti-DNP CAR H9 cells.

Control unlabeled MDA-MB-231 cells co-cultured with anti-DNP CAR H9 cells are shown in FIG. 5A which shows no binding between MDA-MB-231 and H9 cells. In FIG. 5A, the top left image shows full overlay confocal image of images (i)-(iv). DNP-PLE labelled MDA-MB-231 cells co-cultured with anti-DNP CAR H9 cells are shown in FIG. 5B which shows an interaction between MDA-MB-231 and H9 cells. In FIG. 5B, the top left image shows full overlay confocal image of images (i)-(iv). FIG. 5B showed a synapse formation between the cells, thus confirming recognition of the DNP exposed on the surface of the target cell by the anti-DNP CAR. This study confirmed that an anti-DNP CAR was capable of binding to DNP-labelled cells.

Example 5—In Vitro Activity of Anti-DNP CARs

In vitro activity of anti-DNP CARs is measured using a chromium release assay, and a cytokine production assay. See e.g., Gonzalez, S., Naranjo, A., Serrano, L. M., Chang, W.-C., Wright, C. L., & Jensen, M. C. (2004). Genetic engineering of cytolytic T lymphocytes for adoptive T-cell therapy of neuroblastoma. *The Journal of Gene Medicine*, 6(6), 704-711, hereby expressly incorporated by reference in its entirety.

For the chromium release assay, target cells are incubated with $^{51}Cr$ overnight. For target cells that receive the DNP-PLE, the DNP-PLE is also present in the media overnight with the $^{51}Cr$. The following day the target cells are washed and seeded in a 96 well plate at a concentration 5000 cell per well. CD8+ anti-DNP CAR T cells, and mock T cell effectors (usually in day 8-16 of a rapid expansion protocol) are washed, seeded with the target cells in triplicate at various E:T ratios (30:1, 10:1, 3:1, 1:1), and allowed to co-incubate for 4 hours at 37° C. Also, to evaluate control $^{51}Cr$ release, each target cell line are seeded with media only and for maximum $^{51}Cr$ release each target cell line was seeded and lysed with 2% SDS. Control groups are done in sextuplicate. After co-incubation, the supernatant is harvested, dispensed on LUMA plates, and allowed to dry overnight. The next day samples are run on the Top Count instrument. Percent-specific lysis is calculated by the following formula:

$$\frac{(\text{experimental } ^{51}Cr \text{ release}) - (\text{control } ^{51}Cr \text{ release})}{(\text{maximum } ^{51}Cr \text{ release}) - (\text{control } ^{51}Cr \text{ release})} \times 100$$

In the chromium release assay, the relative levels of lytic activity for various anti-DNP CAR T cells is determined against the DNP-labelled cells. Unlabeled control K562 cells do not induce lysis with the anti-DNP CAR T cells. A positive control includes the use of OKT3 cells which activates T cells through the TCR. Anti-DNP CAR T cells induces specific lysis of DNP-labeled cells.

A cytokine release assay is performed. For target cells that receive the DNP-PLE, the DNP-PLE are incubated overnight in media. The next day all target cells are harvested, washed, and seeded in a 96 well plate at a concentration of $5\times10^4$ cells per well. CD8+ anti-DNP CAR T cells and mock T cell effectors (usually in day 8-16 of a rapid expansion protocol) are washed and seeded ($1\times10^5$ cells/well) with the target cells and are co-incubated for 24 hours at 37° C. After 24 hr the supernatant is harvested and IFN-gamma, TNF-alpha, and IL-2 concentration in the supernatant are measured by using a Bio-Plex® 200 system (Bio-Rad). The levels of cytokines released by the anti-DNP CAR T cells is determined. DNP-labeled cells induce the release of IFN-γ, IL-2 and TNF-α in contact with the anti-DNP CAR T cells.

Example 6—In Vivo Targeting and Integration of DNP-PLE

In vivo targeting and integration of DNP-PLE at tumor sites is tested. After a glioblastoma (U87 cells) tumor is established in a group of mice by intracranial injection, the mice receive an intravenous injection of DNP-PLE. Mice are sacrificed and brains are harvested at various time points post DNP-PLE injection. Specifically, mice having an orthotopic glioma xenograft are dosed intravenously with DNP-PLE, and the brains are evaluated over a period of 14 days. At 48 hr, the brain is prepared for histology. DAPI is also used to stain for the nucleus. An anti-DNP antibody with a fluorescent label is used to stain for availability of DNP-PLE that is integrated into the membrane of cells. The glioma tumor exhibits retention of DNP-PLE in excess compared to a tumor-free contra lateral hemisphere of a subject. In a fluorescent image, tumor is very bright compared to the normal healthy tissue. This confirms the selective integration of DNP-PLE into tumor membranes with DNP moiety available for binding.

A similar study is performed in which mice receive flank tumors by injection with either adenocarcinoma cells (MDA-MB-231), or osteosarcoma cells (143B). After tumors are established in the groups of mice by subcutaneous injection, the mice receive an intravenous injection of DNP-PLE. Mice are sacrificed and tumors are harvested at various time points post DNP-PLE injection. The tumors are removed and immediately imaged for the presence of the DNP-PLE using an anti-DNP antibody with a fluorescent label. The three different types of cancer all show specific uptake of DNP-PLE, and a multiday day retention time of DNP-PLE.

Example 7—In Vivo Activity of Anti-DNP CARs

In vivo activity of anti-DNP CARs is measured using a xenograft model. A neuroblastoma (Be2) or glioma (U87, U251T, or T98) tumor is established in mice by intracranial injection. Mice receive an intracranial injection of anti-DNP CAR T cells in combination with DNP-PLE. A control group receive an intracranial injection of the anti-DNP CAR T cells only. Mice receiving an intracranial injection of anti-DNP CAR T cells in combination with DNP-PLE have an increased survival rate, decreased tumor burden over time, and/or reduced tumor volume, compared to the control group.

A similar study is performed in which mice receive flank tumors by injection with an adenocarcinoma cells (MDA-MB-231). After tumors are established in the groups of mice by subcutaneous injection, the mice receive an intravenous injection of DNP-PLE, except for a control group. The mice receive a subsequent IV dose of anti-DNP CAR T cells. The mice that received DNP-PLE have an increased survival rate, decreased tumor burden over time, and/or reduced tumor volume, compared to the control group.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and embodiments coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A chimeric antigen receptor (CAR) comprising:

a ligand binding domain which specifically binds to a dinitrophenol (DNP) moiety, wherein the ligand binding domain comprises (i) an amino acid sequence having at least 95% sequence identity to the amino acid sequence set forth in SEQ ID NO:1, SEQ ID NO:7 or SEQ ID NO:12; or (ii) an amino acid sequence having at least 90% sequence identity to the amino acid sequence set forth in SEQ ID NO:8, SEQ ID NO:9, SEQ ID NO:10 or SEQ ID NO:11;

a spacer;

a transmembrane domain; and an intracellular signaling domain.

2. A system comprising:

(a) an effector cell comprising the CAR of claim 1; and (b) a composition comprising a dinitrophenol (DNP) moiety, wherein the CAR specifically binds to the DNP moiety.

3. The system of claim 2, wherein the DNP moiety is attached to the target cell via an antibody or antigen binding fragment thereof that binds to the target cell; or via a lipid integrated into the target cell's surface.

4. The system of claim 3, wherein the target cell is a cancer cell.

5. The system of claim 4, wherein the cancer cell is selected from the group consisting of a breast cancer cell, brain cancer cell, colon cancer cell, renal cancer cell, pancreatic cancer cell, and ovarian cancer cell.

6. The CAR of claim 1, wherein the ligand binding domain comprises an amino acid sequence having at least 95% sequence identity to the amino acid sequence set forth in any of SEQ ID NO:1, SEQ ID NO:9 and SEQ ID NO:10.

7. The CAR of claim 1, wherein the ligand binding domain comprises an amino acid sequence having at least 96% sequence identity to SEQ ID NO:1.

8. The CAR of claim 1, wherein the spacer comprises an IgG4 hinge domain, an IgG4 hinge-CH3 domain, or an IgG4 hinge-CH2-CH3 domain.

9. The CAR of claim 1, wherein the spacer has a length of at least 229 consecutive amino acid residues.

10. The CAR of claim 1, wherein the spacer comprises the amino acid sequence set forth in SEQ ID NO:20.

11. The CAR of claim 1, wherein the transmembrane domain comprises a CD28 transmembrane domain, and the intracellular signaling domain comprises a portion of CD3 zeta and/or a portion of 4-1BB.

12. The system of claim 2, wherein the ligand binding domain comprises an amino acid sequence having at least 95% sequence identity to the amino acid sequence set forth in any of SEQ ID NO:1, SEQ ID NO:9 and SEQ ID NO:10.

13. The system of claim 2, wherein the ligand binding domain comprises an amino acid sequence having at least 95% sequence identity to SEQ ID NO:1 or SEQ ID NO:2.

14. The system of claim 2, wherein the spacer comprises an IgG4 hinge domain, an IgG4 hinge-CH3 domain, or an IgG4 hinge -CH2-CH3 domain.

15. The system of claim 2, wherein the spacer has a length of at least 229 consecutive amino acid residues.

16. The system of claim 2, wherein the spacer comprises the amino acid sequence set forth in SEQ ID NO:20.

17. The system of claim 2, wherein the transmembrane domain comprises a CD28 transmembrane domain, and the intracellular signaling domain comprises a portion of CD3 zeta and/or a portion of 4-1BB.

18. The system of claim 2, wherein the DNP moiety is joined to a phospholipid.

19. The system of claim 18, wherein the phospholipid is a phospholipid ether (PLE).

20. The system of claim 19, wherein the DNP moiety is joined to the PLE by a PEG spacer, and the DNP moiety joined to the PLE by the PEG spacer comprises a structure:

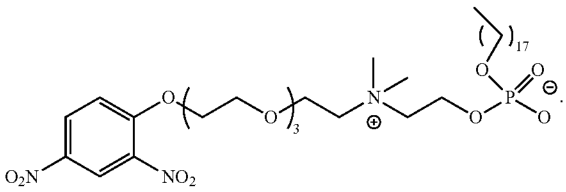

* * * * *